(12) United States Patent
Miyajima et al.

(10) Patent No.: US 8,138,123 B2
(45) Date of Patent: Mar. 20, 2012

(54) GENE EXPRESSING ANALYSIS TOOL

(75) Inventors: Nobuyuki Miyajima, Tsukuba (JP); Akira Horinouchi, Osaka (JP); Kenji Takami, Osaka (JP); Ryota Ise, Chuo-ku (JP)

(73) Assignees: Takeda Pharmaceutical Company Limited, Osaka (JP); Shin Nippon Biomedical Laboratories, Ltd., Kagoshima (JP)

( * ) Notice: Subject to any disclaimer, the term of this patent is extended or adjusted under 35 U.S.C. 154(b) by 720 days.

(21) Appl. No.: 12/162,253

(22) PCT Filed: Jan. 26, 2007

(86) PCT No.: PCT/JP2007/051283
§ 371 (c)(1),
(2), (4) Date: Jul. 25, 2008

(87) PCT Pub. No.: WO2007/086515
PCT Pub. Date: Aug. 2, 2007

(65) Prior Publication Data
US 2009/0048116 A1    Feb. 19, 2009

(30) Foreign Application Priority Data

Jan. 27, 2006   (JP) ................................ 2006-019858

(51) Int. Cl.
*C40B 40/06* (2006.01)
*C40B 60/10* (2006.01)
*C40B 60/12* (2006.01)
*C07H 21/02* (2006.01)

(52) U.S. Cl. .............. 506/16; 506/38; 506/39; 536/23.1
(58) Field of Classification Search .................... 506/16, 506/38, 39; 536/23.1
See application file for complete search history.

(56) References Cited

U.S. PATENT DOCUMENTS

| | | | |
|---|---|---|---|
| 2005/0266471 A1 | 12/2005 | Yamada et al. | |
| 2005/0266474 A1 | 12/2005 | Yamada et al. | |
| 2006/0019283 A1 | 1/2006 | Yamada et al. | |
| 2007/0072175 A1 | 3/2007 | Cooper et al. | |

FOREIGN PATENT DOCUMENTS

| | | |
|---|---|---|
| JP | 2004135552 | 5/2004 |
| JP | 20066313 | 7/2011 |
| JP | 200614723 | 7/2011 |
| JP | 200642802 | 7/2011 |
| WO | 2004035785 A1 | 4/2004 |

OTHER PUBLICATIONS

Chen et al., Apr. 18, 2006, Analysis of 10,000 ESTs from lymphocytes of the cynomolgus monkey to improve our understanding of its immune system, BMC Genomics 7: 82-95.*

Osada et al., 2002, Cynomolgus monkey testicular cDNAs for discovery of novel human genes in the human genome sequence, BMC Genomics, 3: 36-47.*

James F. Dillman III, et al., "Comparison of Non-Human Primate and Human Whole Blood Tissue Gene Expression Profiles," Toxicological Science, 2005, vol. 87, No. 1, pp. 306-314.

Jo Vandesompele, et al., "Accurate Normalization of Real-Time Quantitative RT-PCR Data by Geometric Averaging of Multiple Internal Control Genes," Genome Biology, 2002, vol. 3, No. 7, pp. 1-12.

Lynne V. Abruzzo, et al., "Validation of Oligonucleotide Microarray Data Using Microfluidic Low-Density Arrays: a New Statistical Method to Normalize Real-Time RT-PCR Data," BioTechniques, 2005, vol. 38, No. 5, pp. 785-792.

Joeri L. Aerts, et al., "Selection of Appropriate Control Genes to Assess Expression of Tumor Antigens Using Real-Time RT-PCR," BioTechniques, 2004, vol. 36, No. 1, pp. 84-91.

Pierre M. Durand, et al., "An Analysis of Mobile Genetic Elements in Three *Plasmodium* Species and Their Potential Impact on the Nucleotide Composition of the *P. falciparum* Genome," BMC Genomics, 2006, vol. 7, No. 282, pp. 1-10.

Charles L. Magness, "Analysis of the *Macaca mulatta* Transcriptome and the Sequence Divergence Between *Macaca* and Human," Genome Biology, 2005, vol. 6, No. 7, pp. 1-16.

Hurng-Yi Wang, et al., "Rate of Evolution in Brain-Expressed Genes in Humans and Other Primates," PLoS Biology, Feb. 2007, vol. 5, No. 2, pp. 335-342.

Chen et al, "Analysis of 10,000 ESTS from Lymphocytes of the Cynomolgus Monkey to Improve Our Understanding of Its Immune System", BMC Genomics 7(82):1-14 (2006).

Supplementary European Search Report for EP Application No. 07707515, dated Oct. 13, 2010.

Osada, et al., Substitution Rate and Structural Divergence of 5'UTR Evolution: Comparative Analysis Between Human and Cynomolgus Monkey cDNAs, Mol. Biol. Evol. 22(10):1976-1982 (2005).

Su, et al., Sequence of B2-microglobulin from rhesus macaque (*Macaca mulatta*) includes an allelic variation in the 3'-untranslated region, Immunogenetics, 55:873-877 (2004).

*Macaca mulatta* (rhesus monkey), "Illumingen_MCO_40898 Katze$_{13}$ MMPB2 *Macaca mulatta* cDNA clone IBIUW:25592 5' similar to Bases 5 to 854 highly similar to human Unigene Hs.519421, mRNA sequence." Accession No. CO647746, creation date Jul. 24, 2004, Abstract No. XP-002604723, search date Oct. 13, 2010.

*Macaca fascicularis* (crab-eating macaque), "*Macaca fascularis* sdha mRNA for succinate dehydrogenase flavoprotein subunit, complete cds." Accession No. AB083328, creation date Oct. 9, 2002 (modification date Jun. 24, 2007), Abstract No. XP-002604724, search date Oct. 13, 2010.

(Continued)

*Primary Examiner* — Amber D. Steele
(74) *Attorney, Agent, or Firm* — Sughrue Mion, PLLC

(57) ABSTRACT

The present invention provides a tool for analysis of expression of *Macaca fascicularis* gene expression analysis tool containing a set of nucleic acids containing base sequences the same or substantially the same as two or more base sequences selected from the group consisting of the base sequences shown by SEQ ID NOs:1-14, or partial sequences thereof, and a method of analyzing the expression of *Macaca fascicularis* gene, including measuring a gene transcription product in a *Macaca fascicularis* sample using the tool.

5 Claims, No Drawings

OTHER PUBLICATIONS

*Macaca fascicularis* (crab-eating macaque), "*Macaca fasicularis* HPRT1 mRNA for hydroxanthine phosphoribosyltransferase 1, complete cds". Accession No. AB125173, creation date Sep. 28, 2004, (modification date Oct. 6, 2006), Abstract No. XP-002604725, search date Oct. 13, 2010.

*Macaca mulatta* (rhesus monkey), "Illumingen_MCO_98 Katze_MMPB *Macaca mulatta* cDNA clone IBIUW:6130 5' similar to Bases 1 to 734 highly similar to human PPIA (Hs.356331), mRNA sequence." Accession No. CN641331, creation date May 13, 2004, Abstract No. XP-002604726, search date Oct. 13, 2010.

*Macaca fascicularis* (crab-eating macaque), "*Macaca fascicularis* cDNA clone: Qlv-U391A-E10, 3'end, Sugano cDNA library, expressed in adult liver." Accession No. BB890102, creation date Aug. 6, 2005, (modification date Nov. 18, 2008), Abstract No. XP-002604727, search date Oct. 13, 2010.

*Macaca fascicularis* (crab-eating macaque), "*Macaca fascicularis* PGK1 mRNA for phosphoglycerate kinase 1, complete cds." Accession No. AB125189, creation date Sep. 28, 2004, (modification date Oct. 6, 2006), Abstract No. XP-002604728, search date Oct. 13, 2010.

*Macaca mulatta* (rhesus monkey), "Illumingen_MCO_5944 Katze_MMPL2 *Macaca mulatta* cDNA clone IBIUW:5111 5' similar to Bases 4 to 575 highly similar to human TFRC (Hs.185726), mRNA sequence." Accession No. CN642136, creation date May 13, 2004, Abstract No. XP-002604729, search date Oct. 13, 2010.

*Macaca mulatta* (rhesus monkey), "Illumingen_MCO_10363 Katze_MMPL2 *Macaca mulatta* cDNA clone IBIUW:11867 5' similar to Bases 1 to 898 highly similar to human UBC (Hs.183704), mRNA sequence." Accession No. CN802590, creation date May 27, 2004, Abstract No. XP-002604731, search date Oct. 13, 2010.

\* cited by examiner

GENE EXPRESSING ANALYSIS TOOL

TECHNICAL FIELD

The present invention relates to a novel research tool for analyzing the expression of *Macaca fascicularis* genes and use thereof. More particularly, the present invention relates to a *Macaca fascicularis* gene expression analysis tool comprising a subset of gene transcription products of *Macaca fascicularis*, and a method of analyzing the expression of *Macaca fascicularis* genes using the tool and the like.

BACKGROUND OF THE INVENTION

*Macaca fascicularis* is mostly used in preclinical tests for drug development, and the data of toxicity tests, biochemical and pathological tests and the like have been accumulated. Particularly in toxicity tests, monkey, a primate, is expected to provide more useful data than do rodents such as rat, mouse and the like for extrapolation to human. However, the influence of side effects on various aspects cannot be observed easily from the changes of existent toxicity markers. Particularly, in the initial stages of drug development, therefore, a method of analyzing toxic reactions at a gene expression level attracts attention.

Among others, the microarray technique that simultaneously monitors expression of several to tens of thousand of mRNAs (see patent references 1-4, non-patent references 1 and 2 and the like for DNA microarray) is increasingly utilized for elucidation of mechanism of toxicity and study of toxicity prediction, and expected as a new research field called toxicogenomics. Toxicity phenomena are considered to accompany not only independent changes of one to several genes but also integrated changes wherein many genes are interrelated, such as interaction between genes and cascade and the like. Therefore, use of microarray, a technique permitting analysis at a transcriptome level, is expected to enable comprehensive understanding of the behavior of molecules involved in toxicity expression.

As a DNA microarray for the analysis of the gene expression of non-human primates, GeneChip (registered trade mark) manufactured by Affymetrix containing *Macaca mulatta* ESTs is known. However, *Macaca fascicularis* is mainly used as an experimental animal in Japan. Nevertheless, the current available public database scarcely contains the annotation information of *Macaca fascicularis*.

For example, when searching a gene that can be used as a marker of drug toxicity and the like, reference (internal standard) genes are necessary for detecting changes in gene expression caused by drug administration. As such genes, genes expressed non-specifically to tissue and time and at a relatively high level, i.e., housekeeping genes, are generally used (e.g., see patent reference 5 and the like for human housekeeping gene). As mentioned above, however, the information of *Macaca fascicularis* gene is considerably limited, and many aspects of housekeeping gene are unknown.

patent reference 1: U.S. Pat. No. 5,474,796
patent reference 2: WO95/251116
patent reference 3: WO95/35505
patent reference 4: U.S. Pat. No. 5,605,662
patent reference 5: JP-A-2004-135552
non-patent reference 1: Schena M. et al., Proc. Natl. Acad. Sci. USA, Vol. 93, pp. 10614-10619 (1996)
non-patent reference 2: Heller R. A. et al., Proc. Natl. Acad. Sci. USA, Vol. 94, pp. 2150-2155 (1997)

DISCLOSURE OF THE INVENTION

Problems to be Solved by the Invention

Accordingly, it is an object of the present invention to identify housekeeping genes of *Macaca fascicularis*, and to provide a gene expression analysis tool, for example, DNA microarray, for *Macaca fascicularis*, which contains the genes. A further object of the present invention is to provide a method of analyzing the expression of *Macaca fascicularis* gene(s) using the gene expression analysis tool.

Means of Solving the Problems

In an attempt to achieve the above-mentioned objects, the present inventors have analyzed EST from 6 major organs (liver, kidney, heart, lung, spleen, testis), identified about 16,000 unique sequences, designed 60 mer oligonucleotide probes based on the information and prepared a DNA microarray. As a result of expression analyses using mRNAs derived from various organs, the inventors have identified 14 kinds of genes expressed in all of the above organs at a relatively high level as housekeeping genes of *Macaca fascicularis*.

The present inventors have further studied based on such findings, and completed the present invention.

Accordingly, the present invention provides:

[1] a *Macaca fascicularis* gene expression analysis tool comprising a set of nucleic acids each comprising base sequences the same or substantially the same as each of the base sequences of two or more kinds of nucleic acids selected from the group consisting of 14 kinds of *Macaca fascicularis* gene transcription products comprising the base sequences shown by SEQ ID NOs: 1-14, respectively, or partial sequences thereof;

[2] the tool of the above-mentioned [1], comprising one or more kinds of nucleic acids comprising base sequences the same or substantially the same as base sequences of *Macaca fascicularis* gene transcription products other than the aforementioned 14 kinds of *Macaca fascicularis* gene transcription products, or partial sequences thereof;

[3] the tool of the above-mentioned [1], comprising one or more kinds of nucleic acids comprising base sequences the same or substantially the same as base sequences of a *Macaca fascicularis* gene transcription product specifically expressed in an organ selected from the group consisting of liver, kidney, heart, lung, spleen and testis, and/or corresponding to a drug efficacy target in human, or partial sequences thereof;

[4] the tool of any of the above-mentioned [1] to [3], wherein the set of the nucleic acids is immobilized on a solid phase carrier;

[5] a method of analyzing the expression of *Macaca fascicularis* gene(s), comprising measuring gene transcription product(s) in *Macaca fascicularis* sample(s) using one or more kinds of the tools of the above-mentioned [1] to [4]; and [6] the method of the above-mentioned [5], wherein the *Macaca fascicularis* sample(s) is(are) taken from a *Macaca fascicularis* disease model or *Macaca fascicularis* administered with pharmaceutical agent(s), or isolated *Macaca fascicularis* cell(s) or tissue(s) exposed to pharmaceutical agent(s); and the like.

Effect of the Invention

Since the gene analysis tool of the present invention contains at least two kinds of housekeeping genes of *Macaca fascicularis*, it affords a superior effect in that expressions of

*Macaca fascicularis* gene can be quantitatively compared with each other with high accuracy.

The gene expression analysis tool of the present invention characteristically contains at least a set of nucleic acids capable of detecting two or more kinds of housekeeping gene transcription products of *Macaca fascicularis* (hereinafter sometimes to be referred to as "the nucleic acid set of the present invention"), namely, a set of nucleic acids comprising base sequences the same or substantially the same as base sequences of two or more kinds of housekeeping gene transcription products of *Macaca fascicularis*, or partial sequences thereof. The form of the "gene expression analysis tool" is not particularly limited as long as it contains the above-mentioned set of nucleic acids and includes, but is not limited to, a kit containing, as a component, a reagent comprising each nucleic acid, and a device, apparatus and the like wherein each nucleic acid is immobilized on a solid phase carrier such as array, microplate and the like. The "housekeeping gene" here means a gene commonly expressed in at least liver, kidney, heart, lung, spleen and testis of *Macaca fascicularis* at a high level above a certain level.

Specifically, as a housekeeping gene transcription product of *Macaca fascicularis*, 14 kinds of nucleic acids containing base sequences shown by SEQ ID NOs: 1-14, respectively [in the case of RNA, "t" is read as "u". While Sequence Listing shows sense strand sequences alone, the "base sequence shown by SEQ ID NO: n" in the present specification includes antisense strand and double strand, unless otherwise specified] can be mentioned. Here, the "gene transcription product" is used as a concept encompassing mRNA, as well as double stranded nucleic acid such as cDNA, cRNA and the like. The *Macaca fascicularis* genes containing the base sequences shown by SEQ ID NOs: 1-14 have been named as follows by the Gene Nomenclature Committee (HUGO Nomenclature Committee, HGNC).

| SEQ ID NO: 1: | GAPDH |
| SEQ ID NO: 2: | ACTB |
| SEQ ID NO: 3: | SDHA |
| SEQ ID NO: 4: | RPL4 |
| SEQ ID NO: 5: | TBP |
| SEQ ID NO: 6: | HPRT1 |
| SEQ ID NO: 7: | PPIA |
| SEQ ID NO: 8: | EEF1G |
| SEQ ID NO: 9: | PAPSS2 |
| SEQ ID NO: 10: | PGK1 |
| SEQ ID NO: 11: | TFRC |
| SEQ ID NO: 12: | GUSB |
| SEQ ID NO: 13: | B2M |
| SEQ ID NO: 14: | UBC |

The "base sequence substantially the same" is a base sequence capable of hybridizing to any of the 14 kinds of nucleic acids under highly stringent conditions, which is different from the base sequence of the corresponding region of a nucleic acid ortholog of other mammal. Here, the "highly stringent conditions" mean a hybridization reaction in 6×SSC (sodium chloride/sodium citrate) at 45° C. and subsequent washing once or more with 0.2×SSC/0.1% SDS at 65° C. Examples of the each base sequence substantially the same as the base sequence of each of the 14 kinds of nucleic acids include a base sequence having a homology of 95% or more, preferably 96% or more, more preferably 97% or more, particularly preferably 98% or more, to the base sequence of each of the 14 kinds of nucleic acids. The homology of the base sequence in the present specification can be calculated using a homology calculation algorithm NCBI BLAST (National Center for Biotechnology Information Basic Local Alignment Search Tool) and under the following conditions (expectancy=10; gap allowed; filtering=ON; match score=1; mismatch score=−3).

Examples of each nucleic acid constituting the nucleic acid set of the present invention include a nucleic acid (probe) capable of specifically hybridizing to a housekeeping gene transcription product derived from *Macaca fascicularis*, which is a detection target, a pair of oligonucleotides (primers) capable of acting as a primer for amplifying a part or the whole of the transcription product, and the like. The nucleic acid may be a DNA or an RNA, or a DNA/RNA chimera, with preference given to a DNA.

The nucleic acid to be used as a probe may be double stranded or single stranded. When double stranded, it may be a double stranded DNA, a double stranded RNA or a DNA:RNA hybrid. When single stranded, a sense strand (e.g., for cDNA, cRNA) or an antisense strand (e.g., for mRNA, cDNA) is selected according to the sample to be tested and used. The length of the nucleic acid is not particularly limited as long as it can specifically hybridize to a target nucleic acid and is, for example, about 15 bases or longer, preferably about 30 bases or longer. The nucleic acid is preferably labeled with label reagent(s) to enable detection and quantification of the target nucleic acid. As the label reagent, for example, radioisotope, enzyme, fluorescent substance, luminescent substance and the like can be used. As the radioisotope, for example, [$^{32}$P], [$^{3}$H], [$^{14}$C] and the like can be used. As the enzyme, a stable enzyme having high specific activity is preferable and, for example, β-galactosidase, β-glucosidase, alkaline phosphatase, peroxidase, malate dehydrogenase and the like can be used. As the fluorescent substance, for example, fluorescamine, fluorescein isothiocyanate and the like can be used. As the luminescent substance, for example, luminol, luminol derivative, luciferin, lucigenin and the like can be used. Moreover, biotin-(strept)avidin can also be used for binding of a probe and label reagent(s). To immobilize a nucleic acid to be a probe on a solid phase, a nucleic acid in a sample can be labeled with label reagent(s) such as those mentioned above.

The set of oligonucleotides to be used as primers is not particularly limited as long as the oligonucleotides can specifically hybridize to the sense strand and antisense strand of *Macaca fascicularis*-derived housekeeping gene transcription products containing the base sequences shown by respective SEQ ID NOs, and can amplify DNA fragments between them. An example thereof is a set of oligo DNAs each having a length of about 15—about 100 bases, preferably about 15—about 50 bases, and designed to amplify a DNA fragment of about 100 bp-several kbps.

The nucleic acid that acts as a probe capable of detecting a *Macaca fascicularis*-derived housekeeping gene transcription product can be acquired by amplifying a desired length of a nucleic acid by PCR using the above-mentioned primer set capable of amplifying a part or whole of a transcription product of the gene, and cDNA or genomic DNA derived from any cell of *Macaca fascicularis* [e.g., hepatocyte, splenocyte, nerve cell, glial cell, pancreatic β cell, bone marrow cell, mesangial cell, Langerhans cell, epidermal cell, epithelial cell, goblet cell, endothelial cell, smooth muscle cell, fibroblast, fibrocyte, muscle cell, adipocyte, immune cell (e.g., macrophage, T cell, B cell, natural killer cell, mast cell, neutrophil, basophil, eosinophil, monocyte), megakaryocyte, synovial cell, chondrocyte, osteocyte, osteoblast, osteoclast, mammary cell, hepatocyte or interstitial cell, or precursor cell, stem cells or cancer cell of these cells and the like] or any tissue in which such cell is present [for example, brain, a part of brain (e.g., olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidney, liver, gonad, thyroid gland, gall bladder, bone marrow, adrenal gland, skin, lung, gastrointestinal tract (e.g., large intestine, small intestine), blood vessel, heart, thymus, spleen, submandibular gland, peripheral blood, prostate, orchis, ovary, placenta, uterus, bone, articular, adipose tissue, skeletal muscle and the like] as a template, or cloning the above-mentioned housekeeping gene(s) or cDNA(s) from a CDNA or genomic DNA library from the aforementioned cell or tissue by colony or plaque hybridization and the like and preparing a fragment having a suitable length using, where necessary, a restriction enzyme and the like. The hybridization can be performed, for example, according to the method described in Molecular Cloning, $2^{nd}$ edition, and the like. When using a commercially available library, hybridization can be performed according to the method described in the instruction manual attached to the library. Alternatively, the nucleic acid can also be obtained based on the information of each base sequence (e.g., base sequences shown by SEQ ID NOs: 1-14) of *Macaca fascicularis*-derived housekeeping gene product, by chemically synthesizing a part or whole of the base sequence and/or its complementary sequence, using a commercially available DNA/RNA automatic synthesizer and the like. In addition, a chip (array) with a solid phased nucleic acid can also be prepared by directly synthesizing the nucleic acid in situ (on chip) on a solid phase such as silicon, glass and the like.

The gene expression analysis tool of the present invention may contain, in addition to a set of nucleic acids capable of detecting two or more kinds of housekeeping gene transcription products of *Macaca fascicularis*, one or more kinds of nucleic acids comprising base sequences the same or substantially the same as base sequences of *Macaca fascicularis* gene transcription products other than the aforementioned 14 kinds of *Macaca fascicularis* gene transcription products, or partial sequences thereof. Any kind and any number of such nucleic acids can be appropriately selected according to the purpose of use of the gene expression analysis tool of the present invention. For comprehensive analysis of the expression of *Macaca fascicularis* gene, for example, the tool can contain all gene products that are expressed in any organ, tissue and the like, and further, a nucleic acid for detecting the products of all genes on the genome. For detection of the expression of a particular toxicity marker or disease marker gene, for example, the tool can contain only a nucleic acid for detecting the objective gene product, besides the above-mentioned nucleic acid for the detection of a housekeeping gene.

In a preferable embodiment, such nucleic acid contains a base sequence the same or substantially the same as the base sequence of a *Macaca fascicularis* gene transcription product specifically expressed in organs such as liver, kidney, heart, lung, spleen, testis and the like, or corresponding to a drug efficacy target in human, or a partial sequence thereof. A gene expressed in an organ specific manner can be acquired by comparing the expressions of respective genes in various organs shown in the Examples below, and selecting a gene whose expression is detected in a particular organ.

Such nucleic acids can be provided as a solid in a dry state or in the form of an alcohol precipitate, or also in a dissolved state in water or suitable buffer (e.g., TE buffer etc.). When used as a labeled probe, the nucleic acid may be previously labeled with any of the above-mentioned labeling substances, or may be provided separately from labeling substances and labeled when in use.

Alternatively, the nucleic acid can also be provided as immobilized on a suitable solid phase. Examples of the solid phase include, but are not limited to, glass, silicon, plastic, nitrocellulose, nylon, polyvinylidene difluoride and the like. Examples of the immobilizing means include, but are not limited to a method by introducing in advance, a functional group such as amino group, aldehyde group, SH group, biotin and the like into a nucleic acid, introducing a functional group (e.g., aldehyde group, amino group, SH group, streptavidin and the like) capable of reacting with the nucleic acid onto a solid phase, and crosslinking the solid phase and the nucleic acid by a covalent bond between the both functional groups, or a method by coating a solid phase with polycation and immobilizing the polyanionic nucleic acid by electrostatic binding and the like.

One preferable embodiment wherein a nucleic acid probe is immobilized on a solid phase is a DNA microarray. A DNA microarray can be produced by an Affymetrix method wherein a nucleic acid probe is synthesized by one nucleotide on a substrate (glass, silicon and the like), or a Stanford method wherein a nucleic acid probe prepared in advance is spotted on the substrate.

For quantitative analysis of the expression of a *Macaca fascicularis*-derived housekeeping gene using a trace amount of an RNA sample, competitive RT-PCR or real-time RT-PCR is preferably used. Competitive RT-PCR refers to a method including performing a competitive amplification reaction in the presence of, as a competitor, a known amount of other template nucleic acid that can be amplified by a set of primers capable of amplifying the objective DNA in the reaction mixture, and calculating the amount of the objective DNA by comparing the amounts of amplified products. When competitive RT-PCR is employed, therefore, the reagent of the present invention can further contain, in addition to the above-mentioned primer set, a nucleic acid which is amplified by the primer set to produce an amplification product (e.g., amplification product different from the object DNA in size, amplification product different from the object DNA in migration pattern by a restriction enzyme treatment and the like) that can be distinguished from the object DNA. The competitor nucleic acid may be a DNA or an RNA. In the case of DNA, PCR can be performed with addition of a competitor after synthesizing cDNA from an RNA sample by a reverse transcription reaction, and in the case of RNA, RT-PCR is performed with addition of a competitor to an RNA sample from the start. In the latter case, since the efficiency of the reverse transcription reaction is also taken into consideration, an absolute amount of the original mRNA can be assumed.

In contrast, since real-time RT-PCR permits real-time monitoring of amplification amount by PCR, electrophoresis is not necessary and the expression of a *Macaca fascicularis*-derived housekeeping gene can be analyzed more rapidly. Generally, monitoring is performed using various fluorescent reagents. Among them are a reagent that binds to double stranded DNA to emit fluorescence (intercalator) such as SYBR Green I, ethidium bromide and the like, as well as a nucleic acid that can be used as the above-mentioned probe (the nucleic acid hybridizes to a target nucleic acid within an amplification region) with one end modified by a fluorescent substance (e.g., FAM, HEX, TET, FITC etc.) and the other end by a quenching substance (e.g., TAMRA, DABCYL etc.) and the like.

The present invention also provides a method of analyzing the expression of *Macaca fascicularis* gene, which comprises measuring a gene transcription product in a *Macaca fascicularis*-derived sample using one or more kinds of the above-mentioned gene analysis tool of the present invention.

For example, the gene analysis tool of the present invention can be used for detection identification of a disease marker gene, a pharmacological action marker gene or a pharmaceutical agent toxicity marker gene using a cell-containing sample collected from *Macaca fascicularis* which is a disease model or *Macaca fascicularis* administered with a pharmaceutical agent, or isolated *Macaca fascicularis* cell or tissue exposed to a pharmaceutical agent (including culture and established cell line derived therefrom) and the like, and further preferably used for the analyses of disease mechanism, pharmacological action mechanism, toxicity action mechanism and the like.

Examples of the cell-containing sample taken from *Macaca fascicularis* include any cells [for example, hepatocyte, splenocyte, nerve cells, glial cell, pancreatic β cell, bone marrow cell, mesangial cell, Langerhans cell, epidermal cell, epithelial cells, goblet cell, endothelial cell, smooth muscle cell, fibroblast, fibrocyte, muscle cell, adipocyte, immune cell (e.g., macrophage, T cell, B cell, natural killer cell, mast cell, neutrophil, basophil, eosinophils, monocyte), megakaryocyte, synovial cell, chondrocyte, osteocyte, osteoblast, osteoclast, mammary cell, interstitial cell, or precursor cell, stem cell or cancer cell of these cells and the like] or any tissue in which such cells are present [e.g., brain, each part of brain (e.g., olfactory bulb, amygdaloid nucleus, basal ganglia, hippocampus, thalamus, hypothalamus, cerebral cortex, medulla oblongata, cerebellum), spinal cord, eyeball, pituitary gland, stomach, pancreas, kidney, liver, gonad, thyroid gland, gall bladder, bone marrow, adrenal gland, skin, lung, gastrointestinal tract (e.g., large intestine, small intestine), blood vessel, heart, thymus, spleen, submandibular gland, peripheral blood, prostate, orchis, ovary, placenta, uterus, bone, articular, adipose tissue, skeletal muscle and the like] and the like. Among these, blood (e.g., peripheral blood), lymphocyte and the like are preferable since they can be collected rapidly and conveniently and are less-invasive to animals, and the like.

Examples of the isolated *Macaca fascicularis* cell or tissue to be expose to a pharmaceutical agent include those similar to the above-mentioned, a primary culture or a passage culture thereof, or a cell line established from the above-mentioned cell•tissue, and the like can be mentioned. For good reproducibility and easy availability, and the like, cell lines are preferably used.

Gene expression in a cell-containing sample taken from *Macaca fascicularis* or a sample of isolated *Macaca fascicularis* cell or tissue exposed to a pharmaceutical agent can be examined by preparing an RNA (e.g., total RNA, mRNA) fraction from the sample, and detecting a transcription product of the marker gene in the fraction. While an RNA fraction can be prepared by a known means such as guanidine-CsCl ultracentrifugation method, AGPC method and the like, total RNA with high purity can be prepared rapidly and conveniently from a trace amount of a sample using a commercially available RNA extraction kit (e.g., RNeasy Mini Kit; QIAGEN etc.). As a means of detecting a gene transcription product in an RNA fraction, for example, a method using hybridization (Northern blot, dot blot, DNA chip (microarray) analysis etc.), a method using PCR (RT-PCR, competitive PCR, real-time PCR etc.) and the like can be mentioned. Quantitative PCRs such as competitive PCR, real-time PCR and the like are preferable since changes in the gene expression can be detected rapidly and conveniently with good quantifiability from a trace amount of a sample, and DNA chip (microarray) analysis is preferable since changes in the expression of a plurality of marker genes can be simultaneously detected and quantifiability can be improved by the selection of the detection method and the like.

When Northern blot or dot blot hybridization is performed, gene expression can be detected by using the above-mentioned gene analysis tool of the present invention containing nucleic acid(s) to be used as a labeled probe. Namely, in the case of Northern hybridization, an RNA fraction prepared as mentioned above is separated by gel electrophoresis, transferred to a membrane of nitrocellulose, nylon, polyvinylidene difluoride and the like, subjected to hybridization in a hybridization buffer containing the reagent of the present invention or each reagent in the kit of the present invention under the above-mentioned "highly stringent conditions", and the amount of the labels bound to the membrane is measured for each band by a suitable method, whereby the expression level of each gene can be measured. Also in the case of dot blot, an RNA fraction spotted on a membrane is subjected to a hybridization reaction in the same manner (performed for each gene), and the amount of the labels of the spot is measured, whereby the expression level of each gene can be measured.

In the case of DNA chip (microarray) analysis, for example, cDNA with a suitable promoter such as T7 promoter introduced is synthesized by a reverse transcription reaction from an RNA fraction prepared as mentioned above, and then cRNA is synthesized using RNA polymerase (labeled cRNA can be obtained by using, as a substrate, mononucleotide labeled with biotin and the like at this point). The labeled cRNA is contacted with the above-mentioned solid phased probe to perform a hybridization reaction, and the amount of the labels bound to each probe on the solid phase is measured, whereby the expression level of each gene can be measured. The method is advantageous in terms of rapidness and convenience as the number of genes to be detected (accordingly, probes to be solid phased) increases.

Abbreviations for bases, amino acids and the like used in the present description are based on abbreviations specified by the IUPAC-IUB Commission on Biochemical Nomenclature or abbreviations in common use in relevant fields, some examples of which are given below. When an optical isomer may be present in amino acid, it is of the L-configuration, unless otherwise stated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate The SEQ ID NOs in the Sequence Listing in the present specification show the following sequences.

SEQ ID NO: 1: base sequence of *Macaca fascicularis*-derived GAPDH gene product fragment
SEQ ID NO: 2: base sequence of *Macaca fascicularis*-derived ACTB gene product fragment
SEQ ID NO: 3: base sequence of *Macaca fascicularis*-derived SDHA gene product fragment
SEQ ID NO: 4: base sequence of *Macaca fascicularis*-derived RPL4 gene product fragment SEQ ID NO: 5: base sequence of *Macaca fascicularis*-derived TBP gene product fragment SEQ ID NO: 6: base sequence of *Macaca fascicularis*-derived HPRT1 gene product fragment SEQ ID NO: 7: base sequence of *Macaca fascicularis*-derived PPIA gene product fragment SEQ ID NO: 8: base sequence of *Macaca fascicularis*-derived EEF1G gene product fragment SEQ ID NO: 9: base sequence of *Macaca fascicularis*-derived PAPSS2 gene product fragment SEQ ID NO: 10: base sequence of *Macaca fascicularis*-derived PGK1 gene product fragment SEQ ID NO: 11: base sequence of *Macaca fascicularis*-derived TFRC gene product fragment SEQ ID NO: 12: base sequence of *Macaca fascicularis*-derived GUSB gene product fragment SEQ ID NO: 13: base sequence of *Macaca fascicularis*-derived B2M gene product fragment SEQ ID NO: 14: base sequence of *Macaca fascicularis*-derived UBC gene product fragment The present invention is explained in more detail in the following by referring to the Examples, which are mere exemplifications and do not limit the scope of the present invention in any way.

EXAMPLE 1

RNA was extracted from 6 major organs (liver, kidney, heart, lung, spleen, testis) of *Macaca fascicularis* by a conventional method, cDNA libraries were prepared, and 128,063 clones in total were sequenced. Excluding 200 bases or below, the number of valid data was 81,743 (average 635 base-long). By a comparison thereof with public human gene database, it was found that 8,316 genes having a homology with human were included. In addition, the genes were divided into families and examined to find that the EST data was of a good quality with a little bias.

EXAMPLE 2

About 16000 unique sequences were identified by the EST analyses in Example 1, and 60 mer oligonucleotide probes were designed based on the information thereof. Each probe was on-chip synthesized according to a conventional method to construct a DNA microarray.

EXAMPLE 3

The gene expression status in each organ and tissue of a normal *Macaca fascicularis* [total 27 parts; 5 animals for each part (total 129 analyses, due to some lacking parts and combined parts)] was examined using the DNA microarray constructed in Example 2. As a result, the 14 *Macaca fascicularis* genes shown in the Tables were expressed in all organs and tissues, and they were confirmed to be housekeeping genes. In the Tables, Cy5 represents a sample RNA of each part, and Cy3 represents a Universal Control RNA common to all 129 analyses [a mixture of equal amounts of total RNA of liver (lateral left lobe), kidney (cortex+medulla), heart (left ventricular wall), lung (left lung posterior lobe), spleen and testis of animal NOs. 7-11]. Ratio shows the ratio of the numerical value of Cy5 to that of Cy3.

TABLE 1 expression data of 14 genes in each tissue - (1) [Cy5]

| | | | collected organ | | | | | | | | |
|---|---|---|---|---|---|---|---|---|---|---|---|
| | | | thyroid gland/parathyroid gland | | | | | adrenal gland | | | |
| | | | collected part | | | | | | | | |
| | | | — | | | | | cortex | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 19 | 42 | 65 | 88 | 111 | 20 | 43 | 66 | 89 | 112 |
| | | | Cy5 | | | | | | | | |
| PAPSS2 | SN009c31T_N07 | MK002114_1 | 276 | 334 | 293 | 351 | 382 | 1636 | 3651 | 1585 | 2550 | 3453 |
| EEF1G | SN117a11T_E03 | MK000784_2 | 11482 | 14462 | 14048 | 13373 | 13978 | 8578 | 10465 | 8124 | 10001 | 10512 |
| HPRT1 | SN020d53T_J14 | MK000286_1 | 604 | 632 | 535 | 617 | 674 | 433 | 608 | 421 | 420 | 531 |
| PPIA | SN021d41T_B12 | MK005336_3 | 3225 | 3907 | 3553 | 4209 | 3540 | 1532 | 2553 | 1609 | 2517 | 2388 |
| PGK1 | SN091c21T_J05 | MK000332_3 | 3080 | 1687 | 1646 | 1633 | 2683 | 1744 | 1952 | 1587 | 1880 | 3293 |
| RPL4 | SN311b27T_E08 | MK000581_3 | 14268 | 20482 | 16990 | 22218 | 17687 | 6576 | 14126 | 8774 | 14604 | 11591 |
| GAPDH | SN299b55T_M14 | MK001057_3 | 9425 | 8127 | 5721 | 4110 | 6225 | 2992 | 4457 | 3429 | 4308 | 4528 |
| TBP | SN147b69T_I18 | MK001519_1 | 239 | 266 | 284 | 303 | 315 | 122 | 163 | 178 | 199 | 225 |
| SDHA | SN032d28T_H08 | MK001905_1 | 2366 | 2435 | 1716 | 2209 | 1903 | 1825 | 2728 | 2334 | 2404 | 2864 |
| GUSB | SN102d12T_H04 | MK000279_1 | 1177 | 1557 | 1642 | 1781 | 1969 | 738 | 1283 | 1101 | 1486 | 1507 |
| ACTB | SN263b46T_K12 | MK000668_2 | 25854 | 37548 | 43872 | 38611 | 37851 | 12634 | 19025 | 20051 | 21129 | 24711 |
| UBC | SN032d35T_F10 | MK005306_5 | 35129 | 43199 | 32221 | 36900 | 37423 | 22239 | 25682 | 22841 | 27226 | 33040 |
| B2M | SN252c26T_D07 | MK001845_10 | 40111 | 39235 | 45703 | 41588 | 56046 | 22245 | 27691 | 26522 | 28826 | 37507 |
| TFRC | SN252a02T_C01 | MK001530_1 | 1189 | 1345 | 1638 | 1593 | 2426 | 418 | 775 | 576 | 704 | 862 |
| | | average | 1887 | 1959 | 1858 | 1934 | 1951 | 1567 | 1933 | 1802 | 1978 | 2004 |
| | | median | 480 | 496 | 490 | 486 | 492 | 460 | 459 | 448 | 446 | 446 |
| | | standard deviation | 7066 | 7026 | 6832 | 7277 | 7172 | 6826 | 7294 | 7470 | 8464 | 8324 |
| | | number of valid spots | 16283 | 16204 | 16202 | 16199 | 16242 | 16178 | 16152 | 16157 | 16164 | 16229 |

TABLE 1-continued expression data of 14 genes in each tissue - (1) [Cy5]

| | | | collected organ | | | | | | | |
|---|---|---|---|---|---|---|---|---|---|---|
| | | | adrenal gland | | | | gastrointestinal tract | | | |
| | | | collected part | | | | | | | |
| | | | medulla | | | | stomach (gastric corpus) | | | |
| | | | animal No. | | | | | | | |
| | | | 7 | 8 | 9 | 10 | 11 | 7 | 8 | 9 | 10 | 11 |
| | | | sample No. | | | | | | | |
| Symbol | EST | Sequence_ID | 21 | 44 | 67 | 90 | 113 | 22 | 45 | 68 | 91 | 114 |
| | | | | | Cy5 | | | | | | | |
| PAPSS2 | SN009c31T_N07 | MK002114_1 | 2146 | 3470 | 1181 | 1583 | 3541 | 689 | 844 | 863 | 827 | 1230 |
| EEF1G | SN117a11T_E03 | MK000784_2 | 8615 | 8161 | 6594 | 7646 | 8851 | 9313 | 11104 | 12934 | 10450 | 13033 |
| HPRT1 | SN020d53T_J14 | MK000286_1 | 850 | 886 | 636 | 1090 | 919 | 644 | 945 | 466 | 487 | 482 |
| PPIA | SN021d41T_B12 | MK005336_3 | 2202 | 2555 | 1972 | 2687 | 2656 | 2505 | 3294 | 2717 | 2840 | 4275 |
| PGK1 | SN091c21T_J05 | MK000332_3 | 2694 | 2122 | 1903 | 2138 | 3823 | 1668 | 1518 | 1259 | 929 | 2509 |
| RPL4 | SN311b27T_E08 | MK000581_3 | 10976 | 12898 | 8709 | 13655 | 12370 | 13277 | 17217 | 13859 | 16020 | 18428 |
| GAPDH | SN299b55T_M14 | MK001057_3 | 4173 | 5416 | 4637 | 6363 | 5284 | 3949 | 5809 | 6010 | 4290 | 7003 |
| TBP | SN147b69T_I18 | MK001519_1 | 194 | 206 | 191 | 237 | 249 | 199 | 221 | 256 | 176 | 246 |
| SDHA | SN032d28T_H08 | MK001905_1 | 2553 | 2965 | 2378 | 2200 | 3067 | 2023 | 2828 | 1781 | 1432 | 2381 |
| GUSB | SN102d12T_H04 | MK000279_1 | 1274 | 1531 | 1272 | 1342 | 1579 | 748 | 1214 | 1829 | 1197 | 2589 |
| ACTB | SN263b46T_K12 | MK000668_2 | 18295 | 16618 | 18421 | 18292 | 21181 | 29341 | 45592 | 69457 | 37672 | 52225 |
| UBC | SN032d35T_F10 | MK005306_5 | 28028 | 30532 | 27660 | 35613 | 36526 | 30033 | 38249 | 41671 | 25982 | 35186 |
| B2M | SN252c26T_D07 | MK001845_10 | 26299 | 28049 | 22867 | 23122 | 31105 | 37957 | 50790 | 41834 | 19015 | 76714 |
| TFRC | SN252a02T_C01 | MK001530_1 | 709 | 846 | 990 | 1509 | 1205 | 1172 | 1325 | 1035 | 1271 | 2602 |
| | | average | 1653 | 1892 | 1682 | 1875 | 1900 | 1901 | 2106 | 1990 | 2098 | 1992 |
| | | median | 443 | 444 | 438 | 440 | 442 | 440 | 444 | 446 | 449 | 450 |
| | | standard deviation | 6578 | 6986 | 6935 | 7252 | 6985 | 8021 | 7858 | 7583 | 8335 | 8391 |
| | | number of valid spots | 16280 | 16256 | 16245 | 16302 | 16282 | 16210 | 16278 | 16306 | 16394 | 16236 |

| | | | collected organ | | | | |
|---|---|---|---|---|---|---|---|
| | | | gastrointestinal tract | | | | |
| | | | collected part | | | | |
| | | | stomach (pylorus) | | | | |
| | | | animal No. | | | | |
| | | | 7 | 8 | 9 | 10 | 11 |
| | | | sample No. | | | | |
| Symbol | EST | Sequence_ID | 23 | 46 | 69 | 92 | 115 |
| PAPSS2 | SN009c31T_N07 | MK002114_1 | 619 | 597 | 996 | 752 | 1017 |
| EEF1G | SN117a11T_E03 | MK000784_2 | 14867 | 13511 | 10246 | 12587 | 12617 |
| HPRT1 | SN020d53T_J14 | MK000286_1 | 489 | 440 | 697 | 510 | 475 |
| PPIA | SN021d41T_B12 | MK005336_3 | 3832 | 3833 | 2402 | 3419 | 3898 |
| PGK1 | SN091c21T_J05 | MK000332_3 | 2326 | 1405 | 1182 | 1157 | 2555 |
| RPL4 | SN311b27T_E08 | MK000581_3 | 20333 | 19786 | 10889 | 17428 | 17388 |
| GAPDH | SN299b55T_M14 | MK001057_3 | 6135 | 6922 | 5236 | 5760 | 6354 |
| TBP | SN147b69T_I18 | MK001519_1 | 244 | 237 | 212 | 208 | 263 |
| SDHA | SN032d28T_H08 | MK001905_1 | 2048 | 1687 | 2805 | 1983 | 2333 |
| GUSB | SN102d12T_H04 | MK000279_1 | 1529 | 1718 | 989 | 1575 | 2626 |
| ACTB | SN263b46T_K12 | MK000668_2 | 53255 | 65328 | 40603 | 55279 | 51052 |
| UBC | SN032d35T_F10 | MK005306_5 | 43696 | 47065 | 35739 | 33362 | 32562 |
| B2M | SN252c26T_D07 | MK001845_10 | 51054 | 53641 | 23318 | 29668 | 82329 |
| TFRC | SN252a02T_C01 | MK001530_1 | 1226 | 1392 | 993 | 1193 | 2686 |
| | | average | 2041 | 2099 | 2089 | 1906 | 1982 |
| | | median | 451 | 453 | 453 | 452 | 453 |
| | | standard deviation | 7878 | 7672 | 8483 | 7307 | 8066 |
| | | number of valid spots | 16321 | 16309 | 16227 | 16293 | 16310 |

TABLE 2

| | | | [Cy3] | | | | | | | | | |
|---|---|---|---|---|---|---|---|---|---|---|---|---|
| | | | collected organ | | | | | | | | | |
| | | | thyroid gland/parathyroid gland | | | | | adrenal gland | | | | |
| | | | collected part | | | | | | | | | |
| | | | — | | | | | cortex | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 19 | 42 | 65 | 88 | 111 | 20 | 43 | 66 | 89 | 112 |
| | | | Cy3 | | | | | | | | | |
| PAPSS2 | SN009c31T_N07 | MK002114_1 | 678 | 802 | 789 | 813 | 860 | 422 | 680 | 599 | 644 | 696 |
| EEF1G | SN117a11T_E03 | MK000784_2 | 9348 | 11530 | 11039 | 11195 | 12258 | 7259 | 9903 | 8337 | 8873 | 9890 |
| HPRT1 | SN020d53T_J14 | MK000286_1 | 1120 | 1343 | 1237 | 1274 | 1385 | 661 | 1044 | 917 | 982 | 1093 |
| PPIA | SN021d41T_B12 | MK005336_3 | 3151 | 3680 | 3622 | 3742 | 3837 | 1784 | 3120 | 2685 | 2960 | 3187 |
| PGK1 | SN091c21T_J05 | MK000332_3 | 2196 | 2600 | 2452 | 2750 | 2730 | 1338 | 2254 | 1943 | 2146 | 2284 |
| RPL4 | SN311b27T_E08 | MK000581_3 | 15953 | 20546 | 18437 | 20044 | 20163 | 6775 | 14544 | 13332 | 14177 | 15633 |
| GAPDH | SN299b55T_M14 | MK001057_3 | 8528 | 9977 | 10666 | 10666 | 11312 | 6732 | 9165 | 7362 | 8484 | 8937 |
| TBP | SN147b69T_I18 | MK001519_1 | 238 | 272 | 257 | 275 | 276 | 129 | 210 | 187 | 227 | 219 |
| SDHA | SN032d28T_H08 | MK001905_1 | 3766 | 4804 | 4619 | 4661 | 4814 | 2116 | 3875 | 3166 | 3502 | 3697 |
| GUSB | SN102d12T_H04 | MK000279_1 | 1484 | 1738 | 1683 | 1845 | 1875 | 689 | 1419 | 1232 | 1389 | 1457 |
| ACTB | SN263b46T_K12 | MK000668_2 | 33788 | 39243 | 37635 | 40185 | 42245 | 19712 | 36682 | 31476 | 33983 | 36720 |
| UBC | SN032d35T_F10 | MK005306_5 | 35031 | 42133 | 41789 | 41857 | 41573 | 27283 | 34462 | 30366 | 35250 | 34759 |
| B2M | SN252c26T_D07 | MK001845_10 | 53145 | 76730 | 56563 | 77993 | 77153 | 29489 | 50683 | 48326 | 52694 | 55780 |
| TFRC | SN252a02T_C01 | MK001530_1 | 999 | 1144 | 1041 | 1052 | 1195 | 578 | 846 | 744 | 847 | 840 |
| | | average | 1950 | 2363 | 2313 | 2142 | 2417 | 1530 | 2043 | 1799 | 1926 | 1946 |
| | | median | 508 | 530 | 525 | 522 | 528 | 496 | 496 | 488 | 487 | 487 |
| | | standard deviation | 7250 | 12081 | 12240 | 9467 | 12889 | 5943 | 7602 | 6667 | 6868 | 6879 |
| | | number of valid spots | 16283 | 16204 | 16202 | 16199 | 16242 | 16178 | 16152 | 16157 | 16164 | 16229 |

| | | | collected organ | | | | | | | | | |
|---|---|---|---|---|---|---|---|---|---|---|---|---|
| | | | adrenal gland | | | | | gastrointestinal tract | | | | |
| | | | collected part | | | | | | | | | |
| | | | medulla | | | | | stomach (gastric corpus) | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 21 | 44 | 67 | 90 | 113 | 22 | 45 | 68 | 91 | 114 |
| | | | Cy3 | | | | | | | | | |
| PAPSS2 | SN009c31T_N07 | MK002114_1 | 610 | 689 | 620 | 763 | 787 | 656 | 740 | 763 | 672 | 759 |
| EEF1G | SN117a11T_E03 | MK000784_2 | 8994 | 10535 | 8941 | 10844 | 11221 | 9699 | 11516 | 10888 | 9492 | 10885 |
| HPRT1 | SN020d53T_J14 | MK000286_1 | 1074 | 1157 | 941 | 1179 | 1302 | 1063 | 1410 | 1277 | 1006 | 1238 |
| PPIA | SN021d41T_B12 | MK005336_3 | 2652 | 3372 | 2747 | 3202 | 3361 | 2963 | 3555 | 3261 | 2954 | 3490 |
| PGK1 | SN091c21T_J05 | MK000332_3 | 1918 | 2358 | 2054 | 2418 | 2508 | 2266 | 2617 | 2484 | 2197 | 2546 |
| RPL4 | SN311b27T_E08 | MK000581_3 | 13311 | 16993 | 14680 | 17082 | 18229 | 15985 | 18442 | 18980 | 13576 | 18257 |
| GAPDH | SN299b55T_M14 | MK001057_3 | 8061 | 9210 | 7968 | 9689 | 9501 | 8681 | 10189 | 9597 | 8856 | 9673 |
| TBP | SN147b69T_I18 | MK001519_1 | 211 | 234 | 210 | 250 | 248 | 215 | 258 | 275 | 218 | 254 |
| SDHA | SN032d28T_H08 | MK001905_1 | 3474 | 4107 | 3536 | 4235 | 3996 | 3333 | 3716 | 4276 | 3089 | 4233 |
| GUSB | SN102d12T_H04 | MK000279_1 | 1232 | 1592 | 1297 | 1599 | 1613 | 1427 | 1653 | 1676 | 1375 | 1664 |
| ACTB | SN263b46T_K12 | MK000668_2 | 30167 | 37282 | 32386 | 37800 | 40425 | 34376 | 39586 | 31657 | 31939 | 34817 |
| UBC | SN032d35T_F10 | MK005306_5 | 31174 | 36601 | 30539 | 36988 | 36670 | 34593 | 40182 | 39187 | 33427 | 38747 |
| B2M | SN252c26T_D07 | MK001845_10 | 44157 | 54441 | 48767 | 58572 | 58087 | 52771 | 59158 | 58419 | 53319 | 48563 |
| TFRC | SN252a02T_C01 | MK001530_1 | 946 | 876 | 816 | 1069 | 970 | 934 | 950 | 968 | 796 | 1106 |
| | | average | 1758 | 2036 | 1894 | 2019 | 2141 | 1858 | 2154 | 2018 | 2067 | 2030 |
| | | median | 483 | 484 | 479 | 481 | 483 | 480 | 484 | 486 | 487 | 488 |
| | | standard deviation | 6883 | 7783 | 9465 | 7674 | 11019 | 7067 | 7590 | 7466 | 7544 | 8202 |
| | | number of valid spots | 16280 | 16256 | 16245 | 16302 | 16282 | 16210 | 16278 | 16306 | 16394 | 16236 |

TABLE 2-continued

[Cy3]

| | | | | collected organ gastrointestinal tract collected part stomach (pylorus) animal No. | | | | |
|---|---|---|---|---|---|---|---|---|
| | | | | 7 | 8 | 9 | 10 | 11 |
| | | | | | | sample No. | | |
| Symbol | EST | Sequence_ID | | 23 | 46 | 69 | 92 | 115 |
| PAPSS2 | SN009c31T_N07 | MK002114_1 | | 732 | 766 | 704 | 686 | 686 |
| EEF1G | SN117a11T_E03 | MK000784_2 | | 11067 | 10965 | 10551 | 10670 | 10226 |
| HPRT1 | SN020d53T_J14 | MK000286_1 | | 1270 | 1266 | 1090 | 1176 | 1191 |
| PPIA | SN021d41T_B12 | MK005336_3 | | 3668 | 3500 | 3281 | 3314 | 3323 |
| PGK1 | SN091c21T_J05 | MK000332_3 | | 2721 | 2565 | 2403 | 2440 | 2466 |
| RPL4 | SN311b27T_E08 | MK000581_3 | | 17835 | 16895 | 16357 | 16436 | 17331 |
| GAPDH | SN299b55T_M14 | MK001057_3 | | 9543 | 9867 | 9663 | 9227 | 8918 |
| TBP | SN147b69T_I18 | MK001519_1 | | 259 | 251 | 238 | 225 | 246 |
| SDHA | SN032d28T_H08 | MK001905_1 | | 4131 | 4212 | 3797 | 4055 | 3973 |
| GUSB | SN102d12T_H04 | MK000279_1 | | 1794 | 1598 | 1478 | 1506 | 1556 |
| ACTB | SN263b46T_K12 | MK000668_2 | | 35294 | 34056 | 32951 | 30557 | 30495 |
| UBC | SN032d35T_F10 | MK005306_5 | | 40454 | 37076 | 38082 | 35418 | 34943 |
| B2M | SN252c26T_D07 | MK001845_10 | | 59773 | 58322 | 56775 | 55628 | 42675 |
| TFRC | SN252a02T_C01 | MK001530_1 | | 875 | 981 | 929 | 941 | 970 |
| | | average | | 2028 | 2081 | 2076 | 1903 | 2020 |
| | | median | | 488 | 490 | 490 | 489 | 489 |
| | | standard deviation | | 7327 | 7396 | 7797 | 6903 | 8898 |
| | | number of valid spots | | 16321 | 16309 | 16227 | 16293 | 16310 |

TABLE 3

[Ratio]

| | | | collected organ | | | | | | | | |
|---|---|---|---|---|---|---|---|---|---|---|---|
| | | | thyroid gland/parathyroid gland | | | | | adrenal gland | | | |
| | | | collected part | | | | | | | | |
| | | | — | | | | | cortex | | | |
| | | | animal No. | | | | | | | | |
| | | | 7 | 8 | 9 | 10 | 11 | 7 | 8 | 9 | 10 | 11 |
| | | | | | | | sample No. | | | | |
| Symbol | EST | Sequence_ID | 19 | 42 | 65 | 88 | 111 | 20 | 43 | 66 | 89 | 112 |
| | | | | | | | Ratio | | | | |
| PAPSS2 | SN009c31T_N07 | MK002114_1 | 0.41 | 0.42 | 0.37 | 0.43 | 0.44 | 3.88 | 5.37 | 2.64 | 3.96 | 4.96 |
| EEF1G | SN117a11T_E03 | MK000784_2 | 1.23 | 1.25 | 1.27 | 1.19 | 1.14 | 1.18 | 1.06 | 0.97 | 1.13 | 1.06 |
| HPRT1 | SN020d53T_J14 | MK000286_1 | 0.54 | 0.47 | 0.43 | 0.48 | 0.49 | 0.65 | 0.58 | 0.46 | 0.43 | 0.49 |
| PPIA | SN021d41T_B12 | MK005336_3 | 1.02 | 1.06 | 0.98 | 1.13 | 0.92 | 0.86 | 0.82 | 0.60 | 0.85 | 0.75 |
| PGK1 | SN091c21T_J05 | MK000332_3 | 1.40 | 0.65 | 0.67 | 0.59 | 0.98 | 1.30 | 0.87 | 0.82 | 0.88 | 1.44 |
| RPL4 | SN311b27T_E08 | MK000581_3 | 0.89 | 1.00 | 0.92 | 1.11 | 0.88 | 0.97 | 0.97 | 0.66 | 1.03 | 0.74 |
| GAPDH | SN299b55T_M14 | MK001057_3 | 1.11 | 0.81 | 0.55 | 0.39 | 0.55 | 0.44 | 0.49 | 0.47 | 0.51 | 0.51 |
| TBP | SN147b69T_I18 | MK001519_1 | 1.01 | 0.98 | 1.11 | 1.10 | 1.14 | 0.94 | 0.78 | 0.95 | 0.88 | 1.03 |
| SDHA | SN032d28T_H08 | MK001905_1 | 0.63 | 0.51 | 0.37 | 0.47 | 0.40 | 0.86 | 0.70 | 0.74 | 0.69 | 0.77 |
| GUSB | SN102d12T_H04 | MK000279_1 | 0.79 | 0.90 | 0.98 | 0.97 | 1.05 | 1.07 | 0.90 | 0.89 | 1.07 | 1.03 |
| ACTB | SN263b46T_K12 | MK000668_2 | 0.77 | 0.96 | 1.17 | 0.96 | 0.90 | 0.64 | 0.52 | 0.64 | 0.62 | 0.67 |
| UBC | SN032d35T_F10 | MK005306_5 | 1.00 | 1.03 | 0.77 | 0.88 | 0.90 | 0.82 | 0.75 | 0.75 | 0.77 | 0.95 |
| B2M | SN252c26T_D07 | MK001845_10 | 0.75 | 0.51 | 0.81 | 0.53 | 0.73 | 0.75 | 0.55 | 0.55 | 0.55 | 0.67 |
| TFRC | SN252a02T_C01 | MK001530_1 | 1.19 | 1.18 | 1.57 | 1.51 | 2.03 | 0.72 | 0.92 | 0.77 | 0.83 | 1.03 |

| collected organ | |
|---|---|
| adrenal gland | gastrointestinal tract |
| collected part | |
| medulla | stomach (gastric corpus) |

TABLE 3-continued

[Ratio]

| | | | animal No. | | | | | | | | |
|---|---|---|---|---|---|---|---|---|---|---|---|
| | | | 7 | 8 | 9 | 10 | 11 | 7 | 8 | 9 | 10 | 11 |
| | | | | | | | | sample No. | | | | |
| Symbol | EST | Sequence_ID | 21 | 44 | 67 | 90 | 113 | 22 | 45 | 68 | 91 | 114 |
| | | | | | Ratio | | | | | | | |
| PAPSS2 | SN009c31T_N07 | MK002114_1 | 3.52 | 5.04 | 1.91 | 2.07 | 4.50 | 1.05 | 1.14 | 1.13 | 1.23 | 1.62 |
| EEF1G | SN117a1IT_E03 | MK000784_2 | 0.96 | 0.77 | 0.74 | 0.71 | 0.79 | 0.96 | 0.96 | 1.19 | 1.10 | 1.20 |
| HPRT1 | SN020d53T_J14 | MK000286_1 | 0.79 | 0.77 | 0.68 | 0.93 | 0.71 | 0.61 | 0.67 | 0.37 | 0.48 | 0.39 |
| PPIA | SN021d41T_B12 | MK005336_3 | 0.83 | 0.76 | 0.72 | 0.84 | 0.79 | 0.85 | 0.93 | 0.83 | 0.96 | 1.22 |
| PGK1 | SN091c21T_J05 | MK000332_3 | 1.40 | 0.90 | 0.93 | 0.88 | 1.52 | 0.74 | 0.58 | 0.51 | 0.42 | 0.99 |
| RPL4 | SN311b27T_E08 | MK000581_3 | 0.82 | 0.76 | 0.59 | 0.80 | 0.68 | 0.83 | 0.93 | 0.73 | 1.18 | 1.01 |
| GAPDH | SN299b55T_M14 | MK001057_3 | 0.52 | 0.59 | 0.58 | 0.66 | 0.56 | 0.45 | 0.57 | 0.63 | 0.48 | 0.72 |
| TBP | SN147b69T_I18 | MK001519_1 | 0.92 | 0.88 | 0.91 | 0.94 | 1.01 | 0.92 | 0.86 | 0.93 | 0.80 | 0.97 |
| SDHA | SN032d28T_H08 | MK001905_1 | 0.73 | 0.72 | 0.67 | 0.52 | 0.77 | 0.61 | 0.76 | 0.42 | 0.46 | 0.56 |
| GUSB | SN102d12T_H04 | MK000279_1 | 1.03 | 0.96 | 0.98 | 0.84 | 0.98 | 0.52 | 0.73 | 1.09 | 0.87 | 1.56 |
| ACTB | SN263b46T_K12 | MK000668_2 | 0.61 | 0.45 | 0.57 | 0.48 | 0.52 | 0.85 | 1.15 | 2.19 | 1.18 | 1.50 |
| UBC | SN032d35T_F10 | MK005306_5 | 0.90 | 0.83 | 0.91 | 0.96 | 1.00 | 0.87 | 0.95 | 1.06 | 0.78 | 0.91 |
| B2M | SN252c26T_D07 | MK001845_10 | 0.60 | 0.52 | 0.47 | 0.39 | 0.54 | 0.72 | 0.86 | 0.72 | 0.36 | 1.58 |
| TFRC | SN252a02T_C01 | MK001530_1 | 0.75 | 0.97 | 1.21 | 1.41 | 1.24 | 1.25 | 1.39 | 1.07 | 1.60 | 2.35 |

| | | | collected organ | | | | |
|---|---|---|---|---|---|---|---|
| | | | gastrointestinal tract | | | | |
| | | | collected part | | | | |
| | | | stomach (pylorus) | | | | |
| | | | animal No. | | | | |
| | | | 7 | 8 | 9 | 10 | 11 |
| | | | sample No. | | | | |
| Symbol | EST | Sequence_ID | 23 | 46 | 69 | 92 | 115 |
| PAPSS2 | SN009c31T_N07 | MK002114_1 | 0.85 | 0.78 | 1.42 | 1.10 | 1.48 |
| EEF1G | SN117a1IT_E03 | MK000784_2 | 1.34 | 1.23 | 0.97 | 1.18 | 1.23 |
| HPRT1 | SN020d53T_J14 | MK000286_1 | 0.38 | 0.35 | 0.64 | 0.43 | 0.40 |
| PPIA | SN021d41T_B12 | MK005336_3 | 1.04 | 1.09 | 0.73 | 1.03 | 1.17 |
| PGK1 | SN091c21T_J05 | MK000332_3 | 0.85 | 0.55 | 0.49 | 0.47 | 1.04 |
| RPL4 | SN311b27T_E08 | MK000581_3 | 1.14 | 1.17 | 0.67 | 1.06 | 1.00 |
| GAPDH | SN299b55T_M14 | MK001057_3 | 0.64 | 0.70 | 0.54 | 0.62 | 0.71 |
| TBP | SN147b69T_I18 | MK001519_1 | 0.94 | 0.94 | 0.89 | 0.92 | 1.07 |
| SDHA | SN032d28T_H08 | MK001905_1 | 0.50 | 0.40 | 0.74 | 0.49 | 0.59 |
| GUSB | SN102d12T_H04 | MK000279_1 | 0.85 | 1.08 | 0.67 | 1.05 | 1.69 |
| ACTB | SN263b46T_K12 | MK000668_2 | 1.51 | 1.92 | 1.23 | 1.81 | 1.67 |
| UBC | SN032d35T_F10 | MK005306_5 | 1.08 | 1.27 | 0.94 | 0.94 | 0.93 |
| B2M | SN252c26T_D07 | MK001845_10 | 0.85 | 0.92 | 0.41 | 0.53 | 1.93 |
| TFRC | SN252a02T_C01 | MK001530_1 | 1.40 | 1.42 | 1.07 | 1.27 | 2.77 |

TABLE 4 expression data of 14 genes in each tissue - (2)
[Cy5]

| | | | collected organ | | | | | | | | |
|---|---|---|---|---|---|---|---|---|---|---|---|
| | | | gastrointestinal tract | | | | | gastrointestinal tract | | | | |
| | | | collected part | | | | | | | | | |
| | | | duodenum | | | | | jejunum | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 24 | 47 | 70 | 93 | 116 | 25 | 48 | 71 | 94 | 117 |
| PAPSS2 | SN009c31T_N07 | MK002114_1 | 2003 | 1203 | 1320 | 2622 | 1452 | 3178 | 2968 | 2106 | 2946 | 3692 |
| EEF1G | SN117a11T_E03 | MK000784_2 | 11916 | 12605 | 13643 | 12652 | 11991 | 11088 | 10662 | 11101 | 10904 | 13764 |
| HPRT1 | SN020d53T_J14 | MK000286_1 | 377 | 334 | 360 | 349 | 308 | 398 | 361 | 311 | 395 | 385 |
| PPIA | SN021d41T_B12 | MK005336_3 | 3108 | 2917 | 2814 | 4329 | 3412 | 3589 | 3200 | 3569 | 4325 | 4440 |
| PGK1 | SN091c21T_J05 | MK000332_3 | 2998 | 1366 | 1462 | 1830 | 2465 | 3756 | 1874 | 2262 | 1984 | 3612 |
| RPL4 | SN311b27T_E08 | MK000581_3 | 12188 | 15544 | 13262 | 20314 | 13231 | 12663 | 14299 | 11114 | 14819 | 15854 |

TABLE 4-continued expression data of 14 genes in each tissue - (2)
[Cy5]

| Symbol | EST | Sequence_ID | | | | | | | | | | |
|---|---|---|---|---|---|---|---|---|---|---|---|---|
| GAPDH | SN299b55T_M14 | MK001057_3 | 8196 | 7078 | 6126 | 10167 | 7692 | 9805 | 8752 | 8431 | 8922 | 10532 |
| TBP | SN147b69T_I18 | MK001519_1 | 192 | 179 | 193 | 237 | 229 | 238 | 218 | 214 | 243 | 291 |
| SDHA | SN032d28T_H08 | MK001905_1 | 3742 | 2410 | 3225 | 4520 | 3514 | 3437 | 2807 | 3916 | 3498 | 3980 |
| GUSB | SN102d12T_H04 | MK000279_1 | 958 | 1589 | 1720 | 1763 | 1625 | 1615 | 2845 | 2967 | 2859 | 3502 |
| ACTB | SN263b46T_K12 | MK000668_2 | 45491 | 37139 | 45186 | 50469 | 41886 | 37585 | 43419 | 43879 | 49855 | 53887 |
| UBC | SN032d35T_F10 | MK005306_5 | 28085 | 31104 | 28789 | 32133 | 28931 | 32911 | 35103 | 26545 | 33497 | 36175 |
| B2M | SN252c26T_D07 | MK001845_10 | 63426 | 48551 | 48864 | 50668 | 48926 | 88234 | 110015 | 83482 | 70618 | 85170 |
| TFRC | SN252a02T_C01 | MK001530_1 | 2078 | 1612 | 1685 | 1544 | 1554 | 1951 | 2543 | 2154 | 2015 | 2565 |
| | | average | 1856 | 1879 | 2014 | 2167 | 2014 | 1997 | 1978 | 1901 | 1962 | 2040 |
| | | median | 450 | 449 | 448 | 448 | 448 | 449 | 449 | 449 | 449 | 452 |
| | | standard deviation | 7123 | 7350 | 8852 | 8243 | 7860 | 7023 | 7101 | 6994 | 7145 | 6848 |
| | | number of valid spots | 16131 | 16162 | 16243 | 16174 | 16246 | 16282 | 16262 | 16297 | 16204 | 16228 |

| | | | collected organ | | | | | | | | | |
|---|---|---|---|---|---|---|---|---|---|---|---|---|
| | | | gastrointestinal tract | | | | | gastrointestinal tract | | | | |
| | | | collected part | | | | | | | | | |
| | | | ileum | | | | | colon | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 26 | 49 | 72 | 95 | 118 | 27 | 50 | 73 | 96 | 119 |
| PAPSS2 | SN009c31T_N07 | MK002114_1 | 2342 | 3624 | 2746 | 1861 | 1943 | 1434 | 1873 | 2403 | 2665 | 2401 |
| EEF1G | SN117a11T_E03 | MK000784_2 | 12446 | 11307 | 12220 | 9979 | 13096 | 14675 | 12904 | 12532 | 13541 | 16288 |
| HPRT1 | SN020d53T_J14 | MK000286_1 | 389 | 406 | 470 | 353 | 469 | 519 | 502 | 443 | 564 | 557 |
| PPIA | SN021d41T_B12 | MK005336_3 | 3793 | 3322 | 3827 | 3489 | 3624 | 4328 | 4066 | 3989 | 5469 | 5701 |
| PGK1 | SN091c21T_J05 | MK000332_3 | 3085 | 1754 | 2196 | 1288 | 2871 | 2803 | 1371 | 1680 | 1998 | 3315 |
| RPL4 | SN311b27T_E08 | MK000581_3 | 15387 | 16356 | 13924 | 15553 | 15887 | 19784 | 16691 | 14691 | 18829 | 15880 |
| GAPDH | SN299b55T_M14 | MK001057_3 | 8976 | 9236 | 9340 | 7330 | 8425 | 7982 | 7212 | 8057 | 10252 | 11080 |
| TBP | SN147b69T_I18 | MK001519_1 | 273 | 266 | 255 | 223 | 267 | 261 | 208 | 247 | 286 | 279 |
| SDHA | SN032d28T_H08 | MK001905_1 | 2543 | 2165 | 2767 | 2284 | 2384 | 2504 | 1837 | 2296 | 2554 | 2636 |
| GUSB | SN102d12T_H04 | MK000279_1 | 1638 | 3917 | 3631 | 2887 | 2640 | 1524 | 2530 | 2967 | 2768 | 3010 |
| ACTB | SN263b46T_K12 | MK000668_2 | 49756 | 53627 | 60732 | 50728 | 56723 | 61640 | 63370 | 75969 | 72962 | 78661 |
| UBC | SN032d35T_F10 | MK005306_5 | 29928 | 41188 | 34597 | 27755 | 33559 | 38522 | 34286 | 37357 | 33047 | 36227 |
| B2M | SN252c26T_D07 | MK001845_10 | 87102 | 102810 | 97886 | 62986 | 107094 | 59464 | 61430 | 56233 | 37708 | 59396 |
| TFRC | SN252a02T_C01 | MK001530_1 | 1813 | 2742 | 2479 | 1648 | 1809 | 3055 | 3080 | 2796 | 2294 | 2489 |
| | | average | 2063 | 2066 | 2066 | 1809 | 2043 | 2018 | 2037 | 2013 | 2101 | 1943 |
| | | median | 454 | 455 | 457 | 456 | 457 | 458 | 458 | 458 | 460 | 461 |
| | | standard deviation | 7143 | 7258 | 7306 | 6653 | 7946 | 7394 | 7712 | 7435 | 7181 | 7209 |
| | | number of valid spots | 16217 | 16277 | 16255 | 16231 | 16214 | 16216 | 16260 | 16211 | 16263 | 16190 |

| | | | collected organ | | | | |
|---|---|---|---|---|---|---|---|
| | | | liver | | | | |
| | | | collected part | | | | |
| | | | lateral left lobe | | | | |
| | | | animal No. | | | | |
| | | | 7 | 8 | 9 | 10 | 11 |
| | | | sample No. | | | | |
| Symbol | EST | Sequence_ID | 28 | 51 | 74 | 97 | 120 |
| PAPSS2 | SN009c31T_N07 | MK002114_1 | 997 | 1275 | 1137 | 1048 | 1507 |
| EEF1G | SN117a11T_E03 | MK000784_2 | 7677 | 10293 | 9396 | 8250 | 10080 |
| HPRT1 | SN020d53T_J14 | MK000286_1 | 622 | 733 | 700 | 474 | 685 |
| PPIA | SN021d41T_B12 | MK005336_3 | 2933 | 5141 | 2587 | 3434 | 3519 |
| PGK1 | SN091c21T_J05 | MK000332_3 | 1965 | 1677 | 1354 | 1181 | 2312 |
| RPL4 | SN311b27T_E08 | MK000581_3 | 10857 | 15934 | 9418 | 13523 | 12043 |
| GAPDH | SN299b55T_M14 | MK001057_3 | 6803 | 12875 | 9412 | 8457 | 9650 |
| TBP | SN147b69T_I18 | MK001519_1 | 179 | 197 | 199 | 143 | 172 |
| SDHA | SN032d28T_H08 | MK001905_1 | 3509 | 4897 | 4098 | 3467 | 4176 |
| GUSB | SN102d12T_H04 | MK000279_1 | 1608 | 2880 | 1800 | 1973 | 2006 |
| ACTB | SN263b46T_K12 | MK000668_2 | 11381 | 16047 | 13642 | 14047 | 15229 |
| UBC | SN032d35T_F10 | MK005306_5 | 35256 | 45246 | 30989 | 30150 | 34697 |
| B2M | SN252c26T_D07 | MK001845_10 | 23388 | 23791 | 27021 | 20966 | 34314 |
| TFRC | SN252a02T_C01 | MK001530_1 | 664 | 651 | 695 | 587 | 812 |

TABLE 4-continued expression data of 14 genes in each tissue - (2)

[Cy5]

|  |  |  |  |  |  |  |  |  |  |  |  |  |
|---|---|---|---|---|---|---|---|---|---|---|---|---|
|  |  |  |  |  |  | average | 2254 | 2583 | 2275 | 2168 | 2496 |  |
|  |  |  |  |  |  | median | 461 | 462 | 462 | 462 | 463 |  |
|  |  |  |  |  |  | standard deviation | 8780 | 9708 | 8938 | 8143 | 9369 |  |
|  |  |  |  |  |  | number of valid spots | 16255 | 16221 | 16240 | 16289 | 16278 |  |

TABLE 5

[Cy3]

| | | | collected organ | | | | | | | |
|---|---|---|---|---|---|---|---|---|---|---|
| | | | gastrointestinal tract | | | | gastrointestinal tract | | | |
| | | | | | collected part | | | | | |
| | | | duodenum | | | | jejunum | | | |
| | | | | | animal No. | | | | | |
| | | | 7 | 8 | 9 | 10 | 11 | 7 | 8 | 9 | 10 | 11 |
| | | | | | sample No. | | | | | |
| Symbol | EST | Sequence_ID | 24 | 47 | 70 | 93 | 116 | 25 | 48 | 71 | 94 | 117 |
| PAPSS2 | SN009c31T_N07 | MK002114_1 | 631 | 643 | 638 | 736 | 650 | 740 | 732 | 666 | 781 | 790 |
| EEF1G | SN117a11T_E03 | MK000784_2 | 8811 | 9379 | 9029 | 10368 | 9189 | 10099 | 10059 | 9439 | 11198 | 12551 |
| HPRT1 | SN020d53T_J14 | MK000286_1 | 995 | 983 | 1025 | 1175 | 1007 | 1166 | 1116 | 1026 | 1210 | 1283 |
| PPIA | SN021d41T_B12 | MK005336_3 | 2713 | 2762 | 2892 | 3285 | 3069 | 3358 | 3023 | 3040 | 3580 | 3664 |
| PGK1 | SN091c21T_J05 | MK000332_3 | 1972 | 2008 | 2061 | 2346 | 2139 | 2282 | 2252 | 2221 | 2539 | 2677 |
| RPL4 | SN311b27T_E08 | MK000581_3 | 13589 | 13647 | 14462 | 17426 | 14998 | 15792 | 15346 | 14763 | 16447 | 18871 |
| GAPDH | SN299b55T_M14 | MK001057_3 | 8178 | 8758 | 8439 | 10147 | 8549 | 9355 | 9283 | 8456 | 10173 | 10970 |
| TBP | SN147b69T_I18 | MK001519_1 | 194 | 193 | 209 | 231 | 217 | 245 | 230 | 223 | 243 | 264 |
| SDHA | SN032d28T_H08 | MK001905_1 | 3504 | 3521 | 3705 | 4359 | 3615 | 3998 | 3979 | 3836 | 4302 | 4710 |
| GUSB | SN102d12T_H04 | MK000279_1 | 1171 | 1213 | 1306 | 1540 | 1356 | 1465 | 1407 | 1350 | 1600 | 1730 |
| ACTB | SN263b46T_K12 | MK000668_2 | 27508 | 29232 | 29155 | 34791 | 31319 | 32522 | 31087 | 28402 | 33390 | 35740 |
| UBC | SN032d35T_F10 | MK005306_5 | 33123 | 33414 | 35222 | 39002 | 33511 | 34376 | 33274 | 35590 | 38129 | 39139 |
| B2M | SN252c26T_D07 | MK001845_10 | 38182 | 41497 | 46040 | 59087 | 47114 | 36781 | 31723 | 36985 | 45458 | 44935 |
| TFRC | SN252a02T_C01 | MK001530_1 | 888 | 773 | 961 | 932 | 820 | 874 | 904 | 898 | 1002 | 1122 |
| | | average | 1792 | 1796 | 2013 | 2052 | 1951 | 2011 | 1985 | 2025 | 2030 | 2155 |
| | | median | 486 | 484 | 483 | 483 | 482 | 483 | 483 | 482 | 482 | 485 |
| | | standard deviation | 6800 | 6606 | 9371 | 7252 | 7564 | 7234 | 7642 | 9656 | 7619 | 9281 |
| | | number of valid spots | 16131 | 16162 | 16243 | 16174 | 16246 | 16282 | 16262 | 16297 | 16204 | 16228 |

| | | | collected organ | | | | | | | |
|---|---|---|---|---|---|---|---|---|---|---|
| | | | gastrointestinal tract | | | | gastrointestinal tract | | | |
| | | | | | collected part | | | | | |
| | | | ileum | | | | colon | | | |
| | | | | | animal No. | | | | | |
| | | | 7 | 8 | 9 | 10 | 11 | 7 | 8 | 9 | 10 | 11 |
| | | | | | sample No. | | | | | |
| Symbol | EST | Sequence_ID | 26 | 49 | 72 | 95 | 118 | 27 | 50 | 73 | 96 | 119 |
| PAPSS2 | SN009c31T_N07 | MK002114_1 | 726 | 761 | 838 | 694 | 800 | 682 | 667 | 684 | 775 | 805 |
| EEF1G | SN117a11T_E03 | MK000784_2 | 10848 | 11042 | 11900 | 9846 | 11414 | 10069 | 9792 | 9810 | 10816 | 12577 |
| HPRT1 | SN020d53T_J14 | MK000286_1 | 1137 | 1238 | 1382 | 1078 | 1232 | 1174 | 1140 | 1109 | 1152 | 1310 |
| PPIA | SN021d41T_B12 | MK005336_3 | 3444 | 3420 | 3685 | 2928 | 3373 | 3178 | 2968 | 3276 | 3402 | 3734 |
| PGK1 | SN091c21T_J05 | MK000332_3 | 2445 | 2580 | 2650 | 2336 | 2545 | 2482 | 2173 | 2407 | 2502 | 2724 |
| RPL4 | SN311b27T_E08 | MK000581_3 | 16029 | 18358 | 18912 | 15369 | 16765 | 17236 | 14146 | 17310 | 15357 | 17426 |
| GAPDH | SN299b55T_M14 | MK001057_3 | 9642 | 10008 | 11158 | 9076 | 10493 | 9123 | 8927 | 8726 | 9920 | 11364 |
| TBP | SN147b69T_I18 | MK001519_1 | 244 | 266 | 246 | 228 | 251 | 247 | 229 | 247 | 247 | 239 |
| SDHA | SN032d28T_H08 | MK001905_1 | 4131 | 4598 | 4223 | 4011 | 4790 | 4213 | 3734 | 3895 | 4339 | 4324 |
| GUSB | SN102d12T_H04 | MK000279_1 | 1549 | 1678 | 1717 | 1494 | 1526 | 1597 | 1394 | 1566 | 1578 | 1824 |
| ACTB | SN263b46T_K12 | MK000668_2 | 33413 | 31521 | 32849 | 27956 | 31449 | 30842 | 28895 | 29068 | 29828 | 32035 |
| UBC | SN032d35T_F10 | MK005306_5 | 36122 | 37204 | 40810 | 34400 | 40070 | 37913 | 35486 | 36131 | 37009 | 38869 |
| B2M | SN252c26T_D07 | MK001845_10 | 38465 | 34798 | 36545 | 41662 | 35723 | 49365 | 44592 | 50954 | 53916 | 71696 |
| TFRC | SN252a02T_C01 | MK001530_1 | 1003 | 1064 | 1063 | 886 | 1078 | 964 | 952 | 894 | 957 | 978 |

TABLE 5-continued

[Cy3]

| | | | | | | | | | | |
|---|---|---|---|---|---|---|---|---|---|---|
| average | 2116 | 2072 | 2136 | 1922 | 2095 | 1995 | 1951 | 1976 | 2210 | 1991 |
| median | 487 | 488 | 489 | 489 | 490 | 490 | 490 | 490 | 492 | 492 |
| standard deviation | 7494 | 7430 | 7739 | 7567 | 7786 | 7044 | 6777 | 7063 | 8759 | 7389 |
| number of valid spots | 16217 | 16277 | 16255 | 16231 | 16214 | 16216 | 16260 | 16211 | 16263 | 16190 | collected organ: liver
collected part: lateral left lobe

| | | | animal No. | 7 | 8 | 9 | 10 | 11 |
|---|---|---|---|---|---|---|---|---|
| | | | sample No. | 28 | 51 | 74 | 97 | 120 |
| Symbol | EST | Sequence_ID | | | | | | |
| PAPSS2 | SN009c31T_N07 | MK002114_1 | | 684 | 768 | 690 | 621 | 722 |
| EEF1G | SN117a11T_E03 | MK000784_2 | | 9763 | 11919 | 10305 | 8898 | 10758 |
| HPRT1 | SN020d53T_J14 | MK000286_1 | | 1070 | 1285 | 1090 | 1033 | 1193 |
| PPIA | SN021d41T_B12 | MK005336_3 | | 3119 | 3685 | 2960 | 2876 | 3219 |
| PGK1 | SN091c21T_J05 | MK000332_3 | | 2215 | 2764 | 2211 | 1972 | 2337 |
| RPL4 | SN311b27T_E08 | MK000581_3 | | 15475 | 19771 | 16060 | 13859 | 16726 |
| GAPDH | SN299b55T_M14 | MK001057_3 | | 9481 | 10257 | 9288 | 7964 | 9650 |
| TBP | SN147b69T_I18 | MK001519_1 | | 217 | 254 | 230 | 209 | 213 |
| SDHA | SN032d28T_H08 | MK001905_1 | | 4002 | 4609 | 4293 | 3633 | 4328 |
| GUSB | SN102d12T_H04 | MK000279_1 | | 1396 | 1764 | 1365 | 1271 | 1472 |
| ACTB | SN263b46T_K12 | MK000668_2 | | 36349 | 44402 | 36155 | 33543 | 38478 |
| UBC | SN032d35T_F10 | MK005306_5 | | 36460 | 45344 | 39486 | 31949 | 39057 |
| B2M | SN252c26T_D07 | MK001845_10 | | 53514 | 50704 | 52515 | 48209 | 53805 |
| TFRC | SN252a02T_C01 | MK001530_1 | | 936 | 932 | 993 | 891 | 1025 |
| | | average | | 1906 | 2189 | 1994 | 1862 | 2166 |
| | | median | | 492 | 493 | 493 | 493 | 494 |
| | | standard deviation | | 6402 | 7283 | 7597 | 6256 | 8099 |
| | | number of valid spots | | 16255 | 16221 | 16240 | 16289 | 16278 |

TABLE 6

[Ratio]

collected organ

| | | | gastrointestinal tract | | | | | gastrointestinal tract collected part | | | | | gastrointestinal tract | | | |
|---|---|---|---|---|---|---|---|---|---|---|---|---|---|---|---|---|
| | | | duodenum | | | | | jejunum | | | | | ileum | | | |
| | | | animal No. | | | | | | | | | | | | | |
| | | | 7 | 8 | 9 | 10 | 11 | 7 | 8 | 9 | 10 | 11 | 7 | 8 | 9 | 10 |
| | | | sample No. | | | | | | | | | | | | | |
| Symbol | EST | Sequence_ID | 24 | 47 | 70 | 93 | 116 | 25 | 48 | 71 | 94 | 117 | 26 | 49 | 72 | 95 |
| PAPSS2 | SN009c31T_N07 | MK002114_1 | 3.17 | 1.87 | 2.07 | 3.56 | 2.24 | 4.30 | 4.06 | 3.16 | 3.77 | 4.67 | 3.23 | 4.76 | 3.28 | 2.68 |
| EEF1G | SN117a11T_E03 | MK000784_2 | 1.35 | 1.34 | 1.51 | 1.22 | 1.30 | 1.10 | 1.06 | 1.18 | 0.97 | 1.10 | 1.15 | 1.02 | 1.03 | 1.01 |
| HPRT1 | SN020d53T_J14 | MK000286_1 | 0.38 | 0.34 | 0.35 | 0.30 | 0.31 | 0.34 | 0.32 | 0.30 | 0.33 | 0.30 | 0.34 | 0.33 | 0.34 | 0.33 |
| PPIA | SN021d41T_B12 | MK005336_3 | 1.15 | 1.06 | 0.97 | 1.32 | 1.11 | 1.07 | 1.06 | 1.17 | 1.21 | 1.21 | 1.10 | 0.97 | 1.04 | 1.19 |
| PGK1 | SN091c21T_J05 | MK000332_3 | 1.52 | 0.68 | 0.71 | 0.78 | 1.15 | 1.65 | 0.83 | 1.02 | 0.78 | 1.35 | 1.26 | 0.68 | 0.83 | 0.55 |
| RPL4 | SN311b27T_E08 | MK000581_3 | 0.90 | 1.14 | 0.92 | 1.17 | 0.88 | 0.80 | 0.93 | 0.75 | 0.90 | 0.84 | 0.96 | 0.89 | 0.74 | 1.01 |
| GAPDH | SN299b55T_M14 | MK001057_3 | 1.00 | 0.81 | 0.73 | 1.00 | 0.90 | 1.05 | 0.94 | 1.00 | 0.88 | 0.96 | 0.93 | 0.92 | 0.84 | 0.81 |
| TBP | SN147b69T_I18 | MK001519_1 | 0.99 | 0.93 | 0.93 | 1.03 | 1.05 | 0.97 | 0.95 | 0.96 | 1.00 | 1.10 | 1.12 | 1.00 | 1.04 | 0.98 |
| SDHA | SN032d28T_H08 | MK001905_1 | 1.07 | 0.68 | 0.87 | 1.04 | 0.97 | 0.86 | 0.71 | 1.02 | 0.81 | 0.85 | 0.62 | 0.47 | 0.66 | 0.57 |
| GUSB | SN102d12T_H04 | MK000279_1 | 0.82 | 1.31 | 1.32 | 1.14 | 1.20 | 1.10 | 2.02 | 2.20 | 1.79 | 2.02 | 1.06 | 2.33 | 2.12 | 1.93 |
| ACTB | SN263b46T_K12 | MK000668_2 | 1.65 | 1.27 | 1.55 | 1.45 | 1.34 | 1.16 | 1.40 | 1.54 | 1.49 | 1.51 | 1.49 | 1.70 | 1.85 | 1.81 |
| UBC | SN032d35T_F10 | MK005306_5 | 0.85 | 0.93 | 0.82 | 0.82 | 0.86 | 0.96 | 1.05 | 0.75 | 0.88 | 0.92 | 0.83 | 1.11 | 0.85 | 0.81 |
| B2M | SN252c26T_D07 | MK001845_10 | 1.66 | 1.17 | 1.06 | 0.86 | 1.04 | 2.40 | 3.47 | 2.26 | 1.55 | 1.90 | 2.26 | 2.95 | 2.68 | 1.51 |
| TFRC | SN252a02T_C01 | MK001530_1 | 2.34 | 2.08 | 1.75 | 1.66 | 1.90 | 2.23 | 2.81 | 2.40 | 2.01 | 2.29 | 1.81 | 2.58 | 2.33 | 1.86 |

TABLE 6-continued

[Ratio]

| | | | collected organ | | | | | | | | | |
|---|---|---|---|---|---|---|---|---|---|---|---|---|
| | | | gastrointestinal tract | gastrointestinal tract | | | | | liver | | | |
| | | | | collected part | | | | | | | | |
| | | | ileum | colon | | | | | lateral left lobe | | | |
| | | | | | | | animal No. | | | | | |
| | | | 11 | 7 | 8 | 9 | 10 | 11 | 7 | 8 | 9 | 10 | 11 |
| | | | | | | | sample No. | | | | | |
| Symbol | EST | Sequence_ID | 118 | 27 | 50 | 73 | 96 | 119 | 28 | 51 | 74 | 97 | 120 |
| PAPSS2 | SN009c31T_N07 | MK002114_1 | 2.43 | 2.10 | 2.81 | 3.51 | 3.44 | 2.98 | 1.46 | 1.66 | 1.65 | 1.69 | 2.09 |
| EEF1G | SN117a11T_E03 | MK000784_2 | 1.15 | 1.46 | 1.32 | 1.28 | 1.25 | 1.30 | 0.79 | 0.86 | 0.91 | 0.93 | 0.94 |
| HPRT1 | SN020d53T_J14 | MK000286_1 | 0.38 | 0.44 | 0.44 | 0.40 | 0.49 | 0.42 | 0.58 | 0.57 | 0.64 | 0.46 | 0.57 |
| PPIA | SN021d41T_B12 | MK005336_3 | 1.07 | 1.36 | 1.37 | 1.22 | 1.61 | 1.53 | 0.94 | 1.40 | 0.87 | 1.19 | 1.09 |
| PGK1 | SN091c21T_J05 | MK000332_3 | 1.13 | 1.13 | 0.63 | 0.70 | 0.80 | 1.22 | 0.89 | 0.61 | 0.61 | 0.60 | 0.99 |
| RPL4 | SN311b27T_E08 | MK000581_3 | 0.95 | 1.15 | 1.18 | 0.85 | 1.23 | 0.91 | 0.70 | 0.81 | 0.59 | 0.98 | 0.72 |
| GAPDH | SN299b55T_M14 | MK001057_3 | 0.80 | 0.87 | 0.81 | 0.92 | 1.03 | 0.98 | 0.72 | 1.26 | 1.01 | 1.06 | 1.00 |
| TBP | SN147b69T_I18 | MK001519_1 | 1.06 | 1.05 | 0.91 | 1.00 | 1.16 | 1.17 | 0.83 | 0.78 | 0.87 | 0.69 | 0.93 |
| SDHA | SN032d28T_H08 | MK001905_1 | 0.50 | 0.59 | 0.49 | 0.59 | 0.59 | 0.61 | 0.88 | 1.06 | 0.95 | 0.95 | 0.96 |
| GUSB | SN102d12T_H04 | MK000279_1 | 1.73 | 0.95 | 1.82 | 1.89 | 1.75 | 1.65 | 1.15 | 1.63 | 1.32 | 1.55 | 1.36 |
| ACTB | SN263b46T_K12 | MK000668_2 | 1.80 | 2.00 | 2.19 | 2.61 | 2.45 | 2.46 | 0.31 | 0.36 | 0.38 | 0.42 | 0.40 |
| UBC | SN032d35T_F10 | MK005306_5 | 0.84 | 1.02 | 0.97 | 1.03 | 0.89 | 0.93 | 0.97 | 1.00 | 0.78 | 0.94 | 0.89 |
| B2M | SN252c26T_D07 | MK001845_10 | 3.00 | 1.20 | 1.38 | 1.10 | 0.70 | 0.83 | 0.44 | 0.47 | 0.51 | 0.43 | 0.64 |
| TFRC | SN252a02T_C01 | MK001530_1 | 1.68 | 3.17 | 3.24 | 3.13 | 2.40 | 2.55 | 0.71 | 0.70 | 0.70 | 0.66 | 0.79 |

TABLE 7 expression data of 14 genes in each tissue - (3)
[Cy5]

| | | | collected organ | | | | | | | | | |
|---|---|---|---|---|---|---|---|---|---|---|---|---|
| | | | pancreas | | | | | kidney | | | | |
| | | | | | | collected part | | | | | | |
| | | | — | | | | | cortex | | | | |
| | | | | | | | animal No. | | | | | |
| | | | 7 | 8 | 9 | 10 | 11 | 7 | 8 | 9 | 10 | 11 |
| | | | | | | | sample No. | | | | | |
| Symbol | EST | Sequence_ID | 29 | 52 | 75 | 98 | 121 | 31 | 54 | 77 | 100 | 123 |
| PAPSS2 | SN009c31T_N07 | MK002114_1 | 512 | 483 | 521 | 722 | 552 | 289 | 278 | 307 | 278 | 417 |
| EEF1G | SN117a11T_E03 | MK000784_2 | 13340 | 15561 | 11675 | 18748 | 17647 | 7291 | 9752 | 9422 | 8590 | 9694 |
| HPRT1 | SN020d53T_J14 | MK000286_1 | 737 | 672 | 797 | 725 | 691 | 601 | 682 | 735 | 634 | 558 |
| PPIA | SN021d41T_B12 | MK005336_3 | 1841 | 1994 | 1842 | 2191 | 2455 | 2850 | 3342 | 2592 | 3294 | 3381 |
| PGK1 | SN091c21T_J05 | MK000332_3 | 1142 | 797 | 746 | 916 | 1222 | 3991 | 3066 | 2473 | 2379 | 4310 |
| RPL4 | SN311b27T_E08 | MK000581_3 | 20245 | 25048 | 12916 | 38453 | 25829 | 9654 | 14037 | 10940 | 14629 | 13100 |
| GAPDH | SN299b55T_M14 | MK001057_3 | 1900 | 1712 | 1583 | 1701 | 1897 | 8997 | 12713 | 8188 | 8930 | 10133 |
| TBP | SN147b69T_I18 | MK001519_1 | 135 | 134 | 148 | 126 | 128 | 186 | 228 | 219 | 227 | 213 |
| SDHA | SN032d28T_H08 | MK001905_1 | 1270 | 1430 | 1067 | 1161 | 1446 | 3533 | 4389 | 5029 | 5114 | 4558 |
| GUSB | SN102d12T_H04 | MK000279_1 | 680 | 659 | 829 | 845 | 869 | 1014 | 1510 | 1493 | 1430 | 1491 |
| ACTB | SN263b46T_K12 | MK000668_2 | 11619 | 11506 | 12050 | 12790 | 10849 | 17901 | 27039 | 25596 | 22015 | 23241 |
| UBC | SN032d35T_F10 | MK005306_5 | 19495 | 17688 | 14874 | 16986 | 19872 | 21614 | 26024 | 28162 | 28853 | 24395 |
| B2M | SN252c26T_D07 | MK001845_10 | 15063 | 12647 | 11865 | 13567 | 13153 | 23191 | 27178 | 24443 | 20008 | 29526 |
| TFRC | SN252a02T_C01 | MK001530_1 | 1119 | 1294 | 1039 | 747 | 971 | 390 | 932 | 1109 | 978 | 710 |
| | | average | 2341 | 2283 | 2347 | 2166 | 2190 | 1839 | 2087 | 2002 | 2068 | 1947 |
| | | median | 464 | 465 | 465 | 465 | 464 | 464 | 465 | 466 | 468 | 469 |
| | | standard deviation | 15425 | 14143 | 14377 | 13353 | 13292 | 6724 | 7188 | 6942 | 6945 | 6769 |
| | | number of valid spots | 16211 | 16118 | 16109 | 16030 | 16006 | 16377 | 16304 | 16220 | 16272 | 16302 |

TABLE 7-continued expression data of 14 genes in each tissue - (3)
[Cy5]

| | | | \multicolumn{5}{c|}{collected organ: kidney, collected part: medulla} | \multicolumn{5}{c|}{collected organ: lung, collected part: left lung posterior lobe} |
|---|---|---|---|---|---|---|---|---|---|---|---|---|
| | | | \multicolumn{5}{c|}{animal No.} | \multicolumn{5}{c|}{animal No.} |
| | | | 7 | 8 | 9 | 10 | 11 | 7 | 8 | 9 | 10 | 11 |
| | | | \multicolumn{10}{c|}{sample No.} |
| Symbol | EST | Sequence_ID | 32 | 55 | 78 | 101 | 124 | 33 | 56 | 79 | 102 | 125 |
| PAPSS2 | SN009c31T_N07 | MK002114_1 | 235 | 280 | 275 | 292 | 322 | 2323 | 2152 | 2228 | 2117 | 3357 |
| EEF1G | SN117a11T_E03 | MK000784_2 | 5633 | 7146 | 7274 | 8210 | 7058 | 10609 | 10145 | 11194 | 9451 | 9935 |
| HPRT1 | SN020d53T_J14 | MK000286_1 | 524 | 577 | 569 | 511 | 509 | 531 | 626 | 581 | 549 | 509 |
| PPIA | SN021d41T_B12 | MK005336_3 | 2672 | 2589 | 2524 | 3627 | 2911 | 3582 | 3146 | 2968 | 3444 | 3746 |
| PGK1 | SN091c21T_J05 | MK000332_3 | 2952 | 2259 | 1921 | 2187 | 3384 | 2115 | 1396 | 1308 | 1344 | 2397 |
| RPL4 | SN311b27T_E08 | MK000581_3 | 7960 | 9841 | 9067 | 12813 | 10313 | 13501 | 14765 | 12460 | 16504 | 14333 |
| GAPDH | SN299b55T_M14 | MK001057_3 | 6506 | 8085 | 6254 | 7493 | 6664 | 4075 | 3866 | 4262 | 4139 | 4773 |
| TBP | SN147b69T_I18 | MK001519_1 | 163 | 156 | 192 | 190 | 191 | 250 | 227 | 241 | 234 | 305 |
| SDHA | SN032d28T_H08 | MK001905_1 | 3266 | 3694 | 3810 | 4596 | 3648 | 1677 | 1467 | 1517 | 1586 | 1661 |
| GUSB | SN102d12T_H04 | MK000279_1 | 854 | 1045 | 1223 | 1395 | 1150 | 1173 | 1574 | 1713 | 1513 | 1706 |
| ACTB | SN263b46T_K12 | MK000668_2 | 16499 | 22936 | 22586 | 23409 | 21013 | 40142 | 46462 | 43998 | 51571 | 50922 |
| UBC | SN032d35T_F10 | MK005306_5 | 21396 | 22906 | 23098 | 26527 | 22867 | 36007 | 32669 | 38343 | 35238 | 46250 |
| B2M | SN252c26T_D07 | MK001845_10 | 18466 | 20676 | 21276 | 20935 | 22582 | 73219 | 80563 | 84534 | 65528 | 96475 |
| TFRC | SN252a02T_C01 | MK001530_1 | 504 | 737 | 770 | 882 | 457 | 1323 | 1655 | 1538 | 1472 | 1820 |
| | | average | 1835 | 1898 | 1955 | 2158 | 1904 | 2045 | 2041 | 2087 | 1943 | 2108 |
| | | median | 468 | 467 | 467 | 468 | 467 | 468 | 469 | 470 | 470 | 471 |
| | | standard deviation | 6787 | 7024 | 6974 | 7842 | 6969 | 7850 | 7748 | 7691 | 7204 | 7838 |
| | | number of valid spots | 16268 | 16237 | 16256 | 16172 | 16185 | 16238 | 16253 | 16403 | 16281 | 16239 |

| | | | \multicolumn{5}{c|}{collected organ: heart, collected part: left ventricular wall} |
|---|---|---|---|---|---|---|---|
| | | | \multicolumn{5}{c|}{animal No.} |
| | | | 7 | 8 | 9 | 10 | 11 |
| | | | \multicolumn{5}{c|}{sample No.} |
| Symbol | EST | Sequence_ID | 34 | 57 | 80 | 103 | 126 |
| PAPSS2 | SN009c31T_N07 | MK002114_1 | 138 | 92 | 108 | 111 | 137 |
| EEF1G | SN117a11T_E03 | MK000784_2 | 6675 | 5668 | 5699 | 5947 | 6561 |
| HPRT1 | SN020d53T_J14 | MK000286_1 | 445 | 455 | 475 | 456 | 536 |
| PPIA | SN021d41T_B12 | MK005336_3 | 1534 | 1082 | 1162 | 1330 | 1681 |
| PGK1 | SN091c21T_J05 | MK000332_3 | 2471 | 1659 | 1811 | 1565 | 3284 |
| RPL4 | SN311b27T_E08 | MK000581_3 | 6064 | 5351 | 5196 | 6283 | 6376 |
| GAPDH | SN299b55T_M14 | MK001057_3 | 8371 | 10270 | 10242 | 9710 | 14285 |
| TBP | SN147b69T_I18 | MK001519_1 | 162 | 122 | 164 | 131 | 157 |
| SDHA | SN032d28T_H08 | MK001905_1 | 4821 | 4224 | 5308 | 4610 | 6231 |
| GUSB | SN102d12T_H04 | MK000279_1 | 441 | 341 | 454 | 378 | 547 |
| ACTB | SN263b46T_K12 | MK000668_2 | 7824 | 6718 | 8666 | 6918 | 10024 |
| UBC | SN032d35T_F10 | MK005306_5 | 31911 | 29285 | 35239 | 23629 | 35527 |
| B2M | SN252c26T_D07 | MK001845_10 | 21646 | 12730 | 14633 | 13756 | 14323 |
| TFRC | SN252a02T_C01 | MK001530_1 | 697 | 552 | 498 | 623 | 800 |
| | | average | 2172 | 1894 | 2150 | 2057 | 2090 |
| | | median | 471 | 470 | 470 | 470 | 471 |
| | | standard deviation | 8415 | 7394 | 8436 | 7739 | 7350 |
| | | number of valid spots | 16281 | 16155 | 16230 | 16323 | 16282 |

TABLE 8

| | | | [Cy3] | | | | | | | | | |
|---|---|---|---|---|---|---|---|---|---|---|---|---|
| | | | collected organ | | | | | | | | | |
| | | | pancreas | | | | | kidney | | | | |
| | | | collected part | | | | | | | | | |
| | | | — | | | | | cortex | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 29 | 52 | 75 | 98 | 121 | 31 | 54 | 77 | 100 | 123 |
| PAPSS2 | SN009c31T_N07 | MK002114_1 | 709 | 664 | 641 | 721 | 681 | 713 | 820 | 855 | 859 | 834 |
| EEF1G | SN117a11T_E03 | MK000784_2 | 10540 | 9969 | 10013 | 10578 | 10126 | 10940 | 12733 | 12985 | 13503 | 12035 |
| HPRT1 | SN020d53T_J14 | MK000286_1 | 1165 | 1209 | 1169 | 1186 | 1118 | 1230 | 1415 | 1410 | 1426 | 1232 |
| PPIA | SN021d41T_B12 | MK005336_3 | 3137 | 2936 | 3184 | 3076 | 3035 | 3098 | 3717 | 3851 | 3926 | 3588 |
| PGK1 | SN091c21T_J05 | MK000332_3 | 2370 | 2229 | 2417 | 2351 | 2218 | 2434 | 2894 | 2937 | 2884 | 2653 |
| RPL4 | SN311b27T_E08 | MK000581_3 | 13650 | 16148 | 17073 | 16312 | 16241 | 17544 | 20520 | 21027 | 20084 | 18259 |
| GAPDH | SN299b55T_M14 | MK001057_3 | 9400 | 9016 | 7943 | 9005 | 9129 | 9074 | 11172 | 11845 | 11713 | 11061 |
| TBP | SN147b69T_I18 | MK001519_1 | 212 | 218 | 227 | 218 | 210 | 224 | 271 | 270 | 266 | 238 |
| SDHA | SN032d28T_H08 | MK001905_1 | 3943 | 3622 | 2640 | 3267 | 3904 | 3340 | 4220 | 5037 | 5193 | 4644 |
| GUSB | SN102d12T_H04 | MK000279_1 | 1499 | 1444 | 1521 | 1565 | 1470 | 1524 | 1839 | 1820 | 1774 | 1681 |
| ACTB | SN263b46T_K12 | MK000668_2 | 36019 | 34895 | 38435 | 37701 | 35009 | 38205 | 41808 | 42743 | 42046 | 42180 |
| UBC | SN032d35T_F10 | MK005306_5 | 36491 | 37109 | 28948 | 35302 | 38111 | 33099 | 39095 | 44477 | 41946 | 38471 |
| B2M | SN252c26T_D07 | MK001845_10 | 58526 | 58511 | 52024 | 57838 | 59705 | 58398 | 64934 | 72289 | 66727 | 66241 |
| TFRC | SN252a02T_C01 | MK001530_1 | 1040 | 951 | 721 | 747 | 931 | 689 | 916 | 1090 | 1031 | 1068 |
| | | average | 2088 | 2061 | 2130 | 1973 | 1964 | 1961 | 2209 | 2156 | 2221 | 2055 |
| | | median | 495 | 495 | 496 | 495 | 495 | 495 | 496 | 497 | 499 | 500 |
| | | standard deviation | 8843 | 8380 | 9124 | 8175 | 8252 | 7272 | 7908 | 7593 | 7679 | 7245 |
| | | number of valid spots | 16211 | 16118 | 16109 | 16030 | 16006 | 16377 | 16304 | 16220 | 16272 | 16302 |

| | | | collected organ | | | | | | | | | |
|---|---|---|---|---|---|---|---|---|---|---|---|---|
| | | | kidney | | | | | lung | | | | |
| | | | collected part | | | | | | | | | |
| | | | medulla | | | | | left lung posterior lobe | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 32 | 55 | 78 | 101 | 124 | 33 | 56 | 79 | 102 | 125 |
| PAPSS2 | SN009c31T_N07 | MK002114_1 | 559 | 651 | 690 | 744 | 653 | 793 | 753 | 851 | 742 | 861 |
| EEF1G | SN117a11T_E03 | MK000784_2 | 8558 | 9515 | 9717 | 11142 | 10038 | 11203 | 10514 | 12195 | 10654 | 12197 |
| HPRT1 | SN020d53T_J14 | MK000286_1 | 986 | 1077 | 1084 | 1176 | 1072 | 1270 | 1224 | 1365 | 1200 | 1363 |
| PPIA | SN021d41T_B12 | MK005336_3 | 2899 | 2969 | 3444 | 3556 | 3216 | 3637 | 3301 | 3863 | 3237 | 3900 |
| PGK1 | SN091c21T_J05 | MK000332_3 | 1918 | 2052 | 2307 | 2439 | 2203 | 2451 | 2436 | 2648 | 2337 | 2792 |
| RPL4 | SN311b27T_E08 | MK000581_3 | 13710 | 14290 | 15988 | 16601 | 15274 | 17401 | 16361 | 18561 | 16183 | 19831 |
| GAPDH | SN299b55T_M14 | MK001057_3 | 7718 | 8725 | 8837 | 10486 | 8931 | 10473 | 9199 | 10805 | 9070 | 11436 |
| TBP | SN147b69T_I18 | MK001519_1 | 196 | 187 | 222 | 221 | 206 | 255 | 233 | 262 | 245 | 278 |
| SDHA | SN032d28T_H08 | MK001905_1 | 3493 | 3902 | 3849 | 4386 | 3940 | 4728 | 4179 | 4919 | 4477 | 5035 |
| GUSB | SN102d12T_H04 | MK000279_1 | 1225 | 1306 | 1464 | 1559 | 1416 | 1657 | 1546 | 1777 | 1525 | 1843 |
| ACTB | SN263b46T_K12 | MK000668_2 | 31709 | 33868 | 37267 | 39027 | 37315 | 34964 | 34295 | 37260 | 32277 | 39348 |
| UBC | SN032d35T_F10 | MK005306_5 | 32259 | 35064 | 35994 | 35362 | 37380 | 41465 | 36874 | 44805 | 33356 | 44720 |
| B2M | SN252c26T_D07 | MK001845_10 | 45815 | 49310 | 55725 | 58519 | 52994 | 40983 | 39992 | 44122 | 38444 | 40748 |
| TFRC | SN252a02T_C01 | MK001530_1 | 826 | 826 | 854 | 900 | 737 | 1171 | 1063 | 1251 | 1111 | 1213 |
| | | average | 1958 | 2016 | 2084 | 2389 | 2016 | 2623 | 2699 | 2915 | 2406 | 2895 |
| | | median | 499 | 498 | 499 | 499 | 498 | 499 | 500 | 501 | 501 | 502 |
| | | standard deviation | 7344 | 7701 | 7541 | 10460 | 7328 | 15531 | 17692 | 20637 | 13515 | 19580 |
| | | number of valid spots | 16268 | 16237 | 16256 | 16172 | 16185 | 16238 | 16253 | 16403 | 16281 | 16239 |

TABLE 8-continued

| | | | | [Cy3] | | | | | |
|---|---|---|---|---|---|---|---|---|---|
| | | | | | collected organ | | | | |
| | | | | | heart | | | | |
| | | | | | collected part | | | | |
| | | | | | left ventricular wall | | | | |
| | | | | | animal No. | | | | |
| | | | | | 7 | 8 | 9 | 10 | 11 |
| | | | | | sample No. | | | | |
| | Symbol | EST | Sequence_ID | | 34 | 57 | 80 | 103 | 126 |
| | PAPSS2 | SN009c31T_N07 | MK002114_1 | | 655 | 578 | 687 | 643 | 734 |
| | EEF1G | SN117a11T_E03 | MK000784_2 | | 9792 | 8811 | 9674 | 9361 | 11480 |
| | HPRT1 | SN020d53T_J14 | MK000286_1 | | 1032 | 935 | 1080 | 955 | 1221 |
| | PPIA | SN021d41T_B12 | MK005336_3 | | 3247 | 2739 | 3222 | 3146 | 3494 |
| | PGK1 | SN091c21T_J05 | MK000332_3 | | 2166 | 1911 | 2198 | 2009 | 2615 |
| | RPL4 | SN311b27T_E08 | MK000581_3 | | 14661 | 12664 | 14755 | 13327 | 18112 |
| | GAPDH | SN299b55T_M14 | MK001057_3 | | 9059 | 7462 | 9004 | 8846 | 10056 |
| | TBP | SN147b69T_I18 | MK001519_1 | | 208 | 167 | 213 | 186 | 234 |
| | SDHA | SN032d28T_H08 | MK001905_1 | | 3971 | 3331 | 3773 | 3566 | 4319 |
| | GUSB | SN102d12T_H04 | MK000279_1 | | 1307 | 1142 | 1338 | 1201 | 1612 |
| | ACTB | SN263b46T_K12 | MK000668_2 | | 38166 | 34135 | 38817 | 35879 | 43559 |
| | UBC | SN032d35T_F10 | MK005306_5 | | 36089 | 31778 | 32890 | 32865 | 37083 |
| | B2M | SN252c26T_D07 | MK001845_10 | | 52193 | 47279 | 53352 | 49431 | 57004 |
| | TFRC | SN252a02T_C01 | MK001530_1 | | 788 | 671 | 765 | 703 | 827 |
| | | | average | | 2380 | 2133 | 2398 | 2372 | 2508 |
| | | | median | | 502 | 501 | 501 | 501 | 502 |
| | | | standard deviation | | 10214 | 10102 | 10473 | 11317 | 12042 |
| | | | number of valid spots | | 16281 | 16155 | 16230 | 16323 | 16282 |

TABLE 9

| | | | [Ratio] | | | | | | | | | | |
|---|---|---|---|---|---|---|---|---|---|---|---|---|---|
| | | | organ collected | | | | | | | | | | |
| | | | pancreas | | | | | kidney | | | | | |
| | | | collected part | | | | | | | | | | |
| | | | — | | | | | cortex | | | | | |
| | | | animal No. | | | | | | | | | | |
| | | | 7 | 8 | 9 | 10 | 11 | 7 | 8 | 9 | 10 | 11 | |
| | | | sample No. | | | | | | | | | | |
| Symbol | EST | Sequence_ID | 29 | 52 | 75 | 98 | 121 | 31 | 54 | 77 | 100 | 123 | |
| PAPSS2 | SN009c31T_N07 | MK002114_1 | 0.72 | 0.73 | 0.81 | 1.00 | 0.81 | 0.40 | 0.34 | 0.36 | 0.32 | 0.50 | |
| EEF1G | SN117a11T_E03 | MK000784_2 | 1.27 | 1.56 | 1.17 | 1.77 | 1.74 | 0.67 | 0.77 | 0.73 | 0.64 | 0.81 | |
| HPRT1 | SN020d53T_J14 | MK000286_1 | 0.63 | 0.56 | 0.68 | 0.61 | 0.62 | 0.49 | 0.48 | 0.52 | 0.44 | 0.45 | |
| PPIA | SN021d41T_B12 | MK005336_3 | 0.59 | 0.68 | 0.58 | 0.71 | 0.81 | 0.92 | 0.90 | 0.67 | 0.84 | 0.94 | |
| PGK1 | SN091c21T_J05 | MK000332_3 | 0.48 | 0.36 | 0.31 | 0.39 | 0.55 | 1.64 | 1.06 | 0.84 | 0.82 | 1.62 | |
| RPL4 | SN311b27T_E08 | MK000581_3 | 1.48 | 1.55 | 0.76 | 2.36 | 1.59 | 0.55 | 0.68 | 0.52 | 0.73 | 0.72 | |
| GAPDH | SN299b55T_M14 | MK001057_3 | 0.20 | 0.19 | 0.20 | 0.19 | 0.21 | 0.99 | 1.14 | 0.69 | 0.76 | 0.92 | |
| TBP | SN147b69T_I18 | MK001519_1 | 0.64 | 0.61 | 0.65 | 0.58 | 0.61 | 0.83 | 0.84 | 0.81 | 0.85 | 0.90 | |
| SDHA | SN032d28T_H08 | MK001905_1 | 0.32 | 0.39 | 0.40 | 0.36 | 0.37 | 1.06 | 1.04 | 1.00 | 0.98 | 0.98 | |
| GUSB | SN102d12T_H04 | MK000279_1 | 0.45 | 0.46 | 0.55 | 0.54 | 0.59 | 0.67 | 0.82 | 0.82 | 0.81 | 0.89 | |
| ACTB | SN263b46T_K12 | MK000668_2 | 0.32 | 0.33 | 0.31 | 0.34 | 0.31 | 0.47 | 0.65 | 0.60 | 0.52 | 0.55 | |
| UBC | SN032d35T_F10 | MK005306_5 | 0.53 | 0.48 | 0.51 | 0.48 | 0.52 | 0.65 | 0.67 | 0.63 | 0.69 | 0.63 | |
| B2M | SN252c26T_D07 | MK001845_10 | 0.26 | 0.22 | 0.23 | 0.23 | 0.22 | 0.40 | 0.42 | 0.34 | 0.30 | 0.45 | |
| TFRC | SN252a02T_C01 | MK001530_1 | 1.08 | 1.36 | 1.44 | 1.00 | 1.04 | 0.57 | 1.02 | 1.02 | 0.95 | 0.66 | |

TABLE 9-continued

[Ratio]

| | | | organ collected | | | | | | | | |
|---|---|---|---|---|---|---|---|---|---|---|---|
| | | | kidney | | | | | lung | | | |
| | | | collected part | | | | | | | | |
| | | | medulla | | | | | left lung posterior lobe | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 32 | 55 | 78 | 101 | 124 | 33 | 56 | 79 | 102 | 125 |
| PAPSS2 | SN009c31T_N07 | MK002114_1 | 0.42 | 0.43 | 0.40 | 0.39 | 0.49 | 2.93 | 2.86 | 2.62 | 2.85 | 3.90 |
| EEF1G | SN117a11T_E03 | MK000784_2 | 0.66 | 0.75 | 0.75 | 0.74 | 0.70 | 0.95 | 0.96 | 0.92 | 0.89 | 0.81 |
| HPRT1 | SN020d53T_J14 | MK000286_1 | 0.53 | 0.54 | 0.52 | 0.43 | 0.47 | 0.42 | 0.51 | 0.43 | 0.46 | 0.37 |
| PPIA | SN021d41T_B12 | MK005336_3 | 0.92 | 0.87 | 0.73 | 1.02 | 0.90 | 0.99 | 0.95 | 0.77 | 1.06 | 0.96 |
| PGK1 | SN091c21T_J05 | MK000332_3 | 1.54 | 1.10 | 0.83 | 0.90 | 1.54 | 0.86 | 0.57 | 0.49 | 0.58 | 0.86 |
| RPL4 | SN311b27T_E08 | MK000581_3 | 0.58 | 0.69 | 0.57 | 0.77 | 0.68 | 0.78 | 0.90 | 0.67 | 1.02 | 0.72 |
| GAPDH | SN299b55T_M14 | MK001057_3 | 0.84 | 0.93 | 0.71 | 0.71 | 0.75 | 0.39 | 0.42 | 0.39 | 0.46 | 0.42 |
| TBP | SN147b69T_I18 | MK001519_1 | 0.83 | 0.84 | 0.87 | 0.86 | 0.93 | 0.98 | 0.98 | 0.92 | 0.96 | 1.10 |
| SDHA | SN032d28T_H08 | MK001905_1 | 0.93 | 0.95 | 0.99 | 1.05 | 0.93 | 0.35 | 0.35 | 0.31 | 0.35 | 0.33 |
| GUSB | SN102d12T_H04 | MK000279_1 | 0.70 | 0.80 | 0.84 | 0.90 | 0.81 | 0.71 | 1.02 | 0.96 | 0.99 | 0.93 |
| ACTB | SN263b46T_K12 | MK000668_2 | 0.52 | 0.68 | 0.61 | 0.60 | 0.56 | 1.15 | 1.35 | 1.18 | 1.60 | 1.29 |
| UBC | SN032d35T_F10 | MK005306_5 | 0.66 | 0.65 | 0.64 | 0.75 | 0.61 | 0.87 | 0.89 | 0.86 | 1.06 | 1.03 |
| B2M | SN252c26T_D07 | MK001845_10 | 0.40 | 0.42 | 0.38 | 0.36 | 0.43 | 1.79 | 2.01 | 1.92 | 1.70 | 2.37 |
| TFRC | SN252a02T_C01 | MK001530_1 | 0.61 | 0.89 | 0.90 | 0.98 | 0.62 | 1.13 | 1.56 | 1.23 | 1.33 | 1.50 |

| | | | collected organ | | | | |
|---|---|---|---|---|---|---|---|
| | | | heart | | | | |
| | | | collected part | | | | |
| | | | left ventricular wall | | | | |
| | | | animal No. | | | | |
| | | | 7 | 8 | 9 | 10 | 11 |
| | | | sample No. | | | | |
| Symbol | EST | Sequence_ID | 34 | 57 | 80 | 103 | 126 |
| PAPSS2 | SN009c31T_N07 | MK002114_1 | 0.21 | 0.16 | 0.16 | 0.17 | 0.19 |
| EEF1G | SN117a11T_E03 | MK000784_2 | 0.68 | 0.64 | 0.59 | 0.64 | 0.57 |
| HPRT1 | SN020d53T_J14 | MK000286_1 | 0.43 | 0.49 | 0.44 | 0.48 | 0.44 |
| PPIA | SN021d41T_B12 | MK005336_3 | 0.47 | 0.40 | 0.36 | 0.42 | 0.48 |
| PGK1 | SN091c21T_J05 | MK000332_3 | 1.14 | 0.87 | 0.82 | 0.78 | 1.26 |
| RPL4 | SN311b27T_E08 | MK000581_3 | 0.41 | 0.42 | 0.35 | 0.47 | 0.35 |
| GAPDH | SN299b55T_M14 | MK001057_3 | 0.92 | 1.38 | 1.14 | 1.10 | 1.42 |
| TBP | SN147b69T_I18 | MK001519_1 | 0.78 | 0.73 | 0.77 | 0.70 | 0.67 |
| SDHA | SN032d28T_H08 | MK001905_1 | 1.21 | 1.27 | 1.41 | 1.29 | 1.44 |
| GUSB | SN102d12T_H04 | MK000279_1 | 0.34 | 0.30 | 0.34 | 0.32 | 0.34 |
| ACTB | SN263b46T_K12 | MK000668_2 | 0.20 | 0.20 | 0.22 | 0.19 | 0.23 |
| UBC | SN032d35T_F10 | MK005306_5 | 0.88 | 0.92 | 1.07 | 0.72 | 0.96 |
| B2M | SN252c26T_D07 | MK001845_10 | 0.41 | 0.27 | 0.27 | 0.28 | 0.25 |
| TFRC | SN252a02T_C01 | MK001530_1 | 0.88 | 0.82 | 0.65 | 0.89 | 0.97 |

TABLE 10 expression data of 14 genes in each tissue - (4)
[Cy5]

| | | | collected organ | | | | | | | | |
|---|---|---|---|---|---|---|---|---|---|---|---|
| | | | heart | | | | | spleen | | | |
| | | | collected part | | | | | | | | |
| | | | septum | | | | | — | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 35 | 58 | 81 | 104 | 127 | 36 | 59 | 82 | 105 | 128 |
| PAPSS2 | SN009c31T_N07 | MK002114_1 | 258 | 142 | 114 | 133 | 142 | 216 | 248 | 234 | 276 | 321 |
| EEF1G | SN117a11T_E03 | MK000784_2 | 8063 | 7131 | 6792 | 6469 | 6021 | 17788 | 22711 | 16750 | 16685 | 18581 |
| HPRT1 | SN020d53T_J14 | MK000286_1 | 402 | 461 | 410 | 481 | 460 | 734 | 745 | 639 | 860 | 906 |

TABLE 10-continued expression data of 14 genes in each tissue - (4)
[Cy5]

| Symbol | EST | Sequence_ID | | | | | | | | | |
|---|---|---|---|---|---|---|---|---|---|---|---|
| PPIA | SN021d41T_B12 | MK005336_3 | 2143 | 1496 | 1224 | 1726 | 1413 | 5127 | 7640 | 3705 | 5858 | 7025 |
| PGK1 | SN091c21T_J05 | MK000332_3 | 2880 | 1904 | 1863 | 1819 | 2879 | 2930 | 2450 | 1815 | 2060 | 4192 |
| RPL4 | SN311b27T_E08 | MK000581_3 | 8179 | 6451 | 5580 | 8120 | 5460 | 28357 | 37829 | 22656 | 29202 | 27405 |
| GAPDH | SN299b55T_M14 | MK001057_3 | 8166 | 10795 | 10702 | 10690 | 12660 | 5294 | 7129 | 4676 | 5791 | 8552 |
| TBP | SN147b69T_I18 | MK001519_1 | 171 | 129 | 138 | 165 | 137 | 310 | 282 | 262 | 320 | 436 |
| SDHA | SN032d28T_H08 | MK001905_1 | 4918 | 4628 | 5921 | 5258 | 5354 | 1864 | 2080 | 1417 | 2093 | 2198 |
| GUSB | SN102d12T_H04 | MK000279_1 | 711 | 495 | 480 | 535 | 451 | 1555 | 2449 | 2004 | 2495 | 3066 |
| ACTB | SN263b46T_K12 | MK000668_2 | 19600 | 11206 | 10366 | 11050 | 9452 | 59256 | 103226 | 59770 | 67521 | 84754 |
| UBC | SN032d35T_F10 | MK005306_5 | 26655 | 30406 | 40533 | 32032 | 37124 | 26711 | 35523 | 26533 | 32268 | 30880 |
| B2M | SN252c26T_D07 | MK001845_10 | 23091 | 17364 | 17289 | 13851 | 17214 | 79488 | 121574 | 73169 | 87381 | 106948 |
| TFRC | SN252a02T_C01 | MK001530_1 | 579 | 736 | 589 | 785 | 715 | 940 | 1392 | 1091 | 1518 | 1817 |
| | | average | 1994 | 1939 | 1988 | 2283 | 2015 | 1841 | 1912 | 1793 | 2069 | 2222 |
| | | median | 470 | 469 | 469 | 470 | 469 | 470 | 470 | 470 | 471 | 473 |
| | | standard deviation | 7552 | 6945 | 7658 | 8561 | 7864 | 6515 | 6602 | 6888 | 6953 | 7768 |
| | | number of valid spots | 16284 | 16278 | 16187 | 16225 | 16169 | 16366 | 16227 | 16311 | 16407 | 16301 |

| | | | collected organ | | | | | | | | | |
|---|---|---|---|---|---|---|---|---|---|---|---|---|
| | | | thymus | | | | | testis | | | | |
| | | | collected part | | | | | | | | | |
| | | | — | | | | | — | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 37 | 60 | 83 | 106 | 129 | 38 | 61 | 84 | 107 | 130 |
| PAPSS2 | SN009c31T_N07 | MK002114_1 | 139 | 246 | 216 | 117 | 123 | 812 | 692 | 616 | 746 | 702 |
| EEF1G | SN117a11T_E03 | MK000784_2 | 17487 | 18694 | 18485 | 13101 | 16530 | 8064 | 7175 | 7007 | 6674 | 6440 |
| HPRT1 | SN020d53T_J14 | MK000286_1 | 769 | 868 | 745 | 815 | 877 | 3101 | 4127 | 2268 | 3491 | 2892 |
| PPIA | SN021d41T_B12 | MK005336_3 | 6097 | 7555 | 5226 | 6428 | 6939 | 3061 | 2941 | 2042 | 2695 | 2179 |
| PGK1 | SN091c21T_J05 | MK000332_3 | 3941 | 3154 | 2629 | 2561 | 4320 | 2743 | 1137 | 963 | 1243 | 1926 |
| RPL4 | SN311b27T_E08 | MK000581_3 | 25364 | 35169 | 23856 | 23896 | 26104 | 12954 | 13423 | 10514 | 11705 | 11008 |
| GAPDH | SN299b55T_M14 | MK001057_3 | 7875 | 9185 | 8180 | 8642 | 8156 | 5312 | 5556 | 3963 | 4810 | 4002 |
| TBP | SN147b69T_I18 | MK001519_1 | 340 | 349 | 342 | 305 | 436 | 325 | 301 | 263 | 273 | 290 |
| SDHA | SN032d28T_H08 | MK001905_1 | 1859 | 2342 | 1563 | 1859 | 2068 | 2403 | 2276 | 1545 | 1876 | 1773 |
| GUSB | SN102d12T_H04 | MK000279_1 | 1630 | 2320 | 2313 | 2102 | 2418 | 2166 | 2048 | 3407 | 1566 | 2454 |
| ACTB | SN263b46T_K12 | MK000668_2 | 47770 | 61136 | 57847 | 54038 | 53552 | 27926 | 30591 | 21666 | 26684 | 22792 |
| UBC | SN032d35T_F10 | MK005306_5 | 25764 | 31418 | 28568 | 23731 | 23127 | 27468 | 34521 | 32525 | 28308 | 25553 |
| B2M | SN252c26T_D07 | MK001845_10 | 47501 | 51426 | 49746 | 48774 | 59823 | 17172 | 15501 | 10026 | 10811 | 11732 |
| TFRC | SN252a02T_C01 | MK001530_1 | 1963 | 2162 | 2139 | 1934 | 2057 | 1052 | 1455 | 1103 | 938 | 980 |
| | | average | 1822 | 2074 | 1929 | 2085 | 1960 | 1943 | 1976 | 1942 | 1897 | 1877 |
| | | median | 473 | 474 | 474 | 475 | 475 | 475 | 475 | 474 | 474 | 474 |
| | | standard deviation | 7623 | 7999 | 8070 | 9796 | 9345 | 8904 | 8130 | 8887 | 7710 | 8472 |
| | | number of valid spots | 16296 | 16335 | 16269 | 16219 | 16231 | 16223 | 16262 | 16262 | 16308 | 16283 |

| | | | collected organ | | | | |
|---|---|---|---|---|---|---|---|
| | | | prostate | | | | |
| | | | collected part | | | | |
| | | | — | | | | |
| | | | animal No. | | | | |
| | | | 7 | 8 | 9 | 10 | 11 |
| | | | sample No. | | | | |
| | Symbol | EST | Sequence_ID | 39 | 62 | 85 | 108 | 131 |
| | PAPSS2 | SN009c31T_N07 | MK002114_1 | 1776 | 1251 | 1510 | 1500 | 1408 |
| | EEF1G | SN117a11T_E03 | MK000784_2 | 15966 | 19569 | 16995 | 16354 | 14467 |
| | HPRT1 | SN020d53T_J14 | MK000286_1 | 561 | 497 | 443 | 527 | 399 |
| | PPIA | SN021d41T_B12 | MK005336_3 | 3954 | 6342 | 3064 | 5281 | 3069 |
| | PGK1 | SN091c21T_J05 | MK000332_3 | 3750 | 2072 | 1654 | 2730 | 2550 |
| | RPL4 | SN311b27T_E08 | MK000581_3 | 21019 | 24233 | 20210 | 24903 | 20889 |
| | GAPDH | SN299b55T_M14 | MK001057_3 | 8900 | 10150 | 5871 | 9414 | 7029 |
| | TBP | SN147b69T_I18 | MK001519_1 | 291 | 250 | 261 | 299 | 313 |
| | SDHA | SN032d28T_H08 | MK001905_1 | 2083 | 1639 | 1555 | 1784 | 1846 |
| | GUSB | SN102d12T_H04 | MK000279_1 | 1330 | 1655 | 1640 | 1537 | 1731 |
| | ACTB | SN263b46T_K12 | MK000668_2 | 51537 | 58789 | 41060 | 57256 | 40102 |
| | UBC | SN032d35T_F10 | MK005306_5 | 36050 | 29386 | 21987 | 26678 | 34688 |
| | B2M | SN252c26T_D07 | MK001845_10 | 35021 | 39276 | 22376 | 20179 | 38310 |
| | TFRC | SN252a02T_C01 | MK001530_1 | 1388 | 812 | 775 | 1714 | 1003 |

TABLE 10-continued expression data of 14 genes in each tissue - (4)

[Cy5]

| | | | | | |
|---|---|---|---|---|---|
| average | 2106 | 1961 | 1980 | 1993 | 2016 |
| median | 475 | 475 | 475 | 475 | 476 |
| standard deviation | 7290 | 7428 | 8641 | 7468 | 8130 |
| number of valid spots | 16349 | 16227 | 16233 | 16307 | 16168 |

TABLE 11

[Cy3]

| | | | collected organ | | | | | | | | |
|---|---|---|---|---|---|---|---|---|---|---|---|
| | | | heart | | | | | spleen | | | |
| | | | collected part | | | | | | | | |
| | | | septum | | | | | — | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 35 | 58 | 81 | 104 | 127 | 36 | 59 | 82 | 105 | 128 |
| PAPSS2 | SN009c31T_N07 | MK002114_1 | 701 | 684 | 648 | 760 | 682 | 771 | 842 | 723 | 833 | 943 |
| EEF1G | SN117a11T_E03 | MK000784_2 | 10315 | 10106 | 10064 | 10659 | 9983 | 10725 | 11761 | 10992 | 12324 | 13750 |
| HPRT1 | SN020d53T_J14 | MK000286_1 | 1089 | 1041 | 1049 | 1144 | 998 | 1220 | 1316 | 1242 | 1310 | 1510 |
| PPIA | SN021d41T_B12 | MK005336_3 | 3650 | 3380 | 3142 | 3805 | 3143 | 3489 | 3686 | 3297 | 3801 | 4132 |
| PGK1 | SN091c21T_J05 | MK000332_3 | 2362 | 2245 | 2149 | 2611 | 2185 | 2486 | 2713 | 2445 | 2797 | 3222 |
| RPL4 | SN311b27T_E08 | MK000581_3 | 15903 | 13077 | 14694 | 16649 | 14417 | 16385 | 16650 | 17576 | 15076 | 21781 |
| GAPDH | SN299b55T_M14 | MK001057_3 | 9529 | 9240 | 9129 | 9708 | 9288 | 10241 | 11611 | 9503 | 11085 | 12272 |
| TBP | SN147b69T_I18 | MK001519_1 | 207 | 195 | 188 | 227 | 183 | 264 | 263 | 231 | 288 | 311 |
| SDHA | SN032d28T_H08 | MK001905_1 | 4022 | 3759 | 3874 | 4546 | 3995 | 4260 | 4768 | 3918 | 4856 | 5502 |
| GUSB | SN102d12T_H04 | MK000279_1 | 1497 | 1329 | 1297 | 1549 | 1259 | 1666 | 1807 | 1586 | 1800 | 2168 |
| ACTB | SN263b46T_K12 | MK000668_2 | 38543 | 35817 | 37585 | 44535 | 37465 | 30240 | 28467 | 30525 | 33122 | 36777 |
| UBC | SN032d35T_F10 | MK005306_5 | 33186 | 33172 | 34984 | 35802 | 33107 | 37145 | 35007 | 38993 | 41810 | 45292 |
| B2M | SN252c26T_D07 | MK001845_10 | 54963 | 47987 | 51966 | 68547 | 51107 | 40745 | 38435 | 41656 | 43735 | 49025 |
| TFRC | SN252a02T_C01 | MK001530_1 | 776 | 788 | 805 | 817 | 812 | 984 | 1038 | 886 | 1254 | 1302 |
| | | average | 2115 | 2110 | 2193 | 2401 | 2169 | 2283 | 2405 | 2407 | 2549 | 2993 |
| | | median | 501 | 500 | 500 | 501 | 500 | 501 | 501 | 501 | 503 | 505 |
| | | standard deviation | 8252 | 8434 | 9458 | 9237 | 9091 | 11921 | 13915 | 15384 | 12917 | 18265 |
| | | number of valid spots | 16284 | 16278 | 16187 | 16225 | 16169 | 16366 | 16227 | 16311 | 16407 | 16301 |

| | | | collected organ | | | | | | | | |
|---|---|---|---|---|---|---|---|---|---|---|---|
| | | | thymus | | | | | testis | | | |
| | | | collected part | | | | | | | | |
| | | | — | | | | | — | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 37 | 60 | 83 | 106 | 129 | 38 | 61 | 84 | 107 | 130 |
| PAPSS2 | SN009c31T_N07 | MK002114_1 | 775 | 904 | 895 | 771 | 803 | 761 | 731 | 727 | 686 | 698 |
| EEF1G | SN117a11T_E03 | MK000784_2 | 11220 | 12644 | 12392 | 11453 | 11729 | 11069 | 11272 | 10850 | 10650 | 10242 |
| HPRT1 | SN020d53T_J14 | MK000286_1 | 1206 | 1410 | 1364 | 1198 | 1337 | 1166 | 1117 | 1074 | 1058 | 1085 |
| PPIA | SN021d41T_B12 | MK005336_3 | 3513 | 3916 | 3964 | 3506 | 3457 | 3543 | 3523 | 3335 | 3322 | 3291 |
| PGK1 | SN091c21T_J05 | MK000332_3 | 2539 | 2909 | 2909 | 2615 | 2764 | 2535 | 2336 | 2288 | 2284 | 2239 |
| RPL4 | SN311b27T_E08 | MK000581_3 | 16124 | 19182 | 18857 | 16220 | 18384 | 17037 | 17208 | 16438 | 14795 | 15416 |
| GAPDH | SN299b55T_M14 | MK001057_3 | 10208 | 11738 | 11583 | 10623 | 10560 | 10254 | 9779 | 9807 | 9541 | 9599 |
| TBP | SN147b69T_I18 | MK001519_1 | 250 | 281 | 259 | 241 | 261 | 236 | 229 | 211 | 216 | 211 |
| SDHA | SN032d28T_H08 | MK001905_1 | 4365 | 5014 | 4879 | 4304 | 4952 | 4220 | 4486 | 4233 | 3845 | 3873 |
| GUSB | SN102d12T_H04 | MK000279_1 | 1689 | 1973 | 1902 | 1713 | 1899 | 1663 | 1542 | 1489 | 1453 | 1451 |
| ACTB | SN263b46T_K12 | MK000668_2 | 34732 | 38250 | 37723 | 35352 | 36021 | 39580 | 37504 | 37513 | 34823 | 36470 |
| UBC | SN032d35T_F10 | MK005306_5 | 38954 | 42833 | 41747 | 40687 | 41982 | 37876 | 40141 | 40216 | 36891 | 35569 |
| B2M | SN252c26T_D07 | MK001845_10 | 68426 | 61241 | 51224 | 56639 | 78599 | 72649 | 69465 | 59950 | 58090 | 57978 |
| TFRC | SN252a02T_C01 | MK001530_1 | 1020 | 1101 | 1111 | 1041 | 1207 | 1071 | 1038 | 939 | 838 | 890 |

TABLE 11-continued

| | | | [Cy3] | | | | | | | | |
|---|---|---|---|---|---|---|---|---|---|---|---|
| | | average | 2282 | 2230 | 2369 | 2140 | 2548 | 2038 | 2073 | 2050 | 1985 | 1965 |
| | | median | 505 | 506 | 507 | 507 | 507 | 507 | 508 | 507 | 508 | 508 |
| | | standard deviation | 12883 | 8781 | 12949 | 8595 | 16580 | 7965 | 7554 | 8196 | 7211 | 7537 |
| | | number of valid spots | 16296 | 16335 | 16269 | 16219 | 16231 | 16223 | 16262 | 16262 | 16308 | 16283 |

| | | | | collected organ prostate collected part — | | | | |
|---|---|---|---|---|---|---|---|---|
| | | | | | | animal No. | | |
| | | | | 7 | 8 | 9 | 10 | 11 |
| | | | | | | sample No. | | |
| Symbol | EST | Sequence_ID | | 39 | 62 | 85 | 108 | 131 |
| PAPSS2 | SN009c31T_N07 | MK002114_1 | | 799 | 799 | 789 | 800 | 860 |
| EEF1G | SN117a11T_E03 | MK000784_2 | | 10958 | 10909 | 11190 | 11466 | 11776 |
| HPRT1 | SN020d53T_J14 | MK000286_1 | | 1279 | 1176 | 1249 | 1206 | 1261 |
| PPIA | SN021d41T_B12 | MK005336_3 | | 3652 | 3651 | 3691 | 3780 | 3995 |
| PGK1 | SN091c21T_J05 | MK000332_3 | | 2547 | 2491 | 2559 | 2655 | 2736 |
| RPL4 | SN311b27T_E08 | MK000581_3 | | 16770 | 16220 | 16934 | 16754 | 17340 |
| GAPDH | SN299b55T_M14 | MK001057_3 | | 10549 | 10572 | 10935 | 10835 | 11268 |
| TBP | SN147b69T_I18 | MK001519_1 | | 252 | 233 | 236 | 242 | 251 |
| SDHA | SN032d28T_H08 | MK001905_1 | | 4581 | 4391 | 4514 | 4566 | 4756 |
| GUSB | SN102d12T_H04 | MK000279_1 | | 1648 | 1618 | 1654 | 1742 | 1787 |
| ACTB | SN263b46T_K12 | MK000668_2 | | 33150 | 32773 | 37154 | 33523 | 38295 |
| UBC | SN032d35T_F10 | MK005306_5 | | 39688 | 40139 | 40885 | 40913 | 41230 |
| B2M | SN252c26T_D07 | MK001845_10 | | 57419 | 56731 | 67173 | 60386 | 87480 |
| TFRC | SN252a02T_C01 | MK001530_1 | | 1125 | 998 | 1039 | 979 | 1065 |
| | | average | | 2384 | 2288 | 2264 | 2292 | 2316 |
| | | median | | 508 | 509 | 509 | 509 | 509 |
| | | standard deviation | | 10177 | 11267 | 10565 | 10282 | 11321 |
| | | number of valid spots | | 16349 | 16227 | 16233 | 16307 | 16168 |

TABLE 12

| | | | [Ratio] | | | | | | | | | |
|---|---|---|---|---|---|---|---|---|---|---|---|---|
| | | | collected organ | | | | | | | | | |
| | | | heart | | | | | spleen | | | | |
| | | | collected part | | | | | | | | | |
| | | | septum | | | | | — | | | | |
| | | | animal No. | | | | | | | | | |
| | | | 7 | 8 | 9 | 10 | 11 | 7 | 8 | 9 | 10 | 11 |
| | | | sample No. | | | | | | | | | |
| Symbol | EST | Sequence_ID | 35 | 58 | 81 | 104 | 127 | 36 | 59 | 82 | 105 | 128 |
| PAPSS2 | SN009c31T_N07 | MK002114_1 | 0.37 | 0.21 | 0.18 | 0.17 | 0.21 | 0.28 | 0.29 | 0.32 | 0.33 | 0.34 |
| EEF1G | SN117a11T_E03 | MK000784_2 | 0.78 | 0.71 | 0.67 | 0.61 | 0.60 | 1.66 | 1.93 | 1.52 | 1.35 | 1.35 |
| HPRT1 | SN020d53T_J14 | MK000286_1 | 0.37 | 0.44 | 0.39 | 0.42 | 0.46 | 0.60 | 0.57 | 0.51 | 0.66 | 0.60 |
| PPIA | SN021d41T_B12 | MK005336_3 | 0.59 | 0.44 | 0.39 | 0.45 | 0.45 | 1.47 | 2.07 | 1.12 | 1.54 | 1.70 |
| PGK1 | SN091c21T_J05 | MK000332_3 | 1.22 | 0.85 | 0.87 | 0.70 | 1.32 | 1.18 | 0.90 | 0.74 | 0.74 | 1.30 |
| RPL4 | SN311b27T_E08 | MK000581_3 | 0.51 | 0.49 | 0.38 | 0.49 | 0.38 | 1.73 | 2.27 | 1.29 | 1.94 | 1.26 |
| GAPDH | SN299b55T_M14 | MK001057_3 | 0.86 | 1.17 | 1.17 | 1.10 | 1.36 | 0.52 | 0.61 | 0.49 | 0.52 | 0.70 |
| TBP | SN147b69T_I18 | MK001519_1 | 0.83 | 0.66 | 0.73 | 0.73 | 0.75 | 1.17 | 1.07 | 1.14 | 1.11 | 1.40 |
| SDHA | SN032d28T_H08 | MK001905_1 | 1.22 | 1.23 | 1.53 | 1.16 | 1.34 | 0.44 | 0.44 | 0.36 | 0.43 | 0.40 |
| GUSB | SN102d12T_H04 | MK000279_1 | 0.47 | 0.37 | 0.37 | 0.35 | 0.36 | 0.93 | 1.36 | 1.26 | 1.39 | 1.41 |
| ACTB | SN263b46T_K12 | MK000668_2 | 0.51 | 0.31 | 0.28 | 0.25 | 0.25 | 1.96 | 3.63 | 1.96 | 2.04 | 2.30 |
| UBC | SN032d35T_F10 | MK005306_5 | 0.80 | 0.92 | 1.16 | 0.89 | 1.12 | 0.72 | 1.01 | 0.68 | 0.77 | 0.68 |
| B2M | SN252c26T_D07 | MK001845_10 | 0.42 | 0.36 | 0.33 | 0.20 | 0.34 | 1.95 | 3.16 | 1.76 | 2.00 | 2.18 |
| TFRC | SN252a02T_C01 | MK001530_1 | 0.75 | 0.93 | 0.73 | 0.96 | 0.88 | 0.96 | 1.34 | 1.23 | 1.21 | 1.40 |

TABLE 12-continued

[Ratio]

| | | | collected organ | | | | | | | | |
|---|---|---|---|---|---|---|---|---|---|---|---|
| | | | thymus | | | | | testis | | | |
| | | | collected part | | | | | | | | |
| | | | — | | | | | — | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 37 | 60 | 83 | 106 | 129 | 38 | 61 | 84 | 107 | 130 |
| PAPSS2 | SN009c31T_N07 | MK002114_1 | 0.18 | 0.27 | 0.24 | 0.15 | 0.15 | 1.07 | 0.95 | 0.85 | 1.09 | 1.01 |
| EEF1G | SN117a11T_E03 | MK000784_2 | 1.56 | 1.48 | 1.49 | 1.14 | 1.41 | 0.73 | 0.64 | 0.65 | 0.63 | 0.63 |
| HPRT1 | SN020d53T_J14 | MK000286_1 | 0.64 | 0.62 | 0.55 | 0.68 | 0.66 | 2.66 | 3.69 | 2.11 | 3.30 | 2.67 |
| PPIA | SN021d41T_B12 | MK005336_3 | 1.74 | 1.93 | 1.32 | 1.83 | 2.01 | 0.86 | 0.83 | 0.61 | 0.81 | 0.66 |
| PGK1 | SN091c21T_J05 | MK000332_3 | 1.55 | 1.08 | 0.90 | 0.98 | 1.56 | 1.08 | 0.49 | 0.42 | 0.54 | 0.86 |
| RPL4 | SN311b27T_E08 | MK000581_3 | 1.57 | 1.83 | 1.27 | 1.47 | 1.42 | 0.76 | 0.78 | 0.64 | 0.79 | 0.71 |
| GAPDH | SN299b55T_M14 | MK001057_3 | 0.77 | 0.78 | 0.71 | 0.81 | 0.77 | 0.52 | 0.57 | 0.40 | 0.50 | 0.42 |
| TBP | SN147b69T_I18 | MK001519_1 | 1.36 | 1.24 | 1.32 | 1.26 | 1.67 | 1.38 | 1.31 | 1.24 | 1.26 | 1.37 |
| SDHA | SN032d28T_H08 | MK001905_1 | 0.43 | 0.47 | 0.32 | 0.43 | 0.42 | 0.57 | 0.51 | 0.36 | 0.49 | 0.46 |
| GUSB | SN102d12T_H04 | MK000279_1 | 0.96 | 1.18 | 1.22 | 1.23 | 1.27 | 1.30 | 1.33 | 2.29 | 1.08 | 1.69 |
| ACTB | SN263b46T_K12 | MK000668_2 | 1.38 | 1.60 | 1.53 | 1.53 | 1.49 | 0.71 | 0.82 | 0.58 | 0.77 | 0.62 |
| UBC | SN032d35T_F10 | MK005306_5 | 0.66 | 0.73 | 0.68 | 0.58 | 0.55 | 0.73 | 0.86 | 0.81 | 0.77 | 0.72 |
| B2M | SN252c26T_D07 | MK001845_10 | 0.69 | 0.84 | 0.97 | 0.86 | 0.76 | 0.24 | 0.22 | 0.17 | 0.19 | 0.20 |
| TFRC | SN252a02T_C01 | MK001530_1 | 1.92 | 1.96 | 1.93 | 1.86 | 1.70 | 0.98 | 1.40 | 1.18 | 1.12 | 1.10 |

| | | | collected organ | | | | |
|---|---|---|---|---|---|---|---|
| | | | prostate | | | | |
| | | | collected part | | | | |
| | | | — | | | | |
| | | | animal No. | | | | |
| | | | 7 | 8 | 9 | 10 | 11 |
| | | | sample No. | | | | |
| Symbol | EST | Sequence_ID | 39 | 62 | 85 | 108 | 131 |
| PAPSS2 | SN009c31T_N07 | MK002114_1 | 2.22 | 1.57 | 1.91 | 1.88 | 1.64 |
| EEF1G | SN117a11T_E03 | MK000784_2 | 1.46 | 1.79 | 1.52 | 1.43 | 1.23 |
| HPRT1 | SN020d53T_J14 | MK000286_1 | 0.44 | 0.42 | 0.36 | 0.44 | 0.32 |
| PPIA | SN021d41T_B12 | MK005336_3 | 1.08 | 1.74 | 0.83 | 1.40 | 0.77 |
| PGK1 | SN091c21T_J05 | MK000332_3 | 1.47 | 0.83 | 0.65 | 1.03 | 0.93 |
| RPL4 | SN311b27T_E08 | MK000581_3 | 1.25 | 1.49 | 1.19 | 1.49 | 1.20 |
| GAPDH | SN299b55T_M14 | MK001057_3 | 0.84 | 0.96 | 0.54 | 0.87 | 0.62 |
| TBP | SN147b69T_I18 | MK001519_1 | 1.15 | 1.07 | 1.11 | 1.24 | 1.25 |
| SDHA | SN032d28T_H08 | MK001905_1 | 0.45 | 0.37 | 0.34 | 0.39 | 0.39 |
| GUSB | SN102d12T_H04 | MK000279_1 | 0.81 | 1.02 | 0.99 | 0.88 | 0.97 |
| ACTB | SN263b46T_K12 | MK000668_2 | 1.55 | 1.79 | 1.11 | 1.71 | 1.05 |
| UBC | SN032d35T_F10 | MK005306_5 | 0.91 | 0.73 | 0.54 | 0.65 | 0.84 |
| B2M | SN252c26T_D07 | MK001845_10 | 0.61 | 0.69 | 0.33 | 0.33 | 0.44 |
| TFRC | SN252a02T_C01 | MK001530_1 | 1.23 | 0.81 | 0.75 | 1.75 | 0.94 |

TABLE 13 expression data of 14 genes in each tissue - (5)
[Cy5]

| | | | collected organ | | | | | | | | |
|---|---|---|---|---|---|---|---|---|---|---|---|
| | | | skeletal muscle | | | | | lymphocyte | | | |
| | | | collected part | | | | | | | | |
| | | | — | | | | | — | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 40 | 63 | 86 | 109 | 132 | 41 | 64 | 87 | 110 | 133 |
| PAPSS2 | SN009c31T_N07 | MK002114_1 | 93 | 109 | 111 | 88 | 134 | 83 | 118 | 104 | 95 | 74 |
| EEF1G | SN117a11T_E03 | MK000784_2 | 22266 | 19762 | 22144 | 15601 | 21587 | 33209 | 22958 | 25535 | 27691 | 20366 |
| HPRT1 | SN020d53T_J14 | MK000286_1 | 344 | 421 | 498 | 339 | 507 | 771 | 664 | 608 | 706 | 666 |

TABLE 13-continued expression data of 14 genes in each tissue - (5)
[Cy5]

| Symbol | EST | Sequence_ID | | | | | | | | | |
|---|---|---|---|---|---|---|---|---|---|---|---|
| PPIA | SN021d41T_B12 | MK005336_3 | 1078 | 1049 | 813 | 1005 | 952 | 4816 | 4711 | 3473 | 3995 | 3949 |
| PGK1 | SN091c21T_J05 | MK000332_3 | 17412 | 11793 | 13529 | 8776 | 9300 | 3767 | 1786 | 1692 | 1863 | 3134 |
| RPL4 | SN311b27T_E08 | MK000581_3 | 12064 | 14154 | 11805 | 11757 | 12034 | 45283 | 41280 | 30386 | 47080 | 31069 |
| GAPDH | SN299b55T_M14 | MK001057_3 | 87997 | 81764 | 85441 | 64406 | 60816 | 6062 | 6070 | 4240 | 5211 | 5182 |
| TBP | SN147b69T_I18 | MK001519_1 | 140 | 135 | 180 | 134 | 186 | 361 | 302 | 296 | 412 | 317 |
| SDHA | SN032d28T_H08 | MK001905_1 | 5898 | 4700 | 5438 | 5832 | 6442 | 1994 | 1633 | 1060 | 1571 | 1580 |
| GUSB | SN102d12T_H04 | MK000279_1 | 399 | 425 | 395 | 384 | 434 | 1729 | 2346 | 1936 | 2428 | 2407 |
| ACTB | SN263b46T_K12 | MK000668_2 | 8019 | 8578 | 8163 | 8377 | 10213 | 76412 | 83352 | 54326 | 62451 | 72685 |
| UBC | SN032d35T_F10 | MK005306_5 | 40477 | 43311 | 41275 | 31081 | 44548 | 39529 | 33715 | 26413 | 29078 | 33623 |
| B2M | SN252c26T_D07 | MK001845_10 | 10548 | 11603 | 14782 | 8072 | 13756 | 137237 | 141232 | 103984 | 110512 | 112232 |
| TFRC | SN252a02T_C01 | MK001530_1 | 891 | 695 | 731 | 2006 | 4408 | 883 | 803 | 642 | 863 | 706 |
| | | average | 2179 | 2131 | 2103 | 2330 | 2172 | 1942 | 1826 | 1640 | 1901 | 1755 |
| | | median | 476 | 476 | 476 | 476 | 476 | 476 | 476 | 476 | 476 | 475 |
| | | standard deviation | 9306 | 9382 | 10351 | 10164 | 9134 | 6856 | 6500 | 5869 | 6911 | 6314 |
| | | number of valid spots | 16161 | 16168 | 16042 | 16060 | 16198 | 16219 | 16136 | 16111 | 16161 | 16065 |

| | | | collected organ | | | | | | | |
|---|---|---|---|---|---|---|---|---|---|---|
| | | | mesenteric lymph nodes | | | | submandibular lymph nodes | | | |
| | | | collected part | | | | | | | |
| | | | — | | | | — | | | |
| | | | animal No. | | | | | | | |
| | | | 8 | 9 | 10 | 11 | 7 | 8 | 9 | 10 | 11 |
| | | | sample No. | | | | | | | |
| Symbol | EST | Sequence_ID | 138 | 142 | 146 | 150 | 135 | 139 | 143 | 147 | 151 |
| PAPSS2 | SN009c31T_N07 | MK002114_1 | 251 | 296 | 182 | 350 | 227 | 218 | 292 | 197 | 271 |
| EEF1G | SN117a11T_E03 | MK000784_2 | 18507 | 18820 | 14477 | 16731 | 21184 | 19174 | 22242 | 17570 | 16506 |
| HPRT1 | SN020d53T_J14 | MK000286_1 | 627 | 571 | 488 | 730 | 680 | 707 | 625 | 599 | 641 |
| PPIA | SN021d41T_B12 | MK005336_3 | 3489 | 3784 | 2763 | 5299 | 4435 | 4490 | 3662 | 4144 | 4382 |
| PGK1 | SN091c21T_J05 | MK000332_3 | 1726 | 2089 | 1471 | 3832 | 3414 | 2678 | 2200 | 1966 | 3669 |
| RPL4 | SN311b27T_E08 | MK000581_3 | 30567 | 21764 | 20393 | 22985 | 37469 | 38509 | 31587 | 28362 | 22736 |
| GAPDH | SN299b55T_M14 | MK001057_3 | 4525 | 5666 | 3995 | 6297 | 6025 | 7168 | 5706 | 5719 | 5690 |
| TBP | SN147b69T_I18 | MK001519_1 | 288 | 304 | 236 | 382 | 345 | 344 | 349 | 333 | 345 |
| SDHA | SN032d28T_H08 | MK001905_1 | 1323 | 1509 | 1268 | 1785 | 1854 | 1424 | 1388 | 1490 | 1663 |
| GUSB | SN102d12T_H04 | MK000279_1 | 2215 | 2837 | 2339 | 3078 | 1909 | 2299 | 2479 | 2159 | 2523 |
| ACTB | SN263b46T_K12 | MK000668_2 | 58850 | 66667 | 58908 | 73782 | 61774 | 81229 | 65598 | 67204 | 74927 |
| UBC | SN032d35T_F10 | MK005306_5 | 27430 | 22858 | 17180 | 26408 | 31190 | 24936 | 28035 | 22502 | 20793 |
| B2M | SN252c26T_D07 | MK001845_10 | 85031 | 70245 | 45768 | 75855 | 76328 | 69512 | 72891 | 72252 | 83994 |
| TFRC | SN252a02T_C01 | MK001530_1 | 994 | 1206 | 1005 | 1543 | 1338 | 1097 | 1170 | 1391 | 1448 |
| | | average | 1935 | 2054 | 1904 | 2237 | 2215 | 2131 | 2140 | 2055 | 2114 |
| | | median | 475 | 476 | 475 | 476 | 477 | 477 | 478 | 478 | 478 |
| | | standard deviation | 7509 | 7651 | 9474 | 8430 | 7698 | 7462 | 7709 | 8672 | 8516 |
| | | number of valid spots | 16196 | 16263 | 16200 | 16372 | 16314 | 16232 | 16253 | 16243 | 16218 |

| | | | collected organ | | | |
|---|---|---|---|---|---|---|
| | | | common bile duct | | | |
| | | | collected part | | | |
| | | | — | | | |
| | | | animal No. | | | |
| | | | 8 | 9 | 10 | 11 |
| | | | sample No. | | | |
| Symbol | EST | Sequence_ID | 140 | 144 | 148 | 152 |
| PAPSS2 | SN009c31T_N07 | MK002114_1 | 1081 | 950 | 772 | 977 |
| EEF1G | SN117a11T_E03 | MK000784_2 | 11127 | 13366 | 10002 | 11935 |
| HPRT1 | SN020d53T_J14 | MK000286_1 | 343 | 378 | 388 | 400 |
| PPIA | SN021d41T_B12 | MK005336_3 | 2761 | 2642 | 2524 | 3264 |
| PGK1 | SN091c21T_J05 | MK000332_3 | 1408 | 1227 | 1365 | 2182 |
| RPL4 | SN311b27T_E08 | MK000581_3 | 16706 | 14640 | 14258 | 14415 |
| GAPDH | SN299b55T_M14 | MK001057_3 | 6695 | 6023 | 6952 | 7394 |
| TBP | SN147b69T_I18 | MK001519_1 | 248 | 207 | 215 | 252 |
| SDHA | SN032d28T_H08 | MK001905_1 | 1914 | 2163 | 2004 | 2099 |
| GUSB | SN102d12T_H04 | MK000279_1 | 1886 | 1797 | 1668 | 2187 |
| ACTB | SN263b46T_K12 | MK000668_2 | 37888 | 36875 | 29894 | 34263 |
| UBC | SN032d35T_F10 | MK005306_5 | 37225 | 34575 | 26104 | 38957 |
| B2M | SN252c26T_D07 | MK001845_10 | 51454 | 42519 | 32777 | 53741 |
| TFRC | SN252c02T_C01 | MK001530_1 | 724 | 880 | 974 | 802 |

TABLE 13-continued expression data of 14 genes in each tissue - (5)

[Cy5]

|  |  |  |  |  |  |  | | | | |
|---|---|---|---|---|---|---|---|---|---|---|
|  |  |  |  |  |  | average | 2086 | 2350 | 1792 | 2216 |
|  |  |  |  |  |  | median | 478 | 478 | 478 | 478 |
|  |  |  |  |  |  | standard deviation | 7541 | 9920 | 7235 | 8434 |
|  |  |  |  |  |  | number of valid spots | 16252 | 16238 | 16180 | 16291 |

TABLE 14

[Cy3]

| | | | collected organ | | | | | | | | |
|---|---|---|---|---|---|---|---|---|---|---|---|
| | | | skeletal muscle | | | | | lymphocyte | | | |
| | | | collected part | | | | | | | | |
| | | | — | | | | | — | | | |
| | | | animal No. | | | | | | | | |
| | | | 7 | 8 | 9 | 10 | 11 | 7 | 8 | 9 | 10 | 11 |
| | | | sample No. | | | | | | | | |
| Symbol | EST | Sequence_ID | 40 | 63 | 86 | 109 | 132 | 41 | 64 | 87 | 110 | 133 |
| PAPSS2 | SN009c31T_N07 | MK002114_1 | 702 | 712 | 716 | 759 | 779 | 761 | 798 | 716 | 799 | 782 |
| EEF1G | SN117a11T_E03 | MK000784_2 | 10217 | 10378 | 9919 | 11466 | 10986 | 10449 | 11319 | 9833 | 11295 | 11254 |
| HPRT1 | SN020d53T_J14 | MK000286_1 | 1086 | 1111 | 1082 | 1097 | 1183 | 1183 | 1196 | 1049 | 1227 | 1240 |
| PPIA | SN021d41T_B12 | MK005336_3 | 3458 | 3366 | 3224 | 3529 | 3612 | 3513 | 3657 | 3187 | 3608 | 3750 |
| PGK1 | SN091c21T_J05 | MK000332_3 | 2333 | 2311 | 2234 | 2426 | 2462 | 2533 | 2593 | 2249 | 2583 | 2654 |
| RPL4 | SN311b27T_E08 | MK000581_3 | 16000 | 15253 | 15656 | 15593 | 17017 | 13909 | 15953 | 13766 | 13879 | 16412 |
| GAPDH | SN299b55T_M14 | MK001057_3 | 7643 | 7786 | 7514 | 9195 | 9404 | 10693 | 10972 | 8882 | 10719 | 10748 |
| TBP | SN147b69T_I18 | MK001519_1 | 229 | 212 | 207 | 206 | 217 | 243 | 234 | 200 | 234 | 235 |
| SDHA | SN032d28T_H08 | MK001905_1 | 4014 | 4005 | 4077 | 4353 | 4307 | 4290 | 4368 | 3966 | 4619 | 4305 |
| GUSB | SN102d12T_H04 | MK000279_1 | 1465 | 1449 | 1390 | 1460 | 1550 | 1660 | 1774 | 1452 | 1792 | 1791 |
| ACTB | SN263b46T_K12 | MK000668_2 | 39521 | 39104 | 38303 | 41770 | 43264 | 28483 | 28803 | 26807 | 32930 | 29208 |
| UBC | SN032d35T_F10 | MK005306_5 | 31843 | 33167 | 33496 | 38968 | 33576 | 37077 | 37522 | 35641 | 40945 | 37645 |
| B2M | SN252c26T_D07 | MK001845_10 | 58914 | 59620 | 58385 | 46964 | 65731 | 28592 | 32379 | 28127 | 36886 | 28528 |
| TFRC | SN252a02T_C01 | MK001530_1 | 988 | 917 | 939 | 852 | 999 | 987 | 1035 | 906 | 1123 | 1031 |
| | | average | 2347 | 2347 | 2138 | 2626 | 2313 | 2077 | 2086 | 1878 | 2089 | 2070 |
| | | median | 510 | 510 | 510 | 510 | 511 | 511 | 511 | 511 | 511 | 511 |
| | | standard deviation | 10783 | 11570 | 9445 | 14065 | 10941 | 9508 | 10033 | 9066 | 8855 | 9907 |
| | | number of valid spots | 16161 | 16168 | 16042 | 16060 | 16198 | 16219 | 16136 | 16111 | 16161 | 16065 |

| | | | collected organ | | | | | | | | |
|---|---|---|---|---|---|---|---|---|---|---|---|
| | | | mesenteric lymph nodes | | | | | submandibular lymph nodes | | | |
| | | | collected part | | | | | | | | |
| | | | — | | | | | — | | | |
| | | | animal No. | | | | | | | | |
| | | | 8 | 9 | 10 | 11 | 7 | 8 | 9 | 10 | 11 |
| | | | sample No. | | | | | | | | |
| Symbol | EST | Sequence_ID | 138 | 142 | 146 | 150 | 135 | 139 | 143 | 147 | 151 |
| PAPSS2 | SN009c31T_N07 | MK002114_1 | 703 | 758 | 660 | 824 | 724 | 659 | 739 | 698 | 785 |
| EEF1G | SN117a11T_E03 | MK000784_2 | 9442 | 10501 | 9041 | 10928 | 10770 | 10147 | 10643 | 10523 | 10654 |
| HPRT1 | SN020d53T_J14 | MK000286_1 | 1230 | 1170 | 1007 | 1313 | 1321 | 1268 | 1327 | 1177 | 1292 |
| PPIA | SN021d41T_B12 | MK005336_3 | 3052 | 3369 | 2844 | 3737 | 3471 | 3278 | 3423 | 3240 | 3549 |
| PGK1 | SN091c21T_J05 | MK000332_3 | 2443 | 2605 | 2174 | 2802 | 2696 | 2713 | 2699 | 2506 | 2807 |
| RPL4 | SN311b27T_E08 | MK000581_3 | 15046 | 16564 | 14070 | 18255 | 17605 | 16482 | 17605 | 16576 | 18768 |
| GAPDH | SN299b55T_M14 | MK001057_3 | 8737 | 9792 | 8223 | 10192 | 9883 | 8652 | 9309 | 9382 | 9439 |
| TBP | SN147b69T_I18 | MK001519_1 | 249 | 238 | 217 | 282 | 278 | 250 | 264 | 251 | 259 |
| SDHA | SN032d28T_H08 | MK001905_1 | 3969 | 4511 | 3769 | 4723 | 4551 | 3461 | 4208 | 4422 | 4682 |
| GUSB | SN102d12T_H04 | MK000279_1 | 1541 | 1696 | 1384 | 1872 | 1819 | 1790 | 1845 | 1700 | 1822 |
| ACTB | SN263b46T_K12 | MK000668_2 | 30520 | 32024 | 27438 | 35783 | 35226 | 32965 | 34629 | 32430 | 36984 |
| UBC | SN032d35T_F10 | MK005306_5 | 38835 | 44355 | 35665 | 44875 | 43794 | 35044 | 43833 | 41431 | 40326 |
| B2M | SN252c26T_D07 | MK001845_10 | 41248 | 45684 | 44750 | 51787 | 49561 | 51280 | 48680 | 47065 | 49779 |
| TFRC | SN252a02T_C01 | MK001530_1 | 997 | 1058 | 863 | 1250 | 1225 | 858 | 991 | 1089 | 1238 |

TABLE 14-continued

| | | | | | [Cy3] | | | | | |
|---|---|---|---|---|---|---|---|---|---|---|
| | average | 2405 | 2897 | 2271 | 2972 | 2811 | 2733 | 2798 | 2544 | 2852 |
| | median | 511 | 511 | 511 | 512 | 513 | 513 | 514 | 514 | 514 |
| | standard deviation | 13998 | 20263 | 13804 | 18512 | 15702 | 16007 | 17042 | 14543 | 18470 |
| | number of valid spots | 16196 | 16263 | 16200 | 16372 | 16314 | 16232 | 16253 | 16243 | 16218 |

| | | | collected organ common bile duct | | | |
|---|---|---|---|---|---|---|
| | | | collected part | | | |
| | | | — | | | |
| | | | animal No. | | | |
| | | | 8 | 9 | 10 | 11 |
| | | | sample No. | | | |
| Symbol | EST | Sequence_ID | 140 | 144 | 148 | 152 |
| PAPSS2 | SN009c31T_N07 | MK002114_1 | 646 | 677 | 612 | 739 |
| EEF1G | SN117a11T_E03 | MK000784_2 | 9853 | 10883 | 8638 | 11089 |
| HPRT1 | SN020d53T_J14 | MK000286_1 | 1173 | 1186 | 960 | 1199 |
| PPIA | SN021d41T_B12 | MK005336_3 | 3049 | 3325 | 2700 | 3449 |
| PGK1 | SN091c21T_J05 | MK000332_3 | 2396 | 2280 | 2016 | 2604 |
| RPL4 | SN311b27T_E08 | MK000581_3 | 16367 | 17773 | 13351 | 16778 |
| GAPDH | SN299b55T_M14 | MK001057_3 | 8553 | 9121 | 7923 | 9925 |
| TBP | SN147b69T_I18 | MK001519_1 | 231 | 235 | 209 | 238 |
| SDHA | SN032d28T_H08 | MK001905_1 | 3857 | 4195 | 3444 | 4301 |
| GUSB | SN102d12T_H04 | MK000279_1 | 1570 | 1635 | 1257 | 1693 |
| ACTB | SN263b46T_K12 | MK000668_2 | 37195 | 39363 | 28662 | 40790 |
| UBC | SN032d35T_F10 | MK005306_5 | 37282 | 42929 | 32374 | 37676 |
| B2M | SN252c26T_D07 | MK001845_10 | 57476 | 58253 | 45315 | 56990 |
| TFRC | SN252a02T_C01 | MK001530_1 | 971 | 953 | 767 | 1019 |
| | | average | 2266 | 2381 | 1876 | 2321 |
| | | median | 514 | 515 | 514 | 514 |
| | | standard deviation | 9868 | 9392 | 7776 | 9221 |
| | | number of valid spots | 16252 | 16238 | 16180 | 16291 |

TABLE 15

| | | | [Ratio] | | | | | | | | | | | | | |
|---|---|---|---|---|---|---|---|---|---|---|---|---|---|---|---|---|
| | | | collected organ | | | | | | | | | | | | | |
| | | | skeletal muscle | | | | | lymphocyte | | | | | mesenteric lymph nodes | | | |
| | | | | | | | | collected part | | | | | | | | |
| | | | — | | | | | — | | | | | — | | | |
| | | | animal No. | | | | | | | | | | | | | |
| | | | 7 | 8 | 9 | 10 | 11 | 7 | 8 | 9 | 10 | 11 | 8 | 9 | 10 | 11 |
| | | | sample No. | | | | | | | | | | | | | |
| Symbol | EST | Sequence_ID | 40 | 63 | 86 | 109 | 132 | 41 | 64 | 87 | 110 | 133 | 138 | 142 | 146 | 150 |
| PAPSS2 | SN009c31T_N07 | MK002114_1 | 0.13 | 0.15 | 0.15 | 0.12 | 0.17 | 0.11 | 0.15 | 0.14 | 0.12 | 0.09 | 0.36 | 0.39 | 0.28 | 0.42 |
| EEF1G | SN117a11T_E03 | MK000784_2 | 2.18 | 1.90 | 2.23 | 1.36 | 1.96 | 3.18 | 2.03 | 2.60 | 2.45 | 1.81 | 1.96 | 1.79 | 1.60 | 1.53 |
| HPRT1 | SN020d53T_J14 | MK000286_1 | 0.32 | 0.38 | 0.46 | 0.31 | 0.43 | 0.65 | 0.56 | 0.58 | 0.58 | 0.54 | 0.51 | 0.49 | 0.48 | 0.56 |
| PPIA | SN021d41T_B12 | MK005336_3 | 0.31 | 0.31 | 0.25 | 0.28 | 0.26 | 1.37 | 1.29 | 1.09 | 1.11 | 1.05 | 1.14 | 1.12 | 0.97 | 1.42 |
| PGK1 | SN091c21T_J05 | MK000332_3 | 7.46 | 5.10 | 6.06 | 3.62 | 3.78 | 1.49 | 0.69 | 0.75 | 0.72 | 1.18 | 0.71 | 0.80 | 0.68 | 1.37 |
| RPL4 | SN311b27T_E08 | MK000581_3 | 0.75 | 0.93 | 0.75 | 0.75 | 0.71 | 3.26 | 2.59 | 2.21 | 3.39 | 1.89 | 2.03 | 1.31 | 1.45 | 1.26 |
| GAPDH | SN299b55T_M14 | MK001057_3 | 11.51 | 10.50 | 11.37 | 7.00 | 6.47 | 0.57 | 0.55 | 0.48 | 0.49 | 0.48 | 0.52 | 0.58 | 0.49 | 0.62 |
| TBP | SN147b69T_I18 | MK001519_1 | 0.61 | 0.64 | 0.87 | 0.65 | 0.86 | 1.49 | 1.29 | 1.48 | 1.76 | 1.35 | 1.15 | 1.28 | 1.09 | 1.35 |
| SDHA | SN032d28T_H08 | MK001905_1 | 1.47 | 1.17 | 1.33 | 1.34 | 1.50 | 0.46 | 0.37 | 0.27 | 0.34 | 0.37 | 0.33 | 0.33 | 0.34 | 0.38 |
| GUSB | SN102d12T_H04 | MK000279_1 | 0.27 | 0.29 | 0.28 | 0.26 | 0.28 | 1.04 | 1.32 | 1.33 | 1.36 | 1.34 | 1.44 | 1.67 | 1.69 | 1.64 |
| ACTB | SN263b46T_K12 | MK000668_2 | 0.20 | 0.22 | 0.21 | 0.20 | 0.24 | 2.68 | 2.89 | 2.03 | 1.90 | 2.49 | 1.93 | 2.08 | 2.15 | 2.06 |
| UBC | SN032d35T_F10 | MK005306_5 | 1.27 | 1.31 | 1.23 | 0.80 | 1.33 | 1.07 | 0.90 | 0.74 | 0.71 | 0.89 | 0.71 | 0.52 | 0.48 | 0.59 |
| B2M | SN252c26T_D07 | MK001845_10 | 0.18 | 0.19 | 0.25 | 0.17 | 0.21 | 4.80 | 4.36 | 3.70 | 3.00 | 3.93 | 2.06 | 1.54 | 1.02 | 1.46 |
| TFRC | SN252a02T_C01 | MK001530_1 | 0.90 | 0.76 | 0.78 | 2.36 | 4.41 | 0.89 | 0.78 | 0.71 | 0.77 | 0.68 | 1.00 | 1.14 | 1.16 | 1.23 |

TABLE 15-continued

[Ratio]

| | | | collected organ | | | | | | | | |
|---|---|---|---|---|---|---|---|---|---|---|---|
| | | | submandibular lymph nodes | | | | | common bile duct | | | |
| | | | collected part | | | | | | | | |
| | | | — | | | | | — | | | |
| | | | animal No. | | | | | | | | |
| | | | 7 | 8 | 9 | 10 | 11 | 8 | 9 | 10 | 11 |
| | | | sample No. | | | | | | | | |
| Symbol | EST | Sequence_ID | 135 | 139 | 143 | 147 | 151 | 140 | 144 | 148 | 152 |
| PAPSS2 | SN009c31T_N07 | MK002114_1 | 0.31 | 0.33 | 0.39 | 0.28 | 0.35 | 1.67 | 1.40 | 1.26 | 1.32 |
| EEF1G | SN117a11T_E03 | MK000784_2 | 1.97 | 1.89 | 2.09 | 1.67 | 1.55 | 1.13 | 1.23 | 1.16 | 1.08 |
| HPRT1 | SN020d53T_J14 | MK000286_1 | 0.51 | 0.56 | 0.47 | 0.51 | 0.50 | 0.29 | 0.32 | 0.40 | 0.33 |
| PPIA | SN021d41T_B12 | MK005336_3 | 1.28 | 1.37 | 1.07 | 1.28 | 1.23 | 0.91 | 0.79 | 0.94 | 0.95 |
| PGK1 | SN091c21T_J05 | MK000332_3 | 1.27 | 0.99 | 0.82 | 0.78 | 1.31 | 0.59 | 0.54 | 0.68 | 0.84 |
| RPL4 | SN311b27T_E08 | MK000581_3 | 2.13 | 2.34 | 1.79 | 1.71 | 1.21 | 1.02 | 0.82 | 1.07 | 0.86 |
| GAPDH | SN299b55T_M14 | MK001057_3 | 0.61 | 0.83 | 0.61 | 0.61 | 0.60 | 0.78 | 0.66 | 0.88 | 0.74 |
| TBP | SN147b69T_I18 | MK001519_1 | 1.24 | 1.37 | 1.32 | 1.33 | 1.33 | 1.07 | 0.88 | 1.03 | 1.06 |
| SDHA | SN032d28T_H08 | MK001905_1 | 0.41 | 0.41 | 0.33 | 0.34 | 0.36 | 0.50 | 0.52 | 0.58 | 0.49 |
| GUSB | SN102d12T_H04 | MK000279_1 | 1.05 | 1.28 | 1.34 | 1.27 | 1.38 | 1.20 | 1.10 | 1.33 | 1.29 |
| ACTB | SN263b46T_K12 | MK000668_2 | 1.75 | 2.46 | 1.89 | 2.07 | 2.03 | 1.02 | 0.94 | 1.04 | 0.84 |
| UBC | SN032d35T_F10 | MK005306_5 | 0.71 | 0.71 | 0.64 | 0.54 | 0.52 | 1.00 | 0.81 | 0.81 | 1.03 |
| B2M | SN252c26T_D07 | MK001845_10 | 1.54 | 1.36 | 1.50 | 1.54 | 1.69 | 0.90 | 0.73 | 0.72 | 0.94 |
| TFRC | SN252a02T_C01 | MK001530_1 | 1.09 | 1.28 | 1.18 | 1.28 | 1.17 | 0.75 | 0.92 | 1.27 | 0.79 |

TABLE 16 expression data of 14 genes in each tissue - (6)
[Cy5]

| | | | collected organ | | | | | |
|---|---|---|---|---|---|---|---|---|
| | | | bladder | | | | | lacrimal gland |
| | | | collected part | | | | | |
| | | | — | | | | | — |
| | | | animal No. | | | | | |
| | | | 7 | 8 | 9 | 10 | 11 | 7 |
| | | | sample No. | | | | | |
| Symbol | EST | Sequence_ID | 137 | 141 | 145 | 149 | 153 | 30 |
| PAPSS2 | SN009c31T_N07 | MK002114_1 | 257 | 250 | 295 | 347 | 300 | 285 |
| EEF1G | SN117a11T_E03 | MK000784_2 | 12316 | 13843 | 14639 | 14152 | 12536 | 11129 |
| HPRT1 | SN020d53T_J14 | MK000286_1 | 352 | 362 | 328 | 319 | 293 | 379 |
| PPIA | SN021d41T_B12 | MK005336_3 | 2598 | 3848 | 3295 | 3853 | 3747 | 1382 |
| PGK1 | SN091c21T_J05 | MK000332_3 | 2587 | 1976 | 2090 | 1971 | 2948 | 1120 |
| RPL4 | SN311b27T_E08 | MK000581_3 | 15685 | 21345 | 20167 | 23559 | 17966 | 11515 |
| GAPDH | SN299b55T_M14 | MK001057_3 | 6068 | 8563 | 7436 | 8490 | 6641 | 2884 |
| TBP | SN147b69T_I18 | MK001519_1 | 238 | 248 | 256 | 253 | 239 | 157 |
| SDHA | SN032d28T_H08 | MK001905_1 | 1982 | 1566 | 1480 | 1830 | 1662 | 1120 |
| GUSB | SN102d12T_H04 | MK000279_1 | 1330 | 2089 | 2354 | 2127 | 2025 | 1230 |
| ACTB | SN263b46T_K12 | MK000668_2 | 53594 | 69741 | 79461 | 68277 | 67774 | 11328 |
| UBC | SN032d35T_F10 | MK005306_5 | 32430 | 30569 | 34340 | 32976 | 36052 | 22197 |
| B2M | SN252c26T_D07 | MK001845_10 | 19290 | 51491 | 29046 | 29251 | 27138 | 15344 |
| TFRC | SN252a02T_C01 | MK001530_1 | 686 | 1091 | 1207 | 1838 | 945 | 926 |
| | | average | 1762 | 2004 | 2005 | 2046 | 1785 | 2215 |
| | | median | 478 | 478 | 477 | 477 | 477 | 476 |
| | | standard deviation | 7123 | 7362 | 7424 | 7731 | 7371 | 10003 |
| | | number of valid spots | 16207 | 16198 | 16153 | 16286 | 16128 | 16077 |

TABLE 17

| | | | [Cy3] | | | | | |
|---|---|---|---|---|---|---|---|---|
| | | | collected organ | | | | | |
| | | | bladder | | | | | lacrimal gland |
| | | | collected part | | | | | |
| | | | animal No. | | | | | |
| | | | 7 | 8 | 9 | 10 | 11 | 7 |
| | | | sample No. | | | | | |
| Symbol | EST | Sequence_ID | 137 | 141 | 145 | 149 | 153 | 30 |
| PAPSS2 | SN009c31T_N07 | MK002114_1 | 603 | 620 | 632 | 688 | 615 | 601 |
| EEF1G | SN117a11T_E03 | MK000784_2 | 8332 | 9099 | 9818 | 9644 | 8811 | 8105 |
| HPRT1 | SN020d53T_J14 | MK000286_1 | 985 | 1137 | 1148 | 1069 | 1025 | 995 |
| PPIA | SN021d41T_B12 | MK005336_3 | 2468 | 2976 | 3058 | 3161 | 2908 | 2642 |
| PGK1 | SN091c21T_J05 | MK000332_3 | 1984 | 2374 | 2512 | 2405 | 2146 | 2093 |
| RPL4 | SN311b27T_E08 | MK000581_3 | 13385 | 15773 | 16576 | 14398 | 13052 | 14024 |
| GAPDH | SN299b55T_M14 | MK001057_3 | 7701 | 7957 | 8506 | 8100 | 8235 | 7588 |
| TBP | SN147b69T_I18 | MK001519_1 | 211 | 222 | 223 | 226 | 201 | 200 |
| SDHA | SN032d28T_H08 | MK001905_1 | 3475 | 3355 | 3548 | 3896 | 3407 | 3428 |
| GUSB | SN102d12T_H04 | MK000279_1 | 1198 | 1576 | 1636 | 1550 | 1398 | 1331 |
| ACTB | SN263b46T_K12 | MK000668_2 | 24420 | 30928 | 31282 | 31155 | 25000 | 33957 |
| UBC | SN032d35T_F10 | MK005306_5 | 30958 | 32691 | 34542 | 37698 | 31674 | 31930 |
| B2M | SN252c26T_D07 | MK001845_10 | 45600 | 50242 | 65241 | 56676 | 50350 | 52189 |
| TFRC | SN252a02T_C01 | MK001530_1 | 861 | 794 | 834 | 899 | 790 | 818 |
| | | average | 1965 | 2325 | 2373 | 2168 | 1836 | 2256 |
| | | median | 514 | 513 | 513 | 513 | 512 | 511 |
| | | standard deviation | 9551 | 11844 | 12426 | 9057 | 7857 | 13166 |
| | | number of valid spots | 16207 | 16198 | 16153 | 16286 | 16128 | 16077 |

TABLE 18

| | | | [Ratio] | | | | | |
|---|---|---|---|---|---|---|---|---|
| | | | collected organ | | | | | |
| | | | bladder | | | | | lacrimal gland |
| | | | collected part | | | | | |
| | | | animal No. | | | | | |
| | | | 7 | 8 | 9 | 10 | 11 | 7 |
| | | | sample No. | | | | | |
| Symbol | EST | Sequence_ID | 137 | 141 | 145 | 149 | 153 | 30 |
| PAPSS2 | SN009c31T_N07 | MK002114_1 | 0.43 | 0.40 | 0.47 | 0.50 | 0.49 | 0.47 |
| EEF1G | SN117a11T_E03 | MK000784_2 | 1.48 | 1.52 | 1.49 | 1.47 | 1.42 | 1.37 |
| HPRT1 | SN020d53T_J14 | MK000286_1 | 0.36 | 0.32 | 0.29 | 0.30 | 0.29 | 0.38 |
| PPIA | SN021d41T_B12 | MK005336_3 | 1.05 | 1.29 | 1.08 | 1.22 | 1.29 | 0.52 |
| PGK1 | SN091c21T_J05 | MK000332_3 | 1.30 | 0.83 | 0.83 | 0.82 | 1.37 | 0.54 |
| RPL4 | SN311b27T_E08 | MK000581_3 | 1.17 | 1.35 | 1.22 | 1.64 | 1.38 | 0.82 |
| GAPDH | SN299b55T_M14 | MK001057_3 | 0.79 | 1.08 | 0.87 | 1.05 | 0.81 | 0.38 |
| TBP | SN147b69T_I18 | MK001519_1 | 1.12 | 1.12 | 1.14 | 1.12 | 1.19 | 0.78 |
| SDHA | SN032d28T_H08 | MK001905_1 | 0.57 | 0.47 | 0.42 | 0.47 | 0.49 | 0.33 |
| GUSB | SN102d12T_H04 | MK000279_1 | 1.11 | 1.33 | 1.44 | 1.37 | 1.45 | 0.92 |
| ACTB | SN263b46T_K12 | MK000668_2 | 2.19 | 2.25 | 2.54 | 2.19 | 2.71 | 0.33 |
| UBC | SN032d35T_F10 | MK005306_5 | 1.05 | 0.94 | 0.99 | 0.87 | 1.14 | 0.70 |
| B2M | SN252c26T_D07 | MK001845_10 | 0.42 | 1.02 | 0.45 | 0.52 | 0.54 | 0.29 |
| TFRC | SN252a02T_C01 | MK001530_1 | 0.80 | 1.38 | 1.45 | 2.05 | 1.20 | 1.13 |

EXAMPLE 4

Carbon tetrachloride, which is a typical hepatotoxic substance, was administered to *Macaca fascicularis*, and the liver was collected 6 and 24 hours later by biopsy to study changes in the gene expression. As a result, changes in the expression of the gene involved in HSP, proteasome, transcription factor and signal transduction were observed 6 hours later.

INDUSTRIAL APPLICABILITY

The gene expression analysis tool of the present invention can analyze gene expression of *Macaca fascicularis* quantitatively with high accuracy, since it contains nucleic acid(s) capable of detecting expression of at least two kinds of housekeeping genes derived from *Macaca fascicularis*. The tool is utilized for the search of a marker gene relating to the toxicity, pharmacological action and disease, as well as analysis of the mechanisms thereof, and is useful for the research and development of pharmaceutical product candidate compounds and the like.

This application is based on a patent application No. 2006-019858 filed in Japan, the contents of which are incorporated in full herein by this reference.

The invention claimed is:

1. A *Macaca fascicularis* gene expression analysis tool comprising at least two isolated nucleic acid sequences selected from the group consisting of SEQ ID NOs: 1, 3, 4, 5, 6, 7, 8, 11, 12 and 14.

2. A *Macaca fascicularis* gene expression analysis tool comprising each isolated nucleic acid sequence of the nucleic acid sequences of SEQ ID NOs: 1, 3, 4, 5, 6, 7, 8, 11, 12 and 14.

3. The tool of claim 1 or 2, further comprising at least one isolated nucleic acid sequence or partial sequence thereof of a *Macaca fascicularis* gene transcription product specifically expressed in an organ selected from the group consisting of liver, kidney, heart, lung, spleen and testis, and/or corresponding to a drug efficacy target in a human.

4. The tool of claim 1 or 3, wherein said at least two isolated nucleic acid sequences are immobilized on a solid phase carrier.

5. A *Macaca fascicularis* gene expression analysis tool comprising an isolated nucleic acid sequence comprising 95% or more homology to the nucleic acid sequence of SEQ ID NO: 12.

* * * * *

UNITED STATES PATENT AND TRADEMARK OFFICE
CERTIFICATE OF CORRECTION

| | | |
|---|---|---|
| PATENT NO. | : 8,138,123 B2 | |
| APPLICATION NO. | : 12/162253 | |
| DATED | : March 20, 2012 | |
| INVENTOR(S) | : Nobuyuki Miyajima et al. | |

It is certified that error appears in the above-identified patent and that said Letters Patent is hereby corrected as shown below:

Cover Page, item (54), and column 1, "GENE EXPRESSING ANALYSIS TOOL", should be -- GENE EXPRESSION ANALYSIS TOOL --.

Column 5, line 21, "cDNA(s) from a CDNA or genomic DNA library from the", should be -- cDNA(s) from a cDNA or genomic DNA library from the --.

Signed and Sealed this
Sixth Day of November, 2012

David J. Kappos
*Director of the United States Patent and Trademark Office*

```
                        SEQUENCE LISTING

<160> NUMBER OF SEQ ID NOS: 14

<210> SEQ ID NO 1
<211> LENGTH: 763
<212> TYPE: DNA
<213> ORGANISM: Macaca fascicularis

<400> SEQUENCE: 1
ctccctaggc ccctcccctc ttcaaggggt ctacatggaa actgagggga gattcagtgt      60
ggcgggggac tgagtgtggc agggactccc cagcagtgag ggcctctctc ttcctcttgt     120
gctctcgctg gggctggtgg tccgggggtc ttactccttg gaggccatgt gggccatgag     180
gtccaccacc ctgttgctgt agccaaattc gttgtcatac caggaaatga gcttgacaaa     240
gtggtcgttg agggcaatgc cagccccagc gtcgaaggtg aagagtggg tgtcgctgtt      300 gaagtcggag gagaccacct ggtgctcagt gtagcccagg atgcccttga gggggccctc     360
cgacgcctgc ttcaccacct tcttgatgtc atcgtacttg gcaggttttt ccagacggca     420
ggtcaggtcc accactgaca cgttggcagt ggggacacgg aaggccatgc cagtgagctt     480
cccgttcagc tcagggatga ccttgcccac agccttggca gcgccagtag aggcagggat     540
gatgttctgg agagctccgc ggccatcacg ccacagtttc ccggaggggc catccacagt     600
cttctgggtg gcagtgatgg cgtggactgt ggtcatgagt ccttccacga taccaaagtt     660
gtcatggatg accttggcca ggggtgctaa gcagttggtg gtgcaggagg cgttgctgac     720
gatcttgagg ctgttgtcat acttctcatg gttcacaccc atg                      763

<210> SEQ ID NO 2
<211> LENGTH: 800
<212> TYPE: DNA
<213> ORGANISM: Macaca fascicularis

<400> SEQUENCE: 2
tgtacaggta agccctggct gcctccaccc actcccaggg agaccaaaag ccttcagaca      60
tctcaagttg ggggacaaaa agaggggggca tgaaggctca ttattcaaaa taaaacaaaa    120
taaaaaagta ttaaggcgaa gattaaaaaa attttgcatt acataattta cacgaaagca    180
atgctatcac ctcccctgtg tggactcggg agaggactgg gccattctcc ttagagaaa     240 gtggggtggc ttttaggagg gcaagggact tcctgtaaca atgcatctca tatttggaat    300
gactattaaa aaaaagaaca atgtacaatc aaagtcctcg gccacattgt agaactttgg    360
gggatgctcg ctccaaccga ctgctgtcac cttcaccgtt ccagtttta aatcctgagt     420 caagccaaaa aaaaaaaacc aaaacaaaac aaaaaaaaca aataaagcca tgccaatctc    480
```

| | |
|---|---|
| atcttgtttt ctgcgcaagt taggttttgt caagaaaggg tgtaacgcaa ctaagtcaca | 540 |
| gtccgcctag aagcatttgc ggtggacgat ggaagggcca gactcgtcat actcctgctt | 600 |
| gctgatccac atctgctgga aggtggacag cgaggccagg atggagcctg ccgatccaca | 660 |
| cagagtactt gcgctcagga ggagcaatga tcttgatctt catcgtgctg ggcgccaggc | 720 |
| agtaatctcc ttctgcatcc tgtcagcaat gccagggtac atggtggtgc caccagacag | 780 |
| cactgtgttg gcgtacaggt | 800 |

<210> SEQ ID NO 3
<211> LENGTH: 788
<212> TYPE: DNA
<213> ORGANISM: Macaca fascicularis

<400> SEQUENCE: 3

| | |
|---|---|
| atctcacaag aatgaagcaa gggacaaagg taagtgccac gttccctggc cactgggttc | 60 |
| ctggcaagct accagccact gggtgccaat ctcccttcaa tgtactcctt tttccccaga | 120 |
| gtgcagaagc gtataaaggc agttatgaca tggacacatg catgagctat tatacataat | 180 |
| tacaaaagct gattctgtta tcactgcatc ttgtctcatc agtaggagcg aatggctggg | 240 |
| gggacggtgg cacagtcagc ctcgttcaaa gttttgtcga ttacgggtct atattccaga | 300 |
| gtgaccttcc cagtgctgac gtccacatag acagggtgt gcttcctcca gtgctcctca | 360 |
| aaaggcttct tctgttgccc ctggatgggc ttggagtaat cgtactcatc aatccgcacc | 420 |
| ttgtagtctt ccctggcgtg tgcgcccgt gactccttcc gcgcctctgc tccgtagatg | 480 |
| gtctgcagcg cacacagcat caggttctgc agctccaggg tctccaccag gtccgtgttc | 540 |
| cagaccattc cccggtcaaa cgtcttcagg tgcttcaggt ctccgtagag cttgctgatt | 600 |
| ttcccacaac cttcttgcaa cacgcttccc acacggaaca cggcagcatg attttgcatt | 660 |
| gacttctgca tgctgagtcg aagttctgac gttcttatgc ttccgtcagc aaatctcaat | 720 |
| ttgtcaagat tcatgacaga ttcttctcca gcatttggtt taattggagg gactttatct | 780 |
| ccaggcct | 788 |

<210> SEQ ID NO 4
<211> LENGTH: 816
<212> TYPE: DNA
<213> ORGANISM: Macaca fascicularis

<400> SEQUENCE: 4

| | |
|---|---|
| gtgacccctta tggaataatc aaatttaaga gttcatgcag caggcttctt ttcctctgta | 60 |
| gtaggtttct tttccgcagg cttctttca ggggctggtt tcttggtagc tgctgccttt | 120 |
| tttcccacca gaggcttctt ctgcttctta acaccaacag cagccttctt tcctttctta | 180 |
| cctaccacag gcttcttgcc tgcaaccgcc gccttctcat ctgatttggc ttctagtgct | 240 |
| gctgctgcag cagctgcctt atccacccgg agcttgtgat tcctggcctg gcgaagaatg | 300 |
| gtattccggc gcatggtctt tgcatatggg tttagcttca acatgattct caggttttc | 360 |
| agtgggttct tctttaggac tctacgatga atcttcttgc gtggtgctcg aagggctctt | 420 |
| tggatctctg ggcttttcaa gattctgcta agatctgtat taatcatctt gtgcatggga | 480 |
| agattgtagt tactcttgag ggaagcggct ttacgccaag tgccatacaa ttcatctaac | 540 |
| ttccggaaag cactctcagt ccaaatgcag aaacgtccca catgccacc aggagcaagc | 600 |
| ttcaaaatgt tcagtttgct tacattaagc agagtaattc cagggatgtt tctgaaggcc | 660 |
| ttgatgatac cattatcctc attatagatg atgcatggcc tctgcgctgg atacggcgac | 720 |

-continued

```
ggtttctcat tttgcctttg ccagctctca ttcgctgaga ggcatagacc ttttttgatat     780 catttccagg cttttaagttt tcttaaggag caaaac                              816

<210> SEQ ID NO 5
<211> LENGTH: 789
<212> TYPE: DNA
<213> ORGANISM: Macaca fascicularis

<400> SEQUENCE: 5
ggatgtgtct ggcacagaaa taaccoctag gagttacaaa ttagaaaaac aacactttta     60
aaaaagattt ttacttttct ggtagaaata taaaaactgt ggttcatggg gaaaaacatt    120
aaaattaaaa agtccaatca attgtagagg tggctttcac tcttagagtt ttctccctca    180
aaccaacttg tcaacagcag tgtttaaaat ctacatataa ataaatgggc agcgctgccc    240
agatagcagc acagtatgag caactcacag tcacgctgcg cggtgttctc agtgcacaaa    300
taatgcccct tcccggcatc ctgcggtggg cacttacaga agggcatcac ctggtgccac    360
aacctgcaac tcaacatcca tcttctcaca ccaccaccag ttaaaggtac caaaacaaac    420
tgatttgttt aaaaaaaaaa aaaacaaaca gtgggtgggg gaggcaaggg tacatgacag    480
ccattacgtc gtcttcctga atccctttag aatagggtag atgttttcaa atgcttcata    540
aatttctgct ctgactttag cacctgttaa tacaacttttt ccagaaacaa aaataaggag    600
aacaattctg ggtttgatca ttctgtagat taaaccagga ataactctg gctcataact     660 actaaactgt tggtgggtga gcacaagacc ttctaacctt ataggaaact tcacatcaca    720
gctccccacc atgttctgaa tcttgaagtc caagaactta gctggaaaac ccaacttctg    780
tacaacttc                                                             789

<210> SEQ ID NO 6
<211> LENGTH: 769
<212> TYPE: DNA
<213> ORGANISM: Macaca fascicularis

<400> SEQUENCE: 6
ttcactggta ataatctgaa caagttggaa aatacagtca acactactga aacactacta     60
aaataattcc aggacacaac aaaacttctt agatgctgtc tttgatgtga aaattgactg    120
cttcttactt ttctaaacac atggtggtat aattaacaat attcaatcac ttctgttctt    180
tcctgcatat ataaaaatta aaataccaat taaaaaacta atatatcctc tcttttatttc   240 ttacagatac gagttcaatg tttcactcaa tagtggtgtg gttaagaga attttttcat    300 ttacaagtta acaacaatc cacccaaagg gaactgatag tctataggct catagtgcaa    360
ataaacagtt taggaatgca gcaactgaca tttctaaagt acaaaacaga taaaattctt    420
agaagataca tgcaaaaagc tctactaagc agatggccac agaactagaa cattgataat    480
tttactggcg atgtcaatag gactccagat gtttccaaac tcaacttgaa ctctcatctt    540
aggctttgta ttttgctttt ccagtttcac taatgacaca acatgattc aaatccctga    600 agtattcatt atagtcaagg gcatatccta caacaaactt gtctggaatt tcaaatccaa    660
caaagtctgg cttatatcca acacttcgtg gagtcctttt caccagcaag cttgcgacct    720
tgaccatctt tggattatac tgcctgacca aggaaaagca aagtctgca                 769

<210> SEQ ID NO 7
<211> LENGTH: 693
<212> TYPE: DNA
<213> ORGANISM: Macaca fascicularis
```

<400> SEQUENCE: 7

```
tgcaatccag ctaggcatgg gagagaacaa ggaaaacatg gaacccaaag ggaactgcag      60
cgagagcaca aagattctag gatactgcga gcaaatgggg tggaggggtg ctctcctgag     120
ctacagaagg aatggtctgg tggttaagat aaaacacaag tcaaacttat tcgagttgtc     180
cacagtcagc aatggtgatc ttcttgctgg tcttgccatt cctggaccca aagcgctcca     240
tggcctccac aatattcatg ccttctttca ctttgccaaa gaccacatgc ttgccatcca     300
accactcagt cttggcagtg cagatgaaaa actgggaacc atttgtgttg ggtccagcat     360
ttgccatgga caagatgcca ggacctgtat gctttaggat gaagttctca tcttcaaatt     420
tctccccata gatggacttg ccaccagtgc cattatggcg tgtgaagtca ccaccctgac     480
acataaaccc tggaataatt ctgtgaaagc aggaaccctt ataaccaaat cctttctctc     540
cagtgctcag agcacgaaaa ttttctgctg tctttggaac cttgtctgca aacagctcga     600
aggagacgcg gcccaaaggc tcgccgtcga cggcaatgtc gaagaacacg gtagggttga     660
ccatggctag tagtacagga cttctcctcgg cgc                                 693
```

<210> SEQ ID NO 8
<211> LENGTH: 782
<212> TYPE: DNA
<213> ORGANISM: Macaca fascicularis

<400> SEQUENCE: 8

```
aggcagctag gcgatggcaa gagatgttca cttgaagatc ttgccctgat tgaaggcttt      60
gcccacatgc tggaaggccc cctcccagga aaagtactct cgaaccagcg tctgggtctc     120
ctcgctgcca ggatccagtt tccgccatgt gtatgactcg tagtccacct gccaatctgg     180
actcagcgga aaggcaagct cctggcctcg gaagacccag actccagaaa tggagctgct     240
attgttggtt ccaaagagga tgacactggc gaaggcattc ttcctcagct tgtccagtcg     300
ctggaacatt ccagtgatga gattgcagct catgaaggtc tgagtgagtt cttcagggaa     360
gcgatactct gagtaccaca gggaccagcc gtccttatca aagtgttccc agaaatatgg     420
cagtgccaca gagagtgtgt cctcattgga gtacttgcgc ttaaattcat ccaacacaaa     480
ggtactcttg gcaagtgagc gaaggggtc cttggccttg ggctcagcag ccagcgcctg     540
ctcacattca tccatctcct cctcaggagc aggggcagcc gccttttttct cctccttccg     600
ctcagcctgg ggcttctgct tctcttcccg tgaacccttc tctttccgtg gtgtatcttt     660
tttaggctgt gtctctgcaa acttttttagc atcaaactgg gccatcttct cacacagctt     720
cacttctccc aagacagctc ggaactgggg ctgattaatg caggtgagga accagcggtt     780
gg                                                                    782
```

<210> SEQ ID NO 9
<211> LENGTH: 754
<212> TYPE: DNA
<213> ORGANISM: Macaca fascicularis

<400> SEQUENCE: 9

```
aactgataaa tgcacattgtt aagagtgcag gttggcaaga catgctggaa aatatattca      60
tttttcatca agtaactaga cacatggtca aagctttaag aaatctggga cctgcctgct     120
cagatgcagt agaaaataca tagagctaat tttattctga aatgtataag aatattgctt     180
tcacctgcta agatttggtc ttcagtttga ctttgtgtgt ttgtgtatgt gtgtgtattt     240
aaattataga cacaacttt acttcattat aaaagattaa aatgcatcat tgagaagcaa     300
```

```
tttaatacaa agcatctaat cataaaaata gaaaaggtaa tcaaagagca cttcagaaag    360
aaactctgga gccaaaggca ttagttcttc tccaggacc tgtaataatc tgtcaggacc    420
ttccatgctt tgggggccat gaagccgtct ggaggattct ctccttcccg ggcgagcttc    480
ctcatacgag ttcctgagat gaagtcaaac tcattgtgcc ttgctggatc atagaagtcc    540
atggcttttt tggctttgtt gtaggcagcc actcggaatg gaatgatttc cacagaggtg    600
aggccagggg ccatgctcaa gaccttgccc ccatgagtgg gttcatacag atccttcttg    660
gtttcaggat ggggcattcc tgcagggtcc ctgcccacaa tgtagaaatt ggcccctgca    720
atcatccggg acctgcagtg ccactggacc tctg                                754

<210> SEQ ID NO 10
<211> LENGTH: 778
<212> TYPE: DNA
<213> ORGANISM: Macaca fascicularis

<400> SEQUENCE: 10
cattttgtct ccctacctac aaatggaatt tcatcttgtt tccatgctga gtagtgaaac     60
agtgacaaag ctaatcataa tagcctacat caaaagagaa ctaagctaac acagctcact    120
tggttttaac aggcaaaata taaatatatg cactctagaa tgcacaatgt ttagtcacta    180
agaaattcaa atgggatctt gaagaatgta ggcaaatcca gggtgcagta agatgagct     240 gagatgctgt gcaactgttt aagggttcct ggcactgcat ctcttggcca ctagctgaac    300
cttgacatgg aaggttttag ctaatgccaa gtggagttgc agaaaatgct aagttgactt    360
aggggctgtg cacaggaact aaaaggcagg aaagtactaa atattgctga gagcatccac    420
cccaggaagg actttacctt ccaggagctc caaactggca ccaccccag tgctcacatg     480 gctgacttta tcctccgtgt tccatttggc acagcaagtg gcagtgtctc caccacctat    540
gatggtgatg cagcccctag aagtggcttt caccacctca tccatgaggg ctttggttcc    600
ctgggcaaaa gcttcccatt caaataccc cacaggacca ttccacacaa tctgcttagc     660
ccgagtgaca gcctcagcat acttcttgct gctttcagac cacagtccaa acccatccag    720
ccagcagtat gccagaagcc acagtggctt ggccagtctt ggcattctca tcaaactt     778

<210> SEQ ID NO 11
<211> LENGTH: 595
<212> TYPE: DNA
<213> ORGANISM: Macaca fascicularis

<400> SEQUENCE: 11
aagttctaga atagcgaatc atgacagaac tcactaattg tatcctttac ctccaaaagg     60
cccatctcct taacgagaag acatctgaag accaggagct tgtcactagt ctggtatttc    120
attcaggaat attgagcctg ttaccacaca ctggcttgat aggaagtaac tcaaccctac    180
tatagaagag ggttttctga agagactgac tgctgcaaaa tgtatgcctt ttattcatgt    240
tgtgttacac tatgagtatg tcacacactt tcatttaagt atgtaagcgt aacacccaaa    300
ccaggaatct cggctatgac cttttcacat agctacacta atgtcagtc ccagataaaa     360 gaggagatta aagataaaac tgaagatgaa agagactgtg agtagtgaaa cgattccagt    420
gaggctgtaa atctaggtga gttacactaa gaacctcaag agaccccctat gagcctcttc    480 ctaggaggca gtttcaaact gcccctatgac aaacagctga tcacgtttat aacgatggtt    540
cactcatgta gcttcaaact tattcatacc tacatttaat ttataaccac aaatg         595
```

```
<210> SEQ ID NO 12
<211> LENGTH: 786
<212> TYPE: DNA
<213> ORGANISM: Macaca fascicularis

<400> SEQUENCE: 12
tttccacctc tagtggtccc tgctagcaca gatgagcata aaacccaggc cagaaacgtt      60
ctggtctgcc atgaacttgt tctgctgctg tggaagtcgc cctgactctg ggaggaaggg     120
cacacaggtg gtgtcagtct tgctcaagta acgggctgt tttccaaaca ctgtgacttg      180
gctattgagt agggatacct ggtttcattg gcaatcttcc agtatctctc tcgcaaaagg     240
aacgctgcac ttttttggttg tctctgccga gtgaagaccc ccttttttatt ccccagcact   300 ctcgtcggtg actgttcagt catgaaatcg gcaaaattcc agatgagctc tccaaccacg     360
tactttctgc gttttttgatc cagaaccaca tggtactgct ctagcagact cttctggtac    420
tcttcagtga acatcagagg cgggtcctgg tgaaacccaa caatcgtttc cgctccatac     480
tcgctctgaa taatgggctt ctgatacgtc ttataccagc tctcaaactg ggtggtaagc     540
tgctgctgaa tcaactccag gtgcccatag tcgtgatacc aagagtagta gctgttcaaa     600
cagatcacat ccacatacgg agccccttg tctgctgcat agttggagtt ggttacaaag      660
gtcacaggcc gggaggggtc caaggctttg gtgtgagtga tcaccatctt caagtagtag     720
ccggcagatt ctaggtggga tgcaggctcg ttggccacag accacatcac gacggcgggg    780
tggttc                                                                786

<210> SEQ ID NO 13
<211> LENGTH: 818
<212> TYPE: DNA
<213> ORGANISM: Macaca fascicularis

<400> SEQUENCE: 13
accacaactt tatcaaatgt ataagaagta aatatgaatc ttatatgaca aaatgtttta     60
ctcattataa caaatttcca ataacccat caattatatt tctaaatttt tcctccaaat    120
tctaagcaca gtatgtaaat tggaagttaa cttatatacg cataactatc ttatcaagct    180
tcgagtgcaa gagattgaag agctcagatc tgaccaagat gttgatgttg gatatgagaa    240
ttctctgctc cccacctcta agttgccagc cctcctaaag ctagctgccc agataccctca   300 aacgtggaga tagcactcaa agtagaatta taaagaagat catgcctgtg ttaacattat    360
tataactctg cattttttgc ataaactgta taagcatatc aatattaaaa gcaaggaag    420 cagaatttgg aattcatcca atccaaatgc ggcatcttca aacctccatg atgctgctta    480
catgtctcga tcccacttaa ctgtcctggg ccctgacaaa gtcacatggt tcacacggca    540
ggcatactca tcttttttcat tgggggtgaa ttcagtgtag tacaagagat agaaagacca    600
gtctttgctg aaagacaagt ctgaatgctc cacttttccc attttctctc cattcttcag    660
taagtcaact tcaatatcag atggatgaaa tccagacaca tagcaattca ggaaatttgg    720 cttttccattc tctggtggat ggcgtgagta aacctgaatc tttggagtac gctggatagc   780
ctccaggcca gaaagagaga gtagcgccag cacggcta                             818

<210> SEQ ID NO 14
<211> LENGTH: 776
<212> TYPE: DNA
<213> ORGANISM: Macaca fascicularis
```

```
<400> SEQUENCE: 14
tgaaccttaa aagggggaaac ttagacaccc cccctcaagc gcaggaccaa gtgcagagtg      60
gactctttct ggatgttgta gtcagacagg gtgcgtccat cttccagctg tttcccagca     120
aagatcaacc tctgctggtc aggagggatg ccttccttgt cctggatctt tgccttgaca     180
ttctcaatgg tgtcgctggg ctccacctca agggtgatgg tcttgccagt gagggtcttc     240
acgaagatct gcatcccacc tctgaggcgg agcaccaggt gcagggtgga ctctttctgg     300
atgttgtagt cagacagggt gcgcccatct tccagctgtt tcccagcaaa gatcaacctc     360
tgctggtcag gagggatgcc ttccttatcc tggatctttg ccttgacatt ctcaatggtg     420
tcgctgggct ccacctcgag ggtgatggtc ttgccagtca gggtcttcac gaagatctgc     480
atcccacctc tgagacggag cacgaggtgc agggtggact ctttctggat gttgtagtca     540
gacagggtgc gcccatcttc cagctgcttt ccggcaaaga tcaacctctg ctggtcagga     600
gggatgccct ccttgtcctg gatctttgcc ttgacatttt caatagtgtc actgggctcg     660
acctcaaggg tgatggtctt gccagtcagg gtcttcacga agatctgcat cccacctctg     720
agacggagca cgaggtgcag ggtggactct ttctggatgt tgtagtcaga cagggt        776
```